US012606567B2

(12) United States Patent
Hopkins et al.

(10) Patent No.: US 12,606,567 B2
(45) Date of Patent: Apr. 21, 2026

(54) SALTS AND FORMS OF A WEE1 INHIBITOR

(71) Applicant: Recurium IP Holdings, LLC, San Diego, CA (US)

(72) Inventors: Chad Daniel Hopkins, San Diego, CA (US); Peter Qinhua Huang, San Diego, CA (US); Kevin Duane Bunker, Escondido, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 471 days.

(21) Appl. No.: 18/004,628

(22) PCT Filed: Jul. 8, 2021

(86) PCT No.: PCT/US2021/070851

§ 371 (c)(1),
(2) Date: Jan. 6, 2023

(87) PCT Pub. No.: WO2022/011391

PCT Pub. Date: Jan. 13, 2022

(65) Prior Publication Data

US 2023/0265097 A1 Aug. 24, 2023

Related U.S. Application Data

(60) Provisional application No. 63/049,996, filed on Jul. 9, 2020.

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC .......................... C07D 487/04; C07B 2200/13
See application file for complete search history.

(56) References Cited

U.S. PATENT DOCUMENTS

| | | | |
|---|---|---|---|
| 11,124,518 | B2 | 9/2021 | Huang et al. |
| 11,261,192 | B2 | 3/2022 | Huang et al. |
| 2020/0157112 | A1 | 5/2020 | Huang et al. |
| 2021/0139482 | A1 | 5/2021 | Huang et al. |
| 2021/0317124 | A1 | 10/2021 | Huang et al. |

(Continued)

FOREIGN PATENT DOCUMENTS

| | | |
|---|---|---|
| TW | 202003512 A | 1/2020 |
| WO | WO 2019/028008 | 2/2019 |

(Continued)

OTHER PUBLICATIONS

Ashizawa Kazuhide, Polymorphic Phenomena of Pharmaceuticals and the Science of Crystallization, 2002, pp. 273, 278, 305-317.

(Continued)

*Primary Examiner* — Andrew D Kosar
*Assistant Examiner* — John D McAnany
(74) *Attorney, Agent, or Firm* — Knobbe, Martens, Olson & Bear, LLP

(57) ABSTRACT

The salt, such as adipate salt Form A, and freebase forms of Compound A are WEE1 inhibitors. Such salts and/or forms and freebase forms, as well as pharmaceutically acceptable (Continued)

salts and compositions thereof, are useful for treating diseases or conditions, including conditions characterized by excessive cellular proliferation, such as breast cancer.

23 Claims, 25 Drawing Sheets

(56) References Cited

U.S. PATENT DOCUMENTS

| | | | |
|---|---|---|---|
| 2022/0024939 A1 | 1/2022 | Huang et al. |
| 2023/0002426 A1 | 1/2023 | Huang et al. |
| 2023/0008362 A1 | 1/2023 | Samatar et al. |
| 2023/0068370 A1 | 3/2023 | Samatar et al. |
| 2023/0087941 A1 | 3/2023 | Samatar et al. |
| 2023/0210854 A1 | 7/2023 | Samatar et al. |
| 2023/0234956 A1 | 7/2023 | Huang et al. |
| 2024/0197743 A1 | 6/2024 | Pultar et al. |
| 2024/0261295 A1 | 8/2024 | Donate et al. |
| 2024/0299395 A1 | 9/2024 | Donate et al. |
| 2024/0325397 A1 | 10/2024 | Samatar et al. |
| 2024/0325412 A1 | 10/2024 | Donate et al. |
| 2024/0335447 A1 | 10/2024 | Donate et al. |
| 2024/0391924 A1 | 11/2024 | Huang et al. |
| 2024/0408097 A1 | 12/2024 | Samatar et al. |
| 2025/0205240 A1 | 6/2025 | Jameson et al. |
| 2025/0208149 A1 | 6/2025 | Harismendy et al. |
| 2025/0262214 A1 | 8/2025 | Ma et al. |
| 2025/0262215 A1 | 8/2025 | Chung et al. |

FOREIGN PATENT DOCUMENTS

| | | |
|---|---|---|
| WO | WO 2019/173082 | 9/2019 |
| WO | WO 2020/210320 | 10/2020 |
| WO | WO 2021/097139 | 5/2021 |
| WO | WO 2021/127039 | 6/2021 |
| WO | WO 2021/127044 | 6/2021 |
| WO | WO 2021/127045 | 6/2021 |
| WO | WO 2021/127047 | 6/2021 |
| WO | WO 2021/231653 | 11/2021 |
| WO | WO 2021/242667 | 12/2021 |
| WO | WO 2021/252667 | 12/2021 |
| WO | WO 2022/136916 | 6/2022 |
| WO | WO 2022/221143 | 10/2022 |
| WO | WO 2022/251224 | 12/2022 |
| WO | WO 2022/271731 | 12/2022 |
| WO | WO 2023/064282 | 4/2023 |
| WO | WO 2023/076485 | 5/2023 |
| WO | WO 2023/114871 | 6/2023 |
| WO | WO 2023/114875 | 6/2023 |
| WO | WO 2023/114877 | 6/2023 |
| WO | WO 2024/031048 | 2/2024 |
| WO | WO 2024/059696 | 3/2024 |
| WO | WO 2024/059808 | 3/2024 |
| WO | WO 2024/102649 | 5/2024 |
| WO | WO 2024/102650 | 5/2024 |
| WO | WO 2024/249756 | 12/2024 |
| WO | WO 2025/076311 | 4/2025 |
| WO | WO 2025/106635 | 5/2025 |
| WO | WO 2025/179038 | 8/2025 |
| WO | WO 2025/184572 | 9/2025 |
| WO | WO 2025/188946 | 9/2025 |
| WO | WO 2025/193930 | 9/2025 |

OTHER PUBLICATIONS

Office Action dated Jan. 7, 2025 from JP Application No. 2023-501229, filed Jul. 8, 2021.
Office Action and Search Report dated Jan. 21, 2025 from TW Application No. 110125370, filed Jul. 9, 2021.
International Preliminary Report on Patentability issued Jan. 10, 2023 for PCT Application No. PCT/US2021/070851, filed Jul. 8, 2021.
Extended European Search Report dated Jun. 17, 2024 from EP Application No. 21838389.1, filed Jul. 8, 2021.
International Search Report and Written Opinion mailed Aug. 20, 2021 for PCT Application No. PCT/US2021/070851, filed Jul. 8, 2021.
Aaltonen, et al., "Solid form screening—A review" European Journal of Pharmaceutics and Biopharmaceutics (2009) 71(1):23-37.
Balbach et al., "Pharmaceutical evaluation of early development candidates 'The 100 mg approach'" Int. J. of Pharmaceutics (2004) 275:1-12.
Bastin et al., "Salt selection and Optimisation Procedures for Pharmaceutical New Chemical Entities", Organic Process Research & Development (2000) 4:427-435.
Berge et al., "Pharmaceutical Salts" J. Pharm. Sci (1977) 66(1):1-19.
Byrn et al., "Pharmaceutical Solids: A Strategic Approach to Regulatory Considerations" Pharmaceutical Research (1995) 12(7):945-954.
Caira, M. R., "Crystalline polymorphism of organic compounds" Topics in Current Chemistry, Springer Verlag Berlin Heidelberg, 1998, vol. 198, pp. 163-208.
Gupta et al., "Salts of Therapeutic Agents: Chemical, Physicochemical, and Biological Considerations" Molecules (2018) 23(7):1719 in 15 pages.
Mit'Kina et al., "Stress Studies and Photostability as a Part of Pharmaceutical Drug Development Data" The Bulletin of the Scientific Centre for Expert Evaluation of Medicinal Products. Moscow (2015) (2):9-12.
Rodríguez-Spong et al.: "General principles of pharmaceutical solid polymorphism: a supramolecular perspective" Adv. Drug Deliv. Rev. (2004) 56(3): 241-274.
Sarma et al., "Solid formation of pharmaceuticals: Polymorphs, salt and cocrystals" Korean J. Chem. Eng. (2011) 28(2):315-322.
Singhal et al., "Drug polymorphism and dosage form design: a practical perspective" Adv. Drug Delivery Reviews (2004) 56:335-347.
Examination Report dated Sep. 5, 2025 for AU Application No. 2021305347, filed Jul. 8, 2021.
Decision of Refusal dated May 13, 2025 from JP Application No. 2023-501229, filed Jul. 8, 2021.
Examination Report dated Jan. 24, 2025 for NZ Application No. 796125, filed Jul. 8, 2021.
Examination Report dated May 27, 2025 for NZ Application No. 796125, filed Jul. 8, 2021.
Examination Report dated Aug. 13, 2025 for NZ Application No. 796125, filed Jul. 8, 2021.
Office Action dated Jan. 23, 2025 from RU Application No. 2023100213, filed Jul. 8, 2021.

SALTS AND FORMS OF A WEE1 INHIBITOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57, including U.S. Provisional Application No. 63/049,996, filed Jul. 9, 2020.

FIELD

The present application relates to compounds, salts and salt forms that are WEE1 inhibitors and methods of using them to treat conditions characterized by excessive cellular proliferation, such as cancer.

BACKGROUND

WEE1 kinase plays a role in the G2-M cell-cycle checkpoint arrest for DNA repair before mitotic entry. Normal cells repair damaged DNA during G1 arrest. Cancer cells often have a deficient G1-S checkpoint and depend on a functional G2-M checkpoint for DNA repair. WEE1 is overexpressed in various cancer types.

SUMMARY

Some embodiments disclosed herein relate to a pharmaceutically acceptable salt of Compound A, wherein the pharmaceutically acceptable salt can be a salt selected from an adipate salt of Compound A, a HCl salt of Compound A, a sulfate salt of Compound A, a mesylate salt of Compound A, a maleate salt of Compound A, a phosphate salt of Compound A, a tartrate salt of Compound A, a tosylate salt of Compound A, a mucate salt of Compound A and a hippurate salt of Compound A. In some embodiments, the pharmaceutically acceptable salt can be a salt of Compound A selected from adipate salt Form A of Compound A, HCl salt Form A of Compound A, sulfate salt Form A of Compound A, mesylate salt Form A of Compound A, maleate salt Form A of Compound A, phosphate salt Form A of Compound A, tartrate salt Form A of Compound A, tosylate salt Form A of Compound A, mucate salt Form A of Compound A and hippurate salt Form A of Compound A. In other embodiments, the pharmaceutically acceptable salt can be HCl salt Form B of Compound A and/or sulfate salt Form B of Compound A. Other embodiments discloses herein relate to a freebase form of Compound A selected from freebase Form A of Compound A, freebase Form B of Compound A, freebase Form C of Compound A, freebase Form D of Compound A, freebase Form E of Compound A, freebase Form F of Compound A, freebase Form G of Compound A, freebase Form H of Compound A, freebase Form I of Compound A and freebase Form J of Compound A.

Other embodiments disclosed herein relate to a pharmaceutical composition that can include an effective amount of a pharmaceutically acceptable salt of Compound A, such as those described herein, and/or a freebase form of Compound A, including those described herein, and a pharmaceutically acceptable carrier, diluent, excipient or combination thereof.

Yet still other embodiments disclosed herein relate to a method of ameliorating or treating a malignant growth or tumor that includes administering to a subject in need thereof an effective amount of a pharmaceutically acceptable salt of Compound A, such as those described herein, and/or a freebase of Compound A, such as those described herein, or a pharmaceutical composition that can include an effective amount of a pharmaceutically acceptable salt of Compound A (including those described herein) and/or a freebase of Compound A, such as those described herein. Some embodiments disclosed herein relate to the use of a pharmaceutically acceptable salt of Compound A (such as those described herein) and/or a freebase of Compound A (such as those described herein), or a pharmaceutical composition that can include an effective amount of a pharmaceutically acceptable salt of Compound A (including those described herein) and/or a freebase of Compound A (including those described herein), for use in ameliorating or treating a malignant growth or tumor.

Other embodiments disclosed herein relate to the use of a pharmaceutically salt of Compound A (for example, an adipate salt of Compound A, a HCl salt of Compound A, a sulfate salt of Compound A, a mesylate salt of Compound A, a maleate salt of Compound A, a phosphate salt of Compound A, a tartrate salt of Compound A, a tosylate salt of Compound A, a mucate salt of Compound A and/or a hippurate salt of Compound A) and/or a freebase of Compound A (for example, freebase Form A of Compound A, freebase Form B of Compound A, freebase Form C of Compound A, freebase Form D of Compound A, freebase Form E of Compound A, freebase Form F of Compound A, freebase Form G of Compound A, freebase Form H of Compound A, freebase Form I of Compound A and/or freebase Form J of Compound A), or a pharmaceutical composition that can include an effective amount of a pharmaceutically salt of Compound A described herein and/or a freebase of Compound A described herein, for use in the manufacture of a medicament for ameliorating or treating a malignant growth or tumor.

In some embodiments, the malignant growth or tumor can be due to a cancer selected from a breast cancer, a cervical cancer, an ovarian cancer, an uterine cancer, a vaginal cancer, a vulvar cancer, a brain cancer, a cervicocerebral cancer, an esophageal cancer, a thyroid cancer, a small cell cancer, a non-small cell cancer, a lung cancer, a stomach cancer, a gallbladder/bile duct cancer, a liver cancer, a pancreatic cancer, a colon cancer, a rectal cancer, a choriocarcinoma, an uterus body cancer, an uterocervical cancer, a renal pelvis/ureter cancer, a bladder cancer, a prostate cancer, a penis cancer, a testicular cancer, a fetal cancer, a Wilms' cancer, a skin cancer, a malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma and a non-Hodgkin's lymphoma.

These and other embodiments are described in greater detail below.

DETAILED DESCRIPTION

Figure 1A:
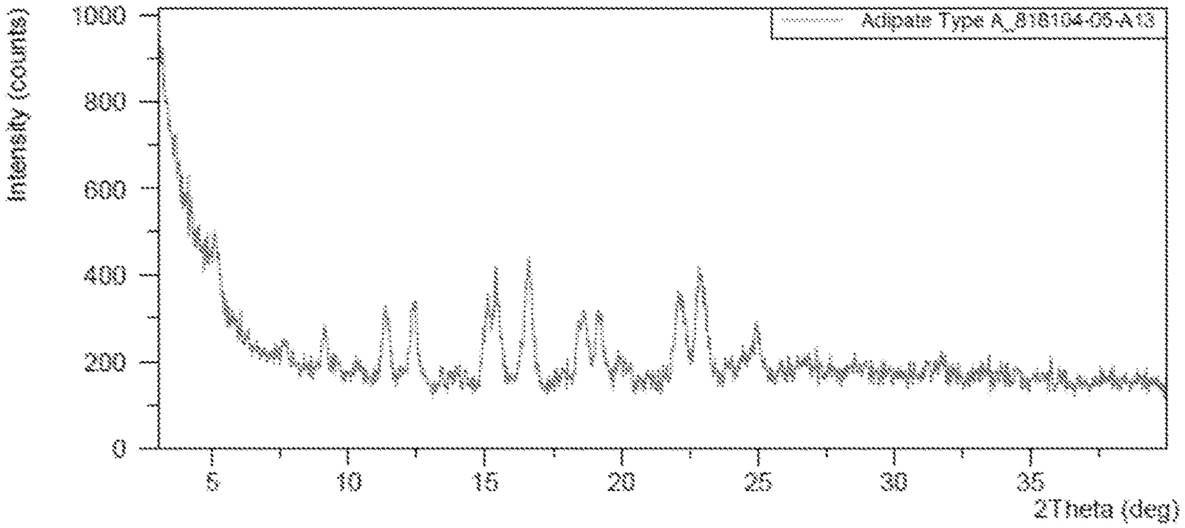
FIGS. 1A and 1B provide a representative XRPD pattern of adipate salt Form A.

WEE1 is a tyrosine kinase that is a critical component of the ATR-mediated G2 cell cycle checkpoint control that prevents entry into mitosis in response to cellular DNA damage. ATR phosphorylates and activates CHK1, which in turn activates WEE1, leading to the selective phosphorylation of cyclin-dependent kinase 1 (CDK1) at Tyr15, thereby stabilizing the CDK1-cyclin B complex and halting cell-cycle progression. This process confers a survival advantage by allowing tumor cells time to repair damaged DNA prior to entering mitosis. Inhibition of WEE1 abrogates the G2 checkpoint, promoting cancer cells with DNA damage to enter into unscheduled mitosis and undergo cell death via mitotic catastrophe. Therefore, WEE1 inhibition has the potential to sensitize tumors to DNA-damaging agents, such as cisplatin, and to induce tumor cell death.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Unless otherwise specified, the term "crystalline" and related terms used herein, when used to describe a substance, component, product or form, mean that the substance, component, product or form is substantially crystalline, for example, as determined by X-ray diffraction. (see, e.g., *Remington's Pharmaceutical Sciences,* 20$^{th}$ed., Lippincott Williams & Wilkins, Philadelphia Pa., 173 (2000); *The United States Pharmacopeia,* 37$^{th}$ed., 503-509 (2014)).

As used herein, and unless otherwise specified, the terms "about" and "approximately," when used in connection with doses, amounts or weight percents of ingredients of a composition or a dosage form, mean a dose, amount or weight percent that is recognized by one of ordinary skill in the art to provide a pharmacological effect equivalent to that obtained from the specified dose, amount, or weight percent. In some embodiments, the terms "about" and "approximately," when used in this context, contemplate a dose, amount, or weight percent within 30%, within 20%, within 15%, within 10%, or within 5%, of the specified dose, amount or weight percent.

As used herein, and unless otherwise specified, the terms "about" and "approximately," when used in connection with a numeric value or range of values which is provided to characterize a particular solid form, e.g., a specific temperature or temperature range (for example, that describes a melting, dehydration, desolvation or glass transition temperature); a mass change (for example, a mass change as a function of temperature or humidity); a solvent or water content (for example, mass or a percentage); or a peak position (for example, in analysis by, for example, IR or Raman spectroscopy or XRPD); indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies and dissolution studies. In some embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.2 degrees two theta (° 2θ), or more. For example, in some embodiments, the value of an XRPD peak position may vary by up to ±0.2 degrees 2θ while still describing the particular XRPD peak.

As used herein, and unless otherwise specified, a solid form that is "substantially physically pure" is substantially free from other solid forms. In some embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In some embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, In some embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

As used herein, (R)-2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one is Compound A, which has the structure:

Compound A

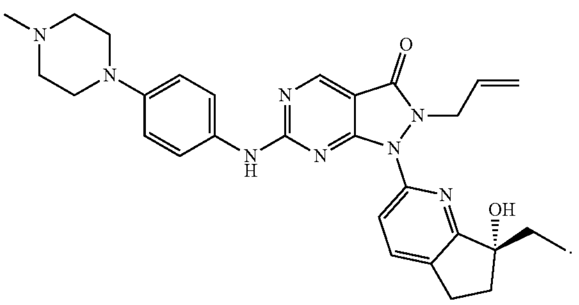

Compound A is also referred to herein as the "freebase of Compound A." If there is an inconsistency between the name of Compound A and a structure of Compound A provided herein, then the structure of Compound A in this paragraph is what is meant for Compound A.

A variety of polymorphs of Compound A can be obtained. Some embodiments disclosed herein relate to freebase Form A of Compound A. Some embodiments disclosed herein relate to freebase Form B of Compound A. Other embodiments disclosed herein relate to freebase Form C of Compound A. Still other embodiments disclosed herein relate to freebase Form D of Compound A. Yet still other embodiments disclosed herein relate to freebase Form E of Compound A. Some embodiments disclosed herein relate to freebase Form F of Compound A. Other embodiments disclosed herein relate to freebase Form G of Compound A. Still other embodiments disclosed herein relate to freebase Form H of Compound A. Yet still other embodiments disclosed herein relate to freebase Form I of Compound A. Some embodiments disclosed herein relate to freebase Form J of Compound A.

In some embodiments, a freebase described herein can further include one or more other polymorph forms. For example, freebase Form A may further include freebase Form F and/or one of more of other freebase forms. In some embodiments, freebase Form C may further include freebase Form F and/or one of more of other freebase forms. In some embodiments, freebase Form D may further include freebase Form F and/or one of more of other freebase forms. In some embodiments, freebase Form G may further include freebase Form F and/or one of more of other freebase forms. In some embodiments, freebase Form H may further include freebase Form F and/or one of more of other freebase forms. In some embodiments, freebase Form B may further include freebase Form E and/or one of more of other freebase forms. In some embodiments, freebase Form E may further include freebase Form J and/or one of more of other freebase forms. In some embodiments, freebase Form J may further include freebase Form E and/or one or more of other freebase forms. In some embodiments, freebase Form B may further include freebase Form J and/or one of more of other freebase forms.

In a freebase form of Compound A, various amounts of freebase forms of Compound A can be present. For example, the amount of freebase of Compound A that can be present in Form E can be in the range of about 90% to 100%. In some embodiments, the amount of freebase of Compound A that can be present in Form E can be in the range of about 95% to 100%. In other embodiments, the amount of freebase of Compound A that can be present in Form E can be in the range of about 98% to 100%. In still other embodiments, the amount of freebase of Compound A that can be present in Form E can be in the range of about 95% to 98%. In some embodiments, the amount of freebase of Compound A that can be present in Form E can be ≥90%. In other embodiments, the amount of freebase of Compound A that can be present in Form E can be ≥95%. In still other embodiments, the amount of freebase of Compound A that can be present in Form E can be ≥98%. In some embodiments, the amount of freebase of Compound A that can be present in Form J can be in the range of about 90% to 100%. In some embodiments, the amount of freebase of Compound A that can be present in Form J can be in the range of about 95% to 100%. In other embodiments, the amount of freebase of Compound A that can be present in Form J can be in the range of about 98% to 100%. In still other embodiments, the amount of freebase of Compound A that can be present in Form J can be in the range of about 95% to 98%. In some embodiments, the amount of freebase of Compound A that can be present in Form J can be ≥90%. In other embodiments, the amount of freebase of Compound A that can be present in Form J can be ≥95%. In still other embodiments, the amount of freebase of Compound A that can be present in Form J can be ≥98%. When less than 100% of a freebase form described herein (such as Form E and Form J) is the freebase of Compound A, one or more of the components selected from the following can be present in the freebase form (such as Form E and Form J): (1) a compound that is the result of the degradation of the freebase of Compound A, and (2) an impurity from the synthesis of the freebase of Compound A.

A variety of salts of Compound A were obtained. Additionally, a variety of salt forms of Compound A are provided herein. For example, some embodiments disclosed herein relate to adipate salt Form A of Compound A. Other embodiments disclosed herein relate to HCl salt Form A of Compound A. Still other embodiments disclosed herein relate to sulfate salt Form A of Compound A. Yet still other embodiments disclosed herein relate to mesylate salt Form A of Compound A. Some embodiments disclosed herein relate to maleate salt Form A of Compound A. Other embodiments disclosed herein relate to phosphate salt Form A of Compound A. Still other embodiments disclosed herein relate to tartrate salt Form A of Compound A. Yet still other embodiments disclosed herein relate to tosylate salt Form A of Compound A. Some embodiments disclosed herein relate to mucate salt Form A of Compound A. Still other embodiments disclosed herein relate to hippurate salt Form A of Compound A. Some embodiments disclosed herein relate to HCl salt Form B of Compound A. In other embodiments disclosed herein related to sulfate salt Form B of Compound A.

Some embodiments disclosed herein relate to a pharmaceutically acceptable salt of Compound A, wherein the pharmaceutically acceptable salt can be an adipate salt. Those skilled in the art understand that the adipate salt of Compound A has a single molecule of Compound A for a single molecule of adipate. In some embodiments, the molar ratio of adipic acid to Compound A may be from about 0.6 to about 1.4, from about 0.8 to about 1.2, from about 0.9 to about 1.1 or about 1.

A variety of adipate salt forms of Compound A can be obtained. In some embodiments, an adipate salt form can be adipate salt Form A. In some embodiments, an adipate salt form described herein can further include a freebase form of Compound A. For example, adipate salt Form A may further include a small amount of a freebase of Compound A. In some embodiments, an adipate salt form described herein can further include a small amount of one or more other adipate salt forms, such as those described herein.

In a salt form of Compound A, various amounts of the adipate salt form of Compound A can be present. For example, the amount of adipate salt of Compound A that can be present in adipate salt Form A can be in the range of about 90% to 100%. In some embodiments, the amount of adipate salt of Compound A that can be present in adipate salt Form A can be in the range of about 95% to 100%. In other embodiments, the amount of adipate salt of Compound A that can be present in adipate salt Form A can be in the range of about 98% to 100%. In still other embodiments, the amount of adipate salt of Compound A that can be present in adipate salt Form A can be in the range of about 95% to 98%. In some embodiments, the amount of adipate salt of Compound A that can be present in adipate salt Form A can be ≥90%. In other embodiments, the amount of adipate salt of Compound A that can be present in adipate salt Form A can be ≥95%. In still other embodiments, the amount of adipate salt of Compound A that can be present in adipate salt Form A can be ≥98%. When less than 100% of a salt form described herein is an adipate salt form of Compound A, one or more of the components selected from the following can be present in the adipate salt form of Compound A (such as adipate salt Form A of Compound A): (1) a freebase of Compound A (such as those described herein), (2) a compound that is the result of the degradation of an adipate salt form of Compound A and/or the degradation of a freebase of Compound A, and (3) an impurity from the synthesis of an adipate salt form of Compound A and/or the synthesis of a freebase of Compound A.

Various methods can be used to characterize forms and salts of Compound A described herein. For example, X-ray powder diffraction (XRPD), differential scanning calorimetry (DSC), thermal gravimetric analysis (TGA), $^{1}H$ NMR and $^{13}C$ NMR. All XRPD peaks and spectra provided herein are measured on a degrees 2-Theta scale (2θ).

In some embodiments, adipate salt Form A can be characterized by one or more peaks in an XRPD pattern, wherein the one or more peaks can be selected from a peak in the range from about 12.2 degrees to about 12.5 degrees, a peak in the range from about 14.9 degrees to about 15.2 degrees, a peak in the range of from about 15.3 degrees to about 15.6 degrees, a peak in the range from about 16.4 degrees to about 16.7 degrees, a peak in the range from about 22.0 degrees to about 22.3 degrees and a peak in the range from about 22.7 degrees to about 23.0 degrees. In some embodiments, adipate salt Form A can be characterized by one or more peaks in an XRPD pattern, wherein the one or more peaks is selected from a peak in the range of from about 5.0 degrees to about 5.3 degrees, a peak in the range from about 9.0 degrees to about 9.3 degrees, a peak in the range from about 11.2 degrees to about 11.5 degrees, a peak in the range from about 12.2 degrees to about 12.5 degrees, a peak in the range from about 14.9 degrees to about 15.2 degrees, a peak in the range of from about 15.3 degrees to about 15.6 degrees, a peak in the range from about 16.4 degrees to about 16.7 degrees, a peak in the range from about 18.4 degrees to about 18.7 degrees, a peak in the range from about 19.0 degrees to about 19.3 degrees, a peak in the range from about 22.0 degrees to about 22.3 degrees, a peak in the range from about 22.7 degrees to about 23.0 degrees and a peak in the range from about 24.8 degrees to about 25.1 degrees.

In some embodiments, adipate salt Form A can be characterized by one or more peaks in an XPRD pattern, wherein the one or more peaks can be selected from about 12.38 degrees, about 15.09 degrees, about 15.40 degrees, about 16.58 degrees, about 22.12 degrees and about 22.88 degrees. In some embodiments, adipate salt Form A can be characterized by one or more peaks in an XRPD pattern, wherein the one or more peaks is selected from about 11.36 degrees, about 12.38 degrees, about 15.09 degrees, about 15.40 degrees, about 16.58 degrees, about 18.57 degrees, about 19.17 degrees, about 22.12 degrees and about 22.88 degrees. In some embodiments, adipate salt Form A can be characterized by one or more peaks in an XRPD pattern, wherein the one or more peaks is selected from about 5.14 degrees, about 9.11 degrees, about 11.36 degrees, about 12.38 degrees, about 15.09 degrees, about 15.40 degrees, about 16.58 degrees, about 18.57 degrees, about 19.17 degrees, about 22.12 degrees, about 22.88 degrees and about 24.92 degrees.

Figure 1B:
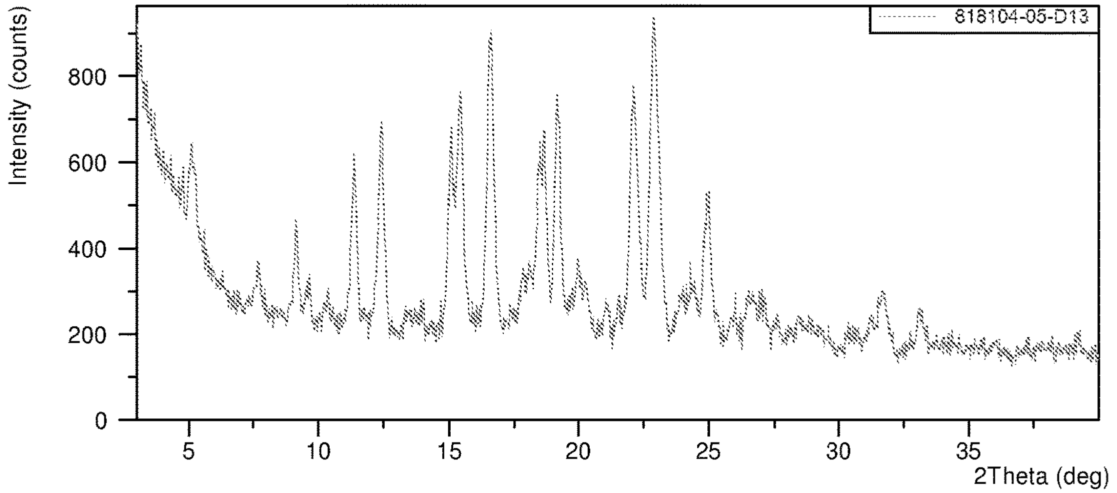

In some embodiments, adipate salt Form A can exhibit an XRPD pattern as shown in FIGS. 1A and 1B.

In some embodiments, adipate salt Form A can be characterized by one or more peaks in an XRPD pattern selected from:

| Peak | 2θ | Relative Intensity [%] |
|---|---|---|
| 1 | 5.14 | 30.55 |
| 2 | 9.11 | 31.32 |
| 3 | 11.36 | 51.29 |
| 4 | 12.38 | 60.16 |
| 5 | 15.09 | 66.20 |
| 6 | 15.40 | 84.75 |
| 7 | 16.58 | 100.00 |
| 8 | 18.57 | 54.12 |
| 9 | 19.17 | 52.06 |
| 10 | 22.12 | 66.27 |
| 11 | 22.88 | 79.12 |
| 12 | 24.92 | 36.29 |

Figure 2:
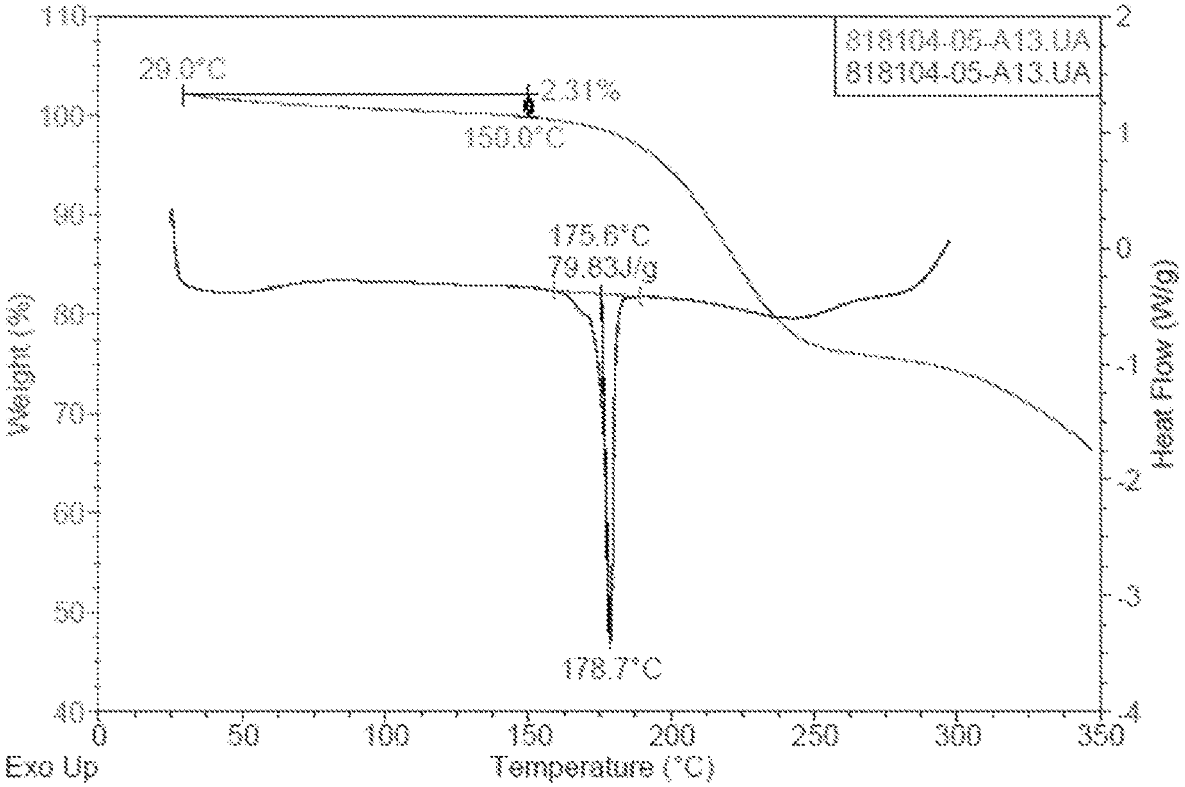
FIG. 2 provides a representative DSC and TGA thermogram of adipate salt Form A.

Adipate salt Form A can also be characterized by DSC and/or thermogravimetric analysis thermogram (TGA). In some embodiments, adipate salt Form A can be characterized by a DSC and/or a TGA thermogram of FIG. 2. In some embodiments, adipate salt Form A can be characterized by a weight loss of about 2.3% when heated from about 29° C. to about 150° C. In some embodiments, adipate salt Form A can be characterized by an endotherm in the range of about 175° C. to about 183° C. In some embodiments, adipate salt Form A can be characterized by an endotherm in the range of about 177° C. to about 182° C. In some embodiments, adipate salt Form A can be characterized by an endotherm at about 178.7° C.

In some embodiments, adipate salt Form A can be obtained by solution crystallization, and can be characterized by an endotherm at about 179.9° C. The purity of such compound is about 98.9%. In some embodiments, adipate salt Form A can be an anhydrate.

Some embodiments disclosed herein relate to a pharmaceutically acceptable salt of Compound A, wherein the pharmaceutically acceptable salt can be a HCl salt. A variety of HCl salt forms of Compound A can be obtained. In some embodiments, a HCl salt form can be HCl salt Form A. In some embodiments, a HCl salt form can be HCl salt Form B. In some embodiments, a HCl salt form described herein can further include a freebase of Compound A. For example, HCl salt Form A may further include a small amount of freebase Form A. In some embodiments, a HCl salt form described herein can further include a small amount of one or more other HCl salt forms, such as those described herein. For example, HCl salt Form A may further include a small amount of HCl salt Form B.

In some embodiments, HCl salt Form A can be obtained via slurry of about one equivalent of Compound A with about one equivalent of HCl. In some embodiments, HCl salt Form B can be obtained via slurry of about one equivalent of Compound A with about two equivalents of HCl. In some embodiments, the molar ratio of HCl to Compound A can be from about 0.6 to about 1.4, from about 0.8 to about 1.2, from about 0.9 to about 1.1 or about 1. In some embodiments, the molar ratio of HCl to Compound A can be from about 1.2 to about 2.8, from about 1.6 to about 2.4, from about 1.8 to about 2.2 or about 2.

In a salt form of Compound A, various amounts of a HCl salt form of Compound A can be present. For example, the amount of HCl salt of Compound A that can be present in HCl salt Form A can be in the range of about 90% to 100%. In some embodiments, the amount of HCl salt of Compound A that can be present in HCl salt Form A can be in the range of about 95% to 100%. In other embodiments, the amount of HCl salt of Compound A that can be present in HCl salt Form A can be in the range of about 98% to 100%. In still other embodiments, the amount of HCl salt of Compound A that can be present in HCl salt Form A can be in the range of about 95% to 98%. In some embodiments, the amount of HCl salt of Compound A that can be present in HCl salt Form A can be ≥90%. In other embodiments, the amount of HCl salt of Compound A that can be present in HCl salt Form A can be ≥95%. In still other embodiments, the amount of HCl salt of Compound A that can be present in HCl salt Form A can be ≥98%. When less than 100% of a salt form described herein is a HCl salt form of Compound A, one or more of the components selected from the following can be present in the HCl salt form of Compound A (such as HCl salt Form A of Compound A): (1) a freebase of Compound A (such as those described herein), (2) a compound that is the result of the degradation of a HCl salt form of Compound A and/or the degradation of a freebase of Compound A, and (3) an impurity from the synthesis of a HCl salt form of Compound A and/or the synthesis of a freebase of Compound A.

In some embodiments, HCl salt Form A can be characterized by one or more peaks in an XRPD pattern, wherein the one or more peaks can be selected from a peak in the range of about 3.4 degrees to about 3.8 degrees, a peak in the range of about 6.1 degrees to about 6.5 degrees, a peak in the range of about 8.5 degrees to about 8.9 degrees, a peak in the range of about 10.5 degrees to about 10.9 degrees, a peak in the range of about 12 degrees to about 12.4 degrees and a peak in the range of about 17.6 degrees to about 18 degrees. In some embodiments, HCl salt Form A can be characterized by one or more peaks in an XRPD pattern, wherein the one or more peaks is selected from a peak in the range of about 3.4 degrees to about 3.8 degrees, a peak in the range of about 6.1 degrees to about 6.5 degrees, a peak in the range of about 8.5 degrees to about 8.9 degrees, a peak in the range of about 9 degrees to about 9.4 degrees, a peak in the range of about 9.8 degrees to about 10.2 degrees, a peak in the range of about 10.5 degrees to about 10.9 degrees, a peak in the range of about 11.1 degrees to about 11.5 degrees, a peak in the range of about 11.7 degrees to about 12.1 degrees, a peak in the range of about 12 degrees to about 12.4 degrees, a peak in the range of about 12.2 degrees to about 12.6 degrees, a peak in the range of about 13 degrees to about 13.4 degrees, a peak in the range of about 14.2 degrees to about 14.6 degrees, a peak in the range of about 15.5 degrees to about 15.9 degrees, a peak in the range of about 15.9 degrees to about 16.3 degrees, a peak in the range of about 16.9 degrees to about 17.3 degrees, a peak in the range of about 17.6 degrees to about 18 degrees, a peak in the range of about 18.9 degrees to about 19.3 degrees, a peak in the range of about 19.3 degrees to about 19.7 degrees, a peak in the range of about 20.2 degrees to about 20.6 degrees, a peak in the range of about 21.6 degrees to about 22 degrees, a peak in the range of about 22.6 degrees to about 23 degrees, a peak in the range of about 23.4 degrees to about 23.8 degrees, a peak in the range of about 24.1 degrees to about 24.5 degrees, a peak in the range of about 24.8 degrees to about 25.2 degrees, a peak in the range of about 25.8 degrees to about 26.2 degrees and a peak in the range of about 26.3 degrees to about 26.7 degrees.

In some embodiments, HCl salt Form A can be characterized by one or more peaks in an XPRD pattern, wherein the one or more peaks can be selected from about 3.61 degrees, about 6.25 degrees, about 8.69 degrees, about 10.65 degrees, about 12.16 degrees and about 17.81 degrees. In some embodiments, HCl salt Form A can be characterized by one or more peaks in an XRPD pattern, wherein the one or more peaks is selected from about 3.61 degrees, about 6.25 degrees, about 8.69 degrees, about 9.23 degrees, about 9.98 degrees, about 10.65 degrees, about 11.30 degrees, about 11.87 degrees, about 12.16 degrees, about 12.41 degrees, about 13.21 degrees, about 14.35 degrees, about 15.68 degrees, about 16.05 degrees, about 17.08 degrees, about 17.81 degrees, about 19.06 degrees, about 19.49 degrees, about 20.37 degrees, about 21.77 degrees, about 22.82 degrees, about 23.59 degrees, about 24.30 degrees, about 24.99 degrees, about 25.97 degrees and about 26.47 degrees.

In some embodiments, HCl salt Form A can be characterized by one or more peaks in an XRPD pattern selected from:

| Peak | 2θ | Relative Intensity [%] |
|---|---|---|
| 1 | 3.61 | 58.71 |
| 2 | 6.25 | 100.00 |
| 3 | 8.69 | 73.28 |
| 4 | 9.23 | 20.22 |
| 5 | 9.98 | 19.13 |
| 6 | 10.65 | 28.84 |
| 7 | 11.30 | 11.97 |
| 8 | 11.87 | 17.22 |
| 9 | 12.16 | 28.63 |

-continued

| Peak | 2θ | Relative Intensity [%] |
|---|---|---|
| 10 | 12.41 | 23.59 |
| 11 | 13.21 | 21.44 |
| 12 | 14.35 | 20.75 |
| 13 | 15.68 | 21.52 |
| 14 | 16.05 | 17.99 |
| 15 | 17.08 | 19.89 |
| 16 | 17.81 | 33.27 |
| 17 | 19.06 | 21.99 |
| 18 | 19.49 | 22.53 |
| 19 | 20.37 | 17.97 |
| 20 | 21.77 | 13.38 |
| 21 | 22.82 | 14.64 |
| 22 | 23.59 | 12.02 |
| 23 | 24.30 | 21.68 |
| 24 | 24.99 | 10.17 |
| 25 | 25.97 | 19.61 |
| 26 | 26.47 | 12.89 |
| 27 | 27.68 | 7.70 |
| 28 | 29.25 | 6.63 |
| 29 | 31.60 | 5.50 |

In some embodiments, HCl salt Form B can be characterized by one or more peaks in an XRPD pattern, wherein the one or more peaks can be selected from a peak in the range of about 3.1 degrees to about 3.5 degrees, a peak in the range of about 5.7 degrees to about 6.1 degrees, a peak in the range of about 6.9 degrees to about 7.3 degrees, a peak in the range of about 8.0 degrees to about 8.4 degrees, a peak in the range of about 10.6 degrees to about 11.0 degrees, a peak in the range of about 14.1 degrees to about 14.5 degrees, a peak in the range of about 18.8 degrees to about 19.2 degrees, a peak in the range of about 25.5 degrees to about 25.9 degrees and a peak in the range of about 26.5 degrees to about 26.9 degrees. In some embodiments, HCl salt Form B can be characterized by one or more peaks in an XRPD pattern, wherein the one or more peaks is selected from a peak in the range of about 3.1 degrees to about 3.5 degrees, a peak in the range of about 5.7 degrees to about 6.1 degrees, a peak in the range of about 6.9 degrees to about 7.3 degrees, a peak in the range of about 8.0 degrees to about 8.4 degrees, a peak in the range of about 10.6 degrees to about 11.0 degrees, a peak in the range of about 13.6 degrees to about 14.0 degrees, a peak in the range of about 14.1 degrees to about 14.5 degrees, a peak in the range of about 16.0 degrees to about 16.4 degrees, a peak in the range of about 17.1 degrees to about 17.5 degrees, a peak in the range of about 18.8 degrees to about 19.2 degrees, a peak in the range of about 25.5 degrees to about 25.9 degrees and a peak in the range of about 26.5 degrees to about 26.9 degrees.

In some embodiments, HCl salt Form B can be characterized by one or more peaks in an XPRD pattern, wherein the one or more peaks can be selected from about 3.30 degrees, about 5.87 degrees, about 7.14 degrees, about 8.19 degrees, about 10.80 degrees, about 14.33 degrees, about 18.99 degrees, about 25.66 degrees and about 26.69 degrees. In some embodiments, HCl salt Form B can be characterized by one or more peaks in an XRPD pattern, wherein the one or more peaks is selected from about 3.30 degrees, about 5.87 degrees, about 7.14 degrees, about 8.19 degrees, about 10.80 degrees, about 13.78 degrees, about 14.33 degrees, about 16.16 degrees, about 17.25 degrees, about 18.99 degrees, about 25.66 degrees and about 26.69 degrees.

In some embodiments, HCl salt Form B can be characterized by one or more peaks in an XRPD pattern selected from:

| Peak | 2θ | Relative Intensity [%] |
|---|---|---|
| 1 | 3.30 | 90.30 |
| 2 | 5.87 | 92.08 |
| 3 | 7.14 | 100.00 |
| 4 | 8.19 | 27.64 |
| 5 | 10.80 | 31.78 |
| 6 | 13.78 | 13.70 |
| 7 | 14.33 | 26.89 |
| 8 | 16.16 | 19.04 |
| 9 | 17.25 | 22.09 |
| 10 | 18.99 | 26.30 |
| 11 | 25.66 | 43.30 |
| 12 | 26.69 | 37.13 |

Figure 3:
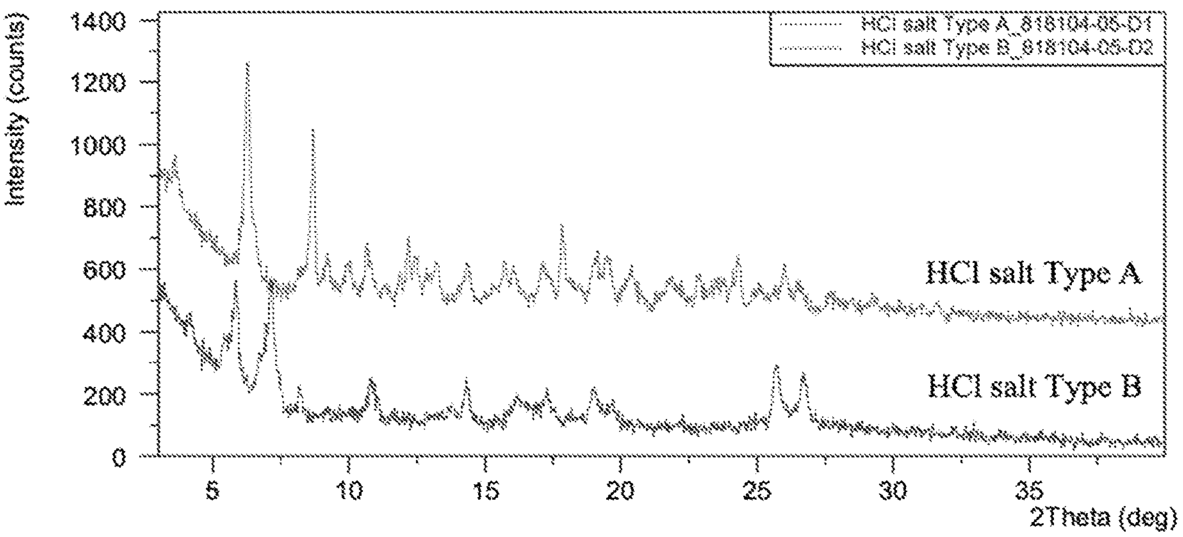
FIG. 3 provides a representative XRPD pattern of HCl salt Form A and HCl salt Form B.

In some embodiments, HCl salt Form A and HCl salt Form B can exhibit an XRPD pattern as shown in FIG. 3.

Figure 4:
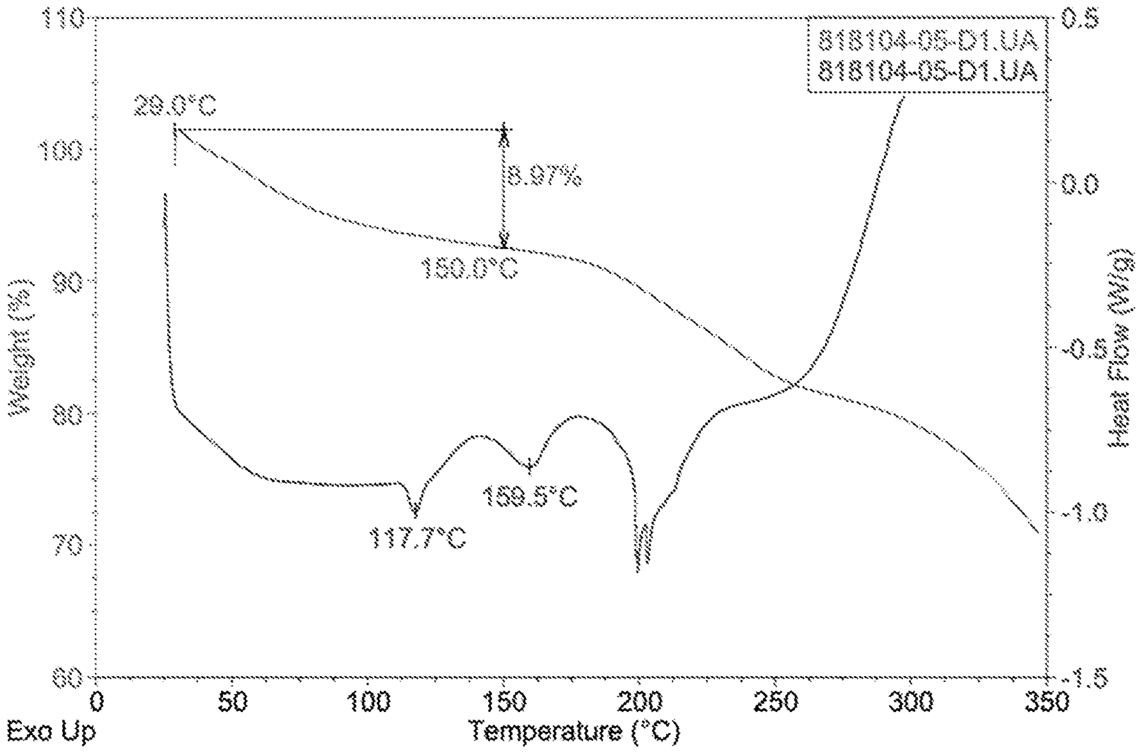
FIG. 4 provides a representative DSC and TGA thermogram of HCl salt Form A.

HCl salt Form A can be characterized by DSC and/or TGA. In some embodiments, HCl salt Form A can be characterized by a DSC and/or TGA thermogram of FIG. 4. In some embodiments, HCl salt Form A can be characterized by a weight loss of about 9.0% when heated from about 29° C. to about 150° C. In some embodiments, a HCl salt Form A can be characterized by a first endotherm in the range of about 114° C. to about 122° C. and a second endotherm in the range of about 156° C. to about 164° C. In some embodiments, HCl salt Form A can be characterized by a first endotherm in the range of about 115° C. to about 121° C. and a second endotherm in the range of about 157° C. to about 163° C. In some embodiments, HCl salt Form A can be characterized by a first endotherm at about 117.7° C. and a second endotherm at about 159.5° C.

Figure 5:
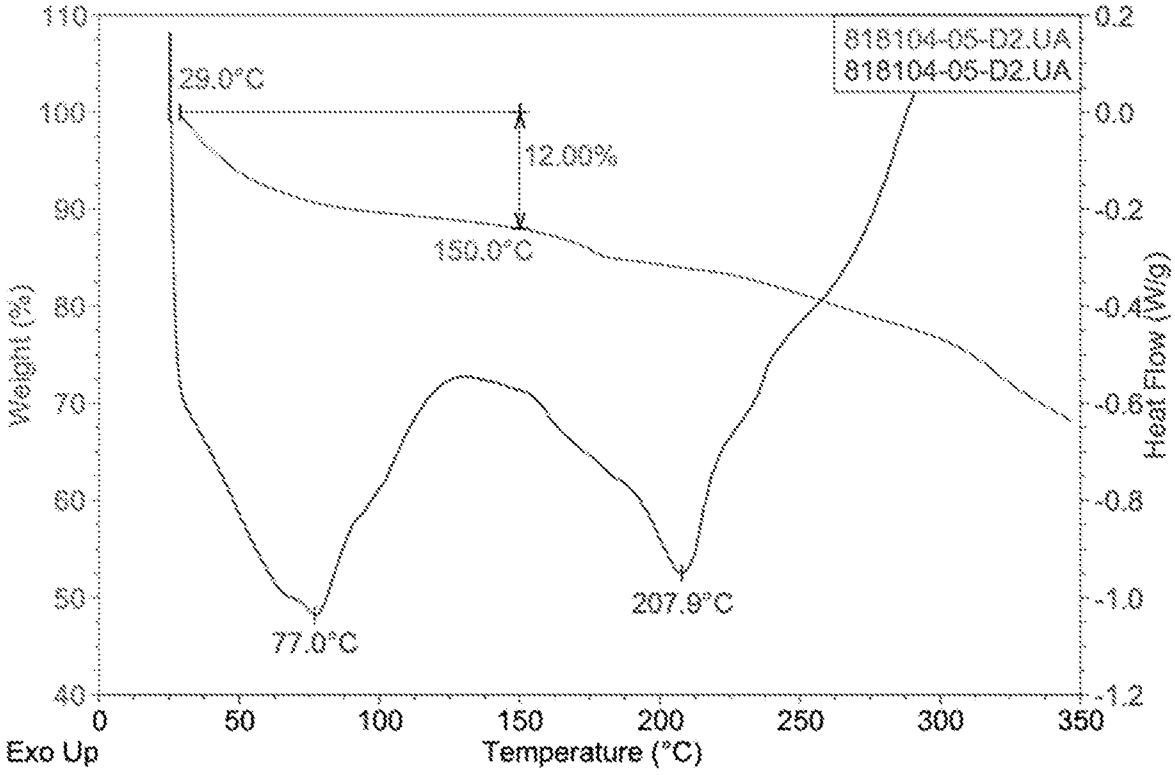
FIG. 5 provides a representative DSC and TGA thermogram of HCl salt Form B.

HCl salt Form B can also be characterized by DSC and/or TGA. In some embodiments, HCl salt Form B can be characterized by a DSC and/or TGA thermogram of FIG. 5. In some embodiments, HCl salt Form B can be characterized by a weight loss of about 12.0% when heated from about 29° C. to about 150° C. In some embodiments, HCl salt Form B can be characterized by a first endotherm in the range of about 73° C. to about 81° C. and a second endotherm in the range of about 204° C. to about 212° C. In some embodiments, HCl salt Form B can be characterized by a first endotherm in the range of about 74° C. to about 80° C. and a second endotherm in the range of about 205° C. to about 211° C. In some embodiments, HCl salt Form B can be characterized by a first endotherm at about 77.0° C. and a second endotherm at about 207.9° C.

Some embodiments disclosed herein relate to a pharmaceutically acceptable salt of Compound A, wherein the pharmaceutically acceptable salt can be a sulfate salt. A variety of sulfate salt forms of Compound A can be obtained. In some embodiments, a sulfate salt form can be sulfate salt Form A. In some embodiments, a sulfate salt form can be sulfate salt Form B. In some embodiments, a sulfate salt form described herein can further include a freebase of Compound A. For example, sulfate salt Form A may further include a small amount of freebase Form A. In some embodiments, a sulfate salt form described herein can further include a small amount of one or more other sulfate salt forms, such as those described herein. For example, sulfate salt Form A may further include a small amount of sulfate salt Form B. In some embodiments, the molar ratio of sulfate to Compound A may be from about 0.6 to about 1.4, from about 0.8 to about 1.2, from about 0.9 to about 1.1 or about 1.

In a salt form of Compound A, various amounts of the sulfate salt form of Compound A can be present. For example, the amount of sulfate salt of Compound A that can be present in sulfate salt Form A can be in the range of about 90% to 100%. In some embodiments, the amount of sulfate salt of Compound A that can be present in sulfate salt Form A can be in the range of about 95% to 100%. In other embodiments, the amount of sulfate salt of Compound A that can be present in sulfate salt Form A can be in the range of about 98% to 100%. In still other embodiments, the amount of sulfate salt of Compound A that can be present in sulfate salt Form A can be in the range of about 95% to 98%. In some embodiments, the amount of sulfate salt of Compound A that can be present in sulfate salt Form A can be ≥90%. In other embodiments, the amount of sulfate salt of Compound A that can be present in sulfate salt Form A can be ≥95%. In still other embodiments, the amount of sulfate salt of Compound A that can be present in sulfate salt Form A can be ≥98%. When less than 100% of a salt form described herein is a sulfate salt form of Compound A, one or more of the components selected from the following can be present in the sulfate salt form of Compound A (such as sulfate salt Form A of Compound A): (1) a freebase of Compound A (such as those described herein), (2) a compound that is the result of the degradation of a sulfate salt form of Compound A and/or the degradation of a freebase of Compound A, and (3) an impurity from the synthesis of a sulfate salt form of Compound A and/or the synthesis of a freebase of Compound A.

In some embodiments, sulfate salt Form A can be characterized by one or more peaks in an XRPD pattern, wherein the one or more peaks can be selected from a peak in the range of about 7.9 degrees to about 8.3 degrees, a peak in the range of about 11.2 degrees to about 11.6 degrees, a peak in the range of about 15.9 degrees to about 16.3 degrees, a peak in the range of about 16.1 degrees to about 16.5 degrees, a peak in the range of about 17.7 degrees to about 18.1 degrees and a peak in the range of about 23.7 degrees to about 24.1 degrees. In some embodiments, sulfate salt Form A can be characterized by one or more peaks in an XRPD pattern, wherein the one or more peaks is selected from a peak in the range of about 7.9 degrees to about 8.3 degrees, a peak in the range of about 8.6 degrees to about 9 degrees, a peak in the range of about 11.2 degrees to about 11.6 degrees, a peak in the range of about 15.9 degrees to about 16.3 degrees, a peak in the range of about 16.1 degrees to about 16.5 degrees, a peak in the range of about 17.7 degrees to about 18.1 degrees, a peak in the range of about 19.9 degrees to about 20.3 degrees, a peak in the range of about 23.7 degrees to about 24.1 degrees, a peak in the range of about 24 degrees to about 24.4 degrees and a peak in the range of about 24.9 degrees to about 25.3 degrees.

In some embodiments, sulfate salt Form A can be characterized by one or more peaks in an XPRD pattern, wherein the one or more peaks can be selected from about 8.07 degrees, about 11.37 degrees, about 16.11 degrees, about 16.33 degrees, about 17.92 degrees and about 23.87 degrees. In some embodiments, sulfate salt Form A can be characterized by one or more peaks in an XRPD pattern, wherein the one or more peaks is selected from about 8.07 degrees, about 8.84 degrees, about 11.37 degrees, about 16.11 degrees, about 16.33 degrees, about 17.92 degrees, about 20.08 degrees, about 23.87 degrees, about 24.24 degrees and about 25.13 degrees.

Figure 6:
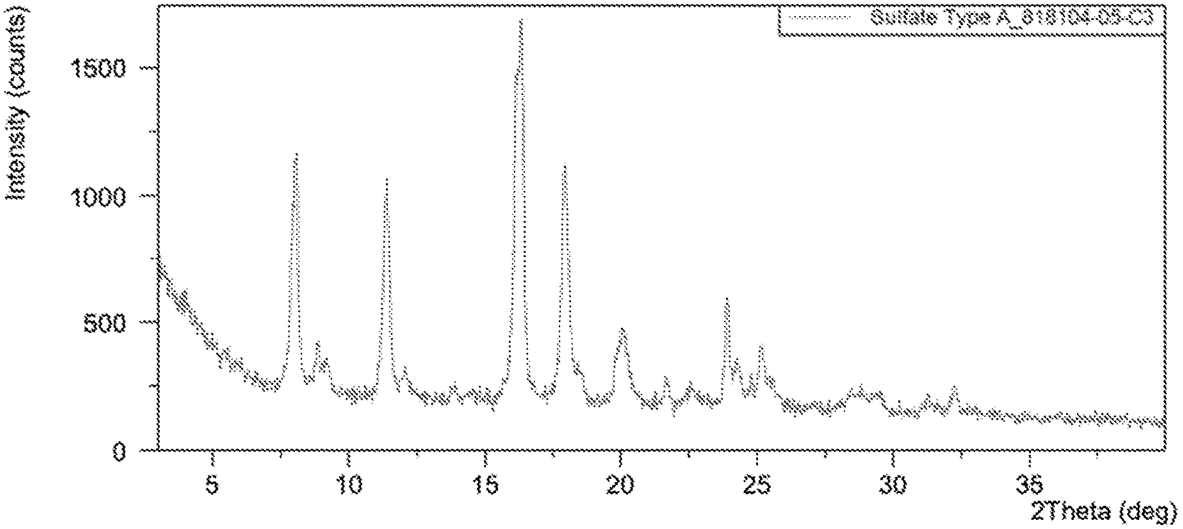
FIG. 6 provides a representative XRPD pattern of sulfate salt Form A.

In some embodiments, sulfate salt Form A can exhibit an XRPD pattern as shown in FIG. 6.

In some embodiments, sulfate salt Form A can be characterized by one or more peaks in an XRPD pattern selected from:

| Peak | 2θ | Relative Intensity [%] |
|---|---|---|
| 1 | 8.07 | 60.21 |
| 2 | 8.84 | 11.45 |
| 3 | 9.22 | 7.49 |
| 4 | 11.37 | 57.24 |
| 5 | 12.07 | 6.52 |
| 6 | 13.83 | 2.25 |
| 7 | 16.11 | 82.69 |
| 8 | 16.33 | 100.00 |
| 9 | 17.92 | 63.07 |
| 10 | 18.51 | 8.06 |
| 11 | 20.08 | 19.22 |
| 12 | 21.63 | 6.18 |
| 13 | 22.55 | 4.50 |
| 14 | 23.87 | 27.21 |
| 15 | 24.24 | 11.74 |
| 16 | 25.13 | 15.90 |
| 17 | 28.42 | 4.94 |
| 18 | 29.45 | 4.16 |
| 19 | 31.21 | 2.90 |
| 20 | 32.28 | 6.13 |
| 21 | 36.02 | 0.72 |

In some embodiments, sulfate salt Form B can be characterized by one or more peaks in an XRPD pattern, wherein the one or more peaks can be selected from a peak in the range of about 4.3 degrees to about 4.7 degrees, a peak in the range of about 7.7 degrees to about 8.1 degrees, a peak in the range of about 8.8 degrees to about 9.2 degrees, a peak in the range of about 11.3 degrees to about 11.7 degrees, a peak in the range of about 11.8 degrees to about 12.2 degrees, a peak in the range of about 13.3 degrees to about 13.7 degrees, a peak in the range of about 15.5 degrees to about 15.9 degrees, a peak in the range of about 16 degrees to about 16.4 degrees, a peak in the range of about 16.3 degrees to about 16.7 degrees, a peak in the range of about 18.1 degrees to about 18.5 degrees, a peak in the range of about 20.7 degrees to about 21.1 degrees, a peak in the range of about 23.7 degrees to about 24.1 degrees and a peak in the range of about 24.1 degrees to about 24.5 degrees. In some embodiments, sulfate salt Form B can be characterized by one or more peaks in an XRPD pattern, wherein the one or more peaks is selected from a peak in the range of about 4.3 degrees to about 4.7 degrees, a peak in the range of about 7.7 degrees to about 8.1 degrees, a peak in the range of about 8.2 degrees to about 8.6 degrees, a peak in the range of about 8.8 degrees to about 9.2 degrees, a peak in the range of about 11.3 degrees to about 11.7 degrees, a peak in the range of about 11.8 degrees to about 12.2 degrees, a peak in the range of about 13.3 degrees to about 13.7 degrees, a peak in the range of about 15.5 degrees to about 15.9 degrees, a peak in the range of about 16 degrees to about 16.4 degrees, a peak in the range of about 16.3 degrees to about 16.7 degrees, a peak in the range of about 18.1 degrees to about 18.5 degrees, a peak in the range of about 20.7 degrees to about 21.1 degrees, a peak in the range of about 22.2 degrees to about 22.6 degrees, a peak in the range of about 23.7 degrees to about 24.1 degrees, a peak in the range of about 24.1 degrees to about 24.5 degrees, a peak in the range of about 26.2 degrees to about 26.6 degrees and a peak in the range of about 27.2 degrees to about 27.6 degrees.

In some embodiments, sulfate salt Form B can be characterized by one or more peaks in an XPRD pattern, wherein the one or more peaks can be selected from about 4.51 degrees, about 7.93 degrees, about 8.98 degrees, about 11.45 degrees, about 12.00 degrees, about 13.52 degrees, about 15.66 degrees, about 16.22 degrees, about 16.46 degrees, about 18.25 degrees, about 20.88 degrees, about 23.92 degrees and about 24.29 degrees. In some embodiments, sulfate salt Form B can be characterized by one or more peaks in an XRPD pattern, wherein the one or more peaks is selected from about 4.51 degrees, about 7.93 degrees, about 8.43 degrees, about 8.98 degrees, about 11.45 degrees, about 12.00 degrees, about 13.52 degrees, about 15.66 degrees, about 16.22 degrees, about 16.46 degrees, about 18.25 degrees, about 20.88 degrees, about 22.37 degrees, about 23.92 degrees, about 24.29 degrees, about 26.39 degrees and about 27.42 degrees.

Figure 7:
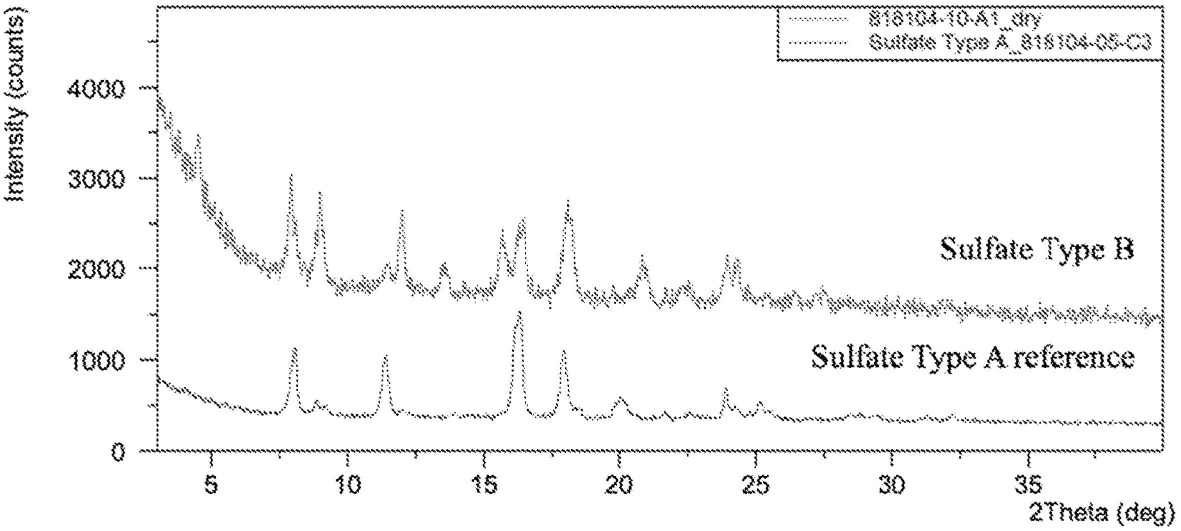
FIG. 7 provides a representative XRPD pattern of sulfate salt Form B.

In some embodiments, sulfate salt Form B can exhibit an XRPD pattern as shown in FIG. 7.

In some embodiments, sulfate salt Form B can be characterized by one or more peaks in an XRPD pattern selected from:

| Peak | 2θ | Relative Intensity [%] |
|---|---|---|
| 1 | 4.51 | 49.41 |
| 2 | 7.93 | 100.00 |
| 3 | 8.43 | 15.38 |
| 4 | 8.98 | 89.98 |
| 5 | 11.45 | 26.54 |
| 6 | 12.00 | 79.69 |
| 7 | 13.52 | 27.30 |
| 8 | 15.66 | 65.61 |
| 9 | 16.22 | 61.70 |
| 10 | 16.46 | 76.08 |
| 11 | 18.25 | 78.40 |
| 12 | 20.88 | 32.02 |
| 13 | 22.37 | 14.09 |
| 14 | 23.92 | 41.18 |
| 15 | 24.29 | 42.42 |
| 16 | 26.39 | 10.29 |
| 17 | 27.42 | 10.61 |

Figure 8:
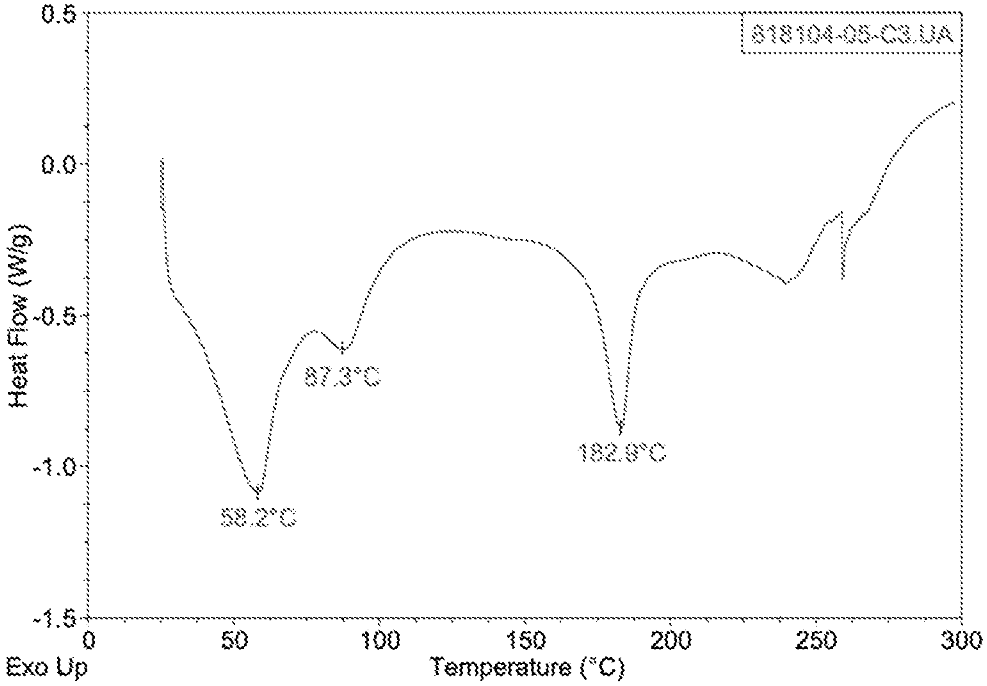
FIG. 8 provides a representative DSC thermogram of sulfate salt Form A.

Sulfate salt Form A can also be characterized by DSC. In some embodiments, sulfate salt Form A can be characterized by a DSC thermogram of FIG. 8. In some embodiments, sulfate salt Form A can be characterized by a first endotherm in the range of about 54° C. to about 62° C., a second endotherm in the range of about 83° C. to about 91° C. and a third endotherm in the range of about 179° C. to about 187° C. In some embodiments, sulfate salt Form A can be characterized by a first endotherm in the range of about 56° C. to about 60° C., a second endotherm in the range of about 85° C. to about 89° C. and a third endotherm in the range of about 181° C. to about 185° C. In some embodiments, sulfate salt Form A can be characterized by a first endotherm at about 58.2° C., a second endotherm at about 87.3° C. and a third endotherm at about 182.9° C.

Figure 9:
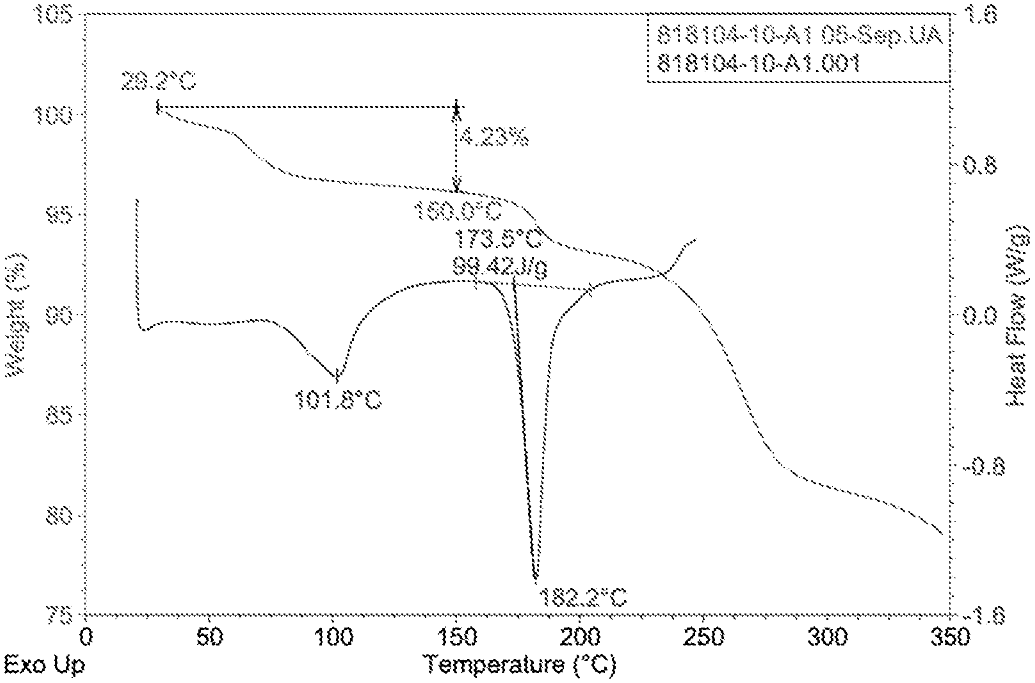
FIG. 9 provides a representative DSC and TGA thermogram of sulfate salt Form B.

Sulfate salt Form B can also be characterized by DSC and/or TGA. In some embodiments, sulfate salt Form B can be characterized by a DSC and/or TGA thermogram of FIG. 9. In some embodiments, sulfate salt Form B can be characterized by a weight loss of about 4.2% when heated from about 29° C. to about 150° C. In some embodiments, sulfate salt Form B can be characterized by a first endotherm in the range of about 98° C. to about 106° C. and a second endotherm in the range of about 178° C. to about 186° C. In some embodiments, sulfate salt Form B can be characterized by a first endotherm in the range of about 100° C. to about 104° C. and a second endotherm in the range of about 180° C. to about 184° C. In some embodiments, sulfate salt Form A can be characterized by a first endotherm at about 101.8° C. and a second endotherm at about 182.2° C.

Some embodiments disclosed herein relate to a pharmaceutically acceptable salt of Compound A, wherein the pharmaceutically acceptable salt can be a mesylate salt. In some embodiments, the mesylate salt form can be mesylate salt Form A. In some embodiments, the molar ratio of mesylate acid to Compound A may be from about 0.6 to about 1.4, from about 0.8 to about 1.2, from about 0.9 to about 1.1 or about 1.

A variety of mesylate salt forms of Compound A can be obtained. In some embodiments, a mesylate salt form described herein can further include a freebase of Compound A (such as those described herein). For example, mesylate salt Form A may further include a small amount of the freebase of Compound A. In some embodiments, a mesylate salt form described herein can further include a small amount of one or more other mesylate salt forms, such as those described herein.

In a salt form of Compound A, various amounts of a mesylate salt form of Compound A can be present. For example, the amount of mesylate salt of Compound A that can be present in mesylate salt Form A can be in the range of about 90% to 100%. In some embodiments, the amount of mesylate salt of Compound A that can be present in mesylate salt Form A can be in the range of about 95% to 100%. In other embodiments, the amount of mesylate salt of Compound A that can be present in mesylate salt Form A can be in the range of about 98% to 100%. In still other embodiments, the amount of mesylate salt of Compound A that can be present in mesylate salt Form A can be in the range of about 95% to 98%. In some embodiments, the amount of mesylate salt of Compound A that can be present in mesylate salt Form A can be ≥90%. In other embodiments, the amount of mesylate salt of Compound A that can be present in mesylate salt Form A can be ≥95%. In still other embodiments, the amount of mesylate salt of Compound A that can be present in mesylate salt Form A can be ≥98%. When less than 100% of a salt form described herein is a mesylate salt from of Compound A, one or more of the components selected from the following can be present in the mesylate salt form of Compound A (such as mesylate salt Form A of Compound A): (1) a freebase of Compound A (including those described herein), (2) a compound that is the result of the degradation of a mesylate salt form of Compound A and/or the degradation of a freebase of Compound A, and (3) an impurity from the synthesis of a mesylate salt form of Compound A and/or the synthesis of a freebase of Compound A.

In some embodiments, mesylate salt Form A can be characterized by one or more peaks in an XRPD pattern, wherein the one or more peaks can be selected from a peak in the range of about 4.5 degrees to about 4.9 degrees, a peak in the range of about 9.2 degrees to about 9.6 degrees, a peak in the range of about 18.6 degrees to about 19 degrees, a peak in the range of about 18.9 degrees to about 19.3 degrees, a peak in the range of about 19.7 degrees to about 20.1 degrees, a peak in the range of about 21 degrees to about 21.4 degrees and a peak in the range of about 23.1 degrees to about 23.5 degrees. In some embodiments, mesylate salt Form A can be characterized by one or more peaks in an XRPD pattern, wherein the one or more peaks is selected from a peak in the range of about 4.5 degrees to about 4.9 degrees, a peak in the range of about 9.2 degrees to about 9.6 degrees, a peak in the range of about 9.7 degrees to about 10.1 degrees, a peak in the range of about 13.1 degrees to about 13.5 degrees, a peak in the range of about 14.3 degrees to about 14.7 degrees, a peak in the range of about 15.1 degrees to about 15.5 degrees, a peak in the range of about 15.6 degrees to about 16 degrees, a peak in the range of about 17.1 degrees to about 17.5 degrees, a peak in the range of about 17.8 degrees to about 18.2 degrees, a peak in the range of about 18.6 degrees to about 19 degrees, a peak in the range of about 18.9 degrees to about 19.3 degrees, a peak in the range of about 19.7 degrees to about 20.1 degrees, a peak in the range of about 21 degrees to about 21.4 degrees, a peak in the range of about 21.5 degrees to about 21.9 degrees, a peak in the range of about 23.1 degrees to about 23.5 degrees, a peak in the range of about 23.4 degrees to about 23.8 degrees, a peak in the range of about 24.6 degrees to about 25 degrees, a peak in the range of about 26 degrees to about 26.4 degrees, a peak in the range of about 26.4 degrees to about 26.8 degrees, a peak in the range of about 28.7 degrees to about 29.1 degrees and a peak in the range of about 33 degrees to about 33.4 degrees.

In some embodiments, mesylate salt Form A can be characterized by one or more peaks in an XPRD pattern, wherein the one or more peaks can be selected from about 4.66 degrees, about 9.36 degrees, about 18.8 degrees, about 19.12 degrees, about 19.9 degrees, about 21.17 degrees and about 23.34 degrees. In some embodiments, mesylate salt Form A can be characterized by one or more peaks in an XRPD pattern, wherein the one or more peaks is selected from about 4.66 degrees, about 9.36 degrees, about 9.89 degrees, about 13.29 degrees, about 14.45 degrees, about 15.26 degrees, about 15.82 degrees, about 17.32 degrees, about 17.98 degrees, about 18.8 degrees, about 19.12 degrees, about 19.9 degrees, about 21.17 degrees, about 21.72 degrees, about 23.34 degrees, about 23.55 degrees, about 24.83 degrees, about 26.18 degrees, about 26.55 degrees, about 28.92 degrees and about 33.2 degrees.

Figure 10:
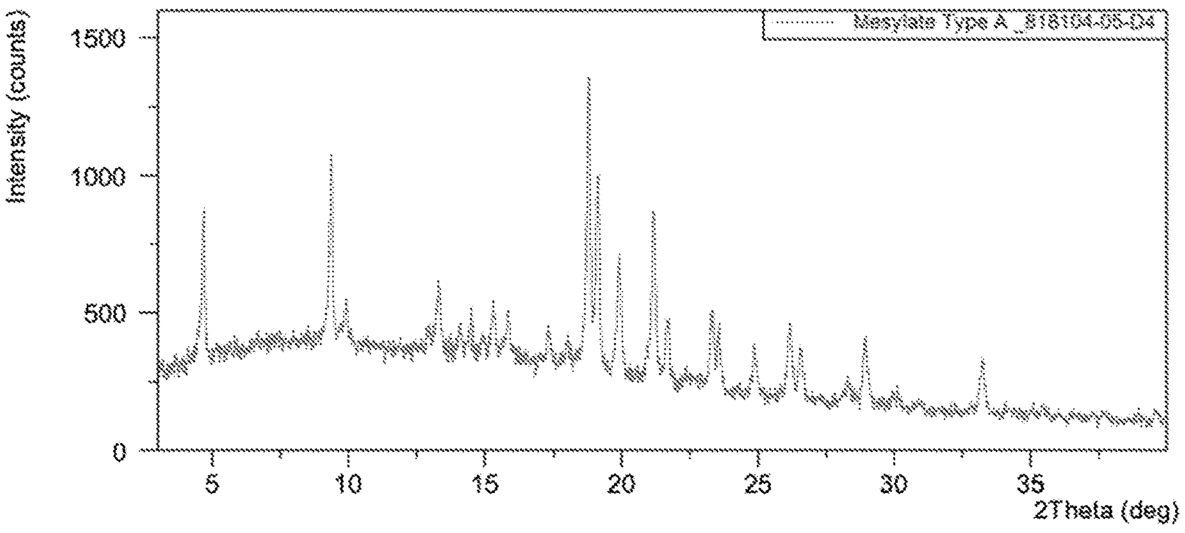
FIG. 10 provides a representative XRPD pattern of mesylate salt Form A.

In some embodiments, mesylate salt Form A can exhibit an XRPD pattern as shown in FIG. 10.

In some embodiments, mesylate salt Form A can be characterized by one or more peaks in an XRPD pattern selected from:

| Peak | 2θ | Relative Intensity [%] |
|---|---|---|
| 1 | 4.66 | 50.86 |
| 2 | 7.00 | 6.22 |
| 3 | 9.36 | 64.25 |
| 4 | 9.89 | 17.57 |
| 5 | 12.91 | 6.78 |
| 6 | 13.29 | 23.29 |
| 7 | 14.07 | 9.61 |
| 8 | 14.45 | 14.82 |
| 9 | 15.26 | 19.17 |
| 10 | 15.82 | 15.85 |
| 11 | 17.32 | 11.57 |
| 12 | 17.98 | 10.28 |
| 13 | 18.80 | 100.00 |
| 14 | 19.12 | 67.66 |
| 15 | 19.90 | 37.91 |
| 16 | 21.17 | 56.49 |
| 17 | 21.72 | 16.57 |
| 18 | 23.34 | 24.95 |
| 19 | 23.55 | 18.17 |
| 20 | 24.83 | 16.04 |
| 21 | 26.18 | 22.30 |
| 22 | 26.55 | 16.50 |
| 23 | 28.25 | 6.61 |
| 24 | 28.92 | 18.89 |
| 25 | 30.04 | 3.46 |
| 26 | 33.20 | 18.42 |
| 27 | 35.48 | 2.55 |
| 28 | 36.01 | 1.27 |

Figure 11:
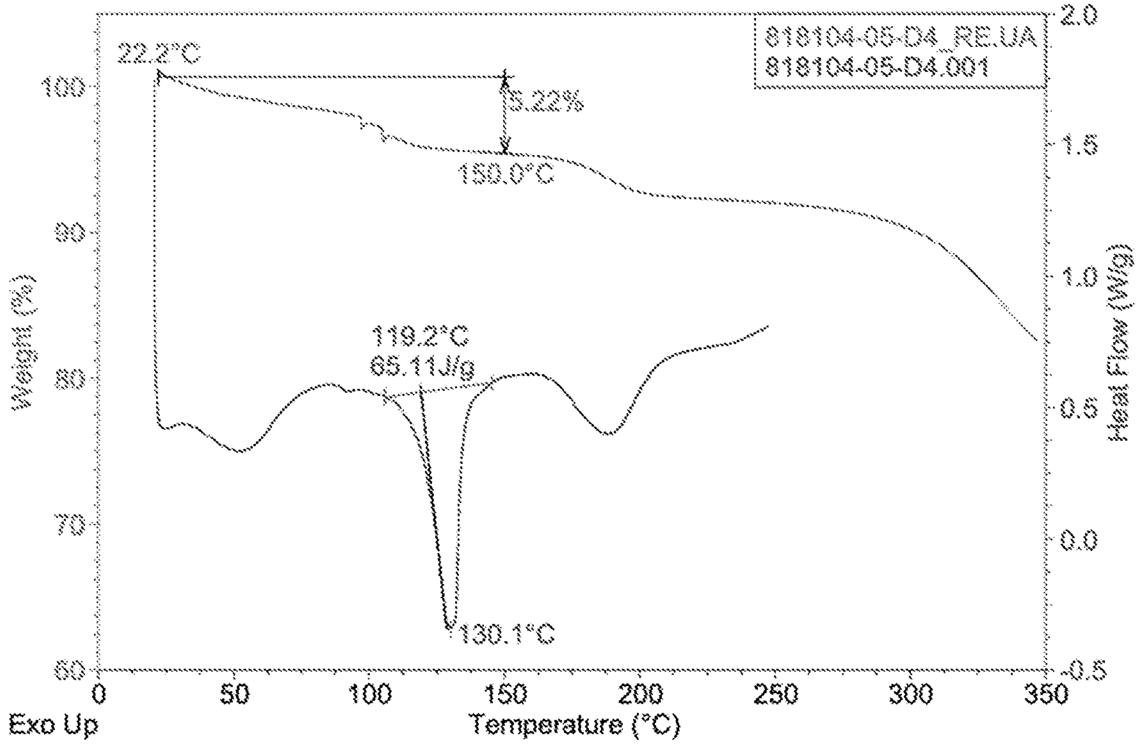
FIG. 11 provides a representative DSC and TGA thermogram of mesylate salt Form A.

Mesylate salt Form A can also be characterized by DSC and/or TGA. In some embodiments, mesylate salt Form A can be characterized by a DSC and/or TGA thermogram of FIG. 11. In some embodiments, mesylate salt Form A can be characterized by a weight loss of about 5.2% when heated from about 22° C. to about 150° C. In some embodiments, mesylate salt Form A can be characterized by an endotherm in the range of about 126° C. to about 134° C. In some embodiments, mesylate salt Form A can be characterized by an endotherm in the range of about 128° C. to about 132° C. In some embodiments, mesylate salt Form A can be characterized by an endotherm at about 130.1° C.

Some embodiments disclosed herein relate to a pharmaceutically acceptable salt of Compound A, wherein the pharmaceutically acceptable salt can be a maleate salt. In some embodiments, a maleate salt form can be a maleate salt Form A. In some embodiments, the molar ratio of maleate acid to Compound A may be from about 0.6 to about 1.4, from about 0.8 to about 1.2, from about 0.9 to about 1.1 or about 1.

A variety of maleate salt forms of Compound A can be obtained. In some embodiments, a maleate salt form described herein can further include a freebase of Compound A (such as those described herein). For example, maleate salt Form A may further include a small amount of freebase Form A. In some embodiments, a maleate salt form described herein can further include a small amount of one or more other maleate salt forms, such as those described herein.

In a salt form of Compound A, various amounts of a maleate salt form of Compound A can be present. For example, the amount of maleate salt of Compound A that can be present in maleate salt Form A can be in the range of about 90% to 100%. In some embodiments, the amount of maleate salt of Compound A that can be present in maleate salt Form A can be in the range of about 95% to 100%. In other embodiments, the amount of maleate salt of Compound A that can be present in maleate salt Form A can be in the range of about 98% to 100%. In still other embodiments, the amount of maleate salt of Compound A that can be present in maleate salt Form A can be in the range of about 95% to 98%. In some embodiments, the amount of maleate salt of Compound A that can be present in maleate salt Form A can be ≥90%. In other embodiments, the amount of maleate salt of Compound A that can be present in maleate salt Form A can be ≥95%. In still other embodiments, the amount of maleate salt of Compound A that can be present in maleate salt Form A can be ≥98%. When less than 100% of a salt form described herein is a maleate salt of Compound A, one or more of the components selected from the following can be present in the maleate salt form of Compound A (such as maleate salt Form A of Compound A): (1) a freebase of Compound A (including those described herein), (2) a compound that is the result of the degradation of a maleate salt form of Compound A and/or the degradation of a freebase of Compound A, and (3) an impurity from the synthesis of a maleate salt form of Compound A and/or the synthesis of a freebase of Compound A.

In some embodiments, maleate salt Form A can be characterized by one or more peaks in an XRPD pattern, wherein the one or more peaks can be selected from a peak in the range of about 3 degrees to about 3.4 degrees, a peak in the range of about 4.8 degrees to about 5.2 degrees, a peak in the range of about 5 degrees to about 5.4 degrees, a peak in the range of about 10.1 degrees to about 10.5 degrees, a peak in the range of about 15.2 degrees to about 15.6 degrees, a peak in the range of about 15.8 degrees to about 16.2 degrees, a peak in the range of about 16.3 degrees to about 16.7 degrees and a peak in the range of about 21.8 degrees to about 22.2 degrees. In some embodiments, maleate salt Form A can be characterized by one or more peaks in an XRPD pattern, wherein the one or more peaks is selected from a peak in the range of about 3 degrees to about 3.4 degrees, a peak in the range of about 4.8 degrees to about 5.2 degrees, a peak in the range of about 5 degrees to about 5.4 degrees, a peak in the range of about 8.9 degrees to about 9.3 degrees, a peak in the range of about 10.1 degrees to about 10.5 degrees, a peak in the range of about 11.2 degrees to about 11.6 degrees, a peak in the range of about 13.8 degrees to about 14.2 degrees, a peak in the range of about 14.9 degrees to about 15.3 degrees, a peak in the range of about 15.2 degrees to about 15.6 degrees, a peak in the range of about 15.8 degrees to about 16.2 degrees, a peak in the range of about 16.3 degrees to about 16.7 degrees, a peak in the range of about 16.7 degrees to about 17.1 degrees, a peak in the range of about 17.8 degrees to about 18.2 degrees, a peak in the range of about 18.8 degrees to about 19.2 degrees, a peak in the range of about 20.4 degrees to about 20.8 degrees, a peak in the range of about 21.8 degrees to about 22.2 degrees, a peak in the range of about 22.9 degrees to about 23.3 degrees and a peak in the range of about 23.4 degrees to about 23.8 degrees.

In some embodiments, maleate salt Form A can be characterized by one or more peaks in an XPRD pattern, wherein the one or more peaks can be selected from about 3.16 degrees, about 4.99 degrees, about 5.17 degrees, about 10.27 degrees, about 15.41 degrees, about 16.03 degrees, about 16.46 degrees and about 22.02 degrees. In some embodiments, maleate salt Form A can be characterized by one or more peaks in an XRPD pattern, wherein the one or more peaks is selected from about 3.16 degrees, about 4.99 degrees, about 5.17 degrees, about 9.05 degrees, about 10.27 degrees, about 11.43 degrees, about 13.97 degrees, about 15.1 degrees, about 15.41 degrees, about 16.03 degrees, about 16.46 degrees, about 16.87 degrees, about 17.95 degrees, about 18.99 degrees, about 20.56 degrees, about 22.02 degrees, about 23.09 degrees and about 23.55 degrees.

Figure 12:
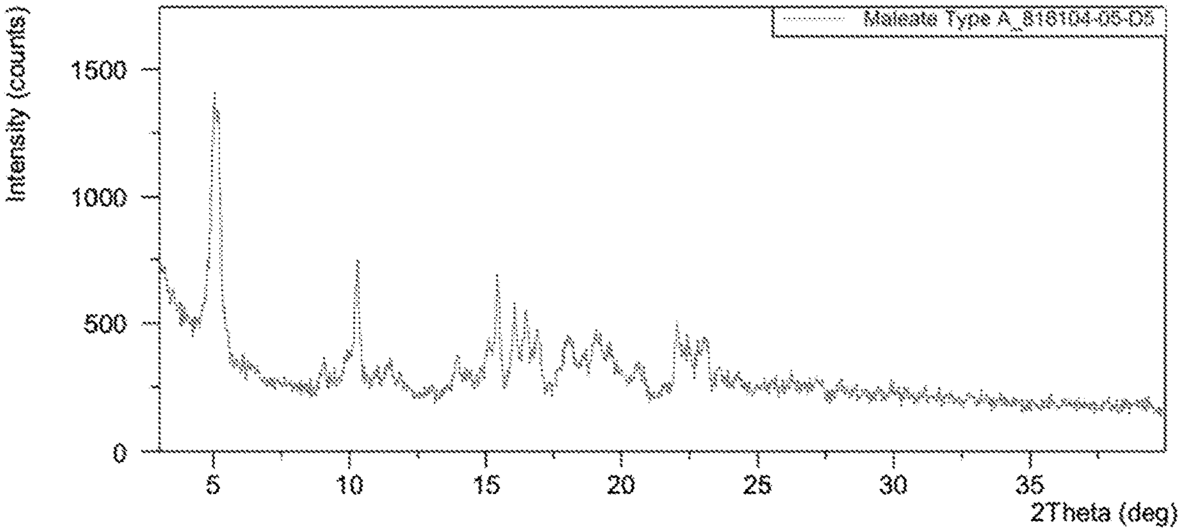
FIG. 12 provides a representative XRPD pattern of maleate salt Form A.

In some embodiments, maleate salt Form A can exhibit an XRPD pattern as shown in FIG. 12.

In some embodiments, maleate salt Form A can be characterized by one or more peaks in an XRPD pattern selected from:

| Peak | 2θ | Relative Intensity [%] |
|---|---|---|
| 1 | 3.16 | 37.77 |
| 2 | 4.99 | 100.00 |
| 3 | 5.17 | 95.24 |
| 4 | 9.05 | 11.35 |
| 5 | 10.27 | 48.16 |
| 6 | 11.43 | 10.23 |
| 7 | 13.97 | 14.57 |
| 8 | 15.10 | 20.18 |
| 9 | 15.41 | 43.97 |
| 10 | 16.03 | 28.63 |
| 11 | 16.46 | 30.07 |
| 12 | 16.87 | 24.70 |
| 13 | 17.95 | 19.52 |
| 14 | 18.99 | 20.35 |
| 15 | 20.56 | 11.48 |
| 16 | 22.02 | 27.03 |
| 17 | 23.09 | 20.39 |
| 18 | 23.55 | 10.32 |
| 19 | 24.28 | 6.89 |
| 20 | 27.21 | 5.03 |
| 21 | 28.01 | 3.75 |

Figure 13:
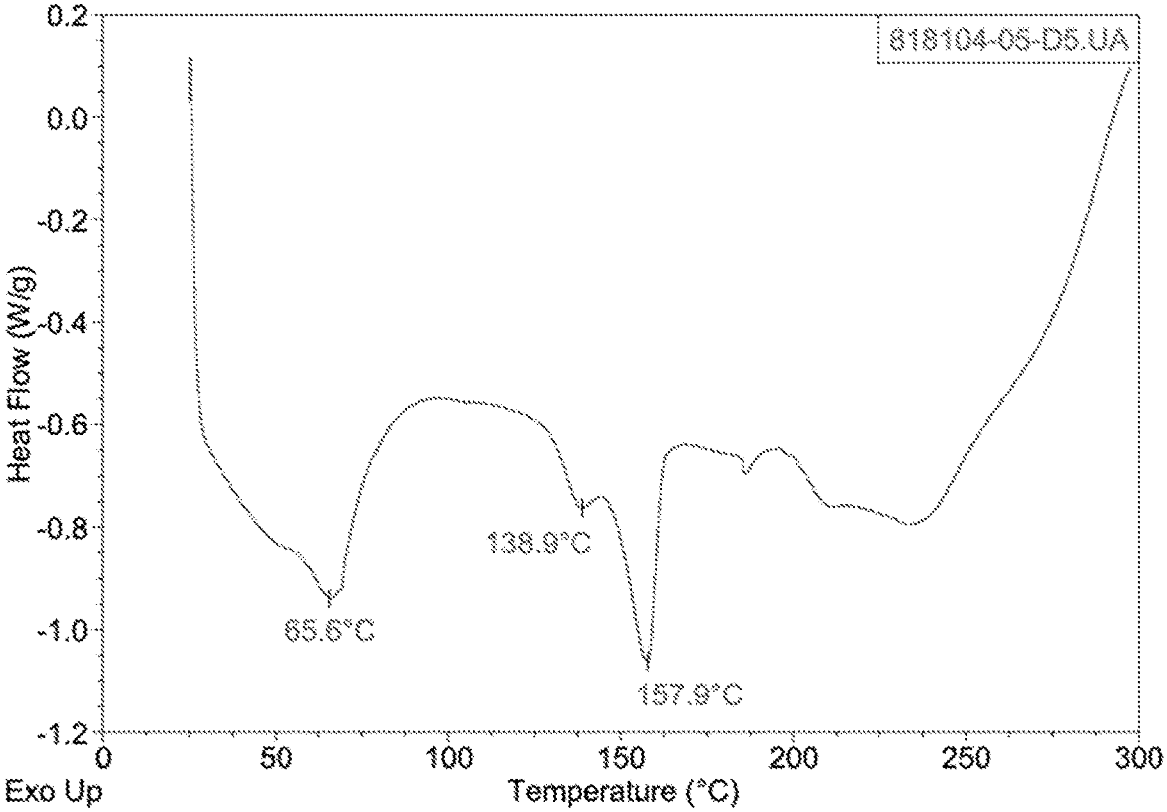
FIG. 13 provides a representative DSC thermogram of maleate salt Form A.

Maleate salt Form A can also be characterized by DSC. In some embodiments, maleate salt Form A can be characterized by a DSC thermogram of FIG. 13. In some embodiments, maleate salt Form A can be characterized by a first endotherm in the range of about 62° C. to about 70° C., a second endotherm in the range of about 135° C. to about 143° C. and a third endotherm in the range of about 154° C. to about 162° C. In some embodiments, maleate salt Form A can be characterized by a first endotherm in the range of about 64° C. to about 68° C., a second endotherm in the range of about 137° C. to about 141° C. and a third endotherm in the range of about 156° C. to about 160° C. In some embodiments, maleate salt Form A can be characterized by a first endotherm at about 65.6° C., a second endotherm at about 138.9° C. and a third endotherm at about 157.9° C.

Some embodiments disclosed herein relate to a pharmaceutically acceptable salt of Compound A, wherein the pharmaceutically acceptable salt can be a phosphate salt. In some embodiments, a phosphate salt form can be phosphate salt Form A. In some embodiments, the molar ratio of phosphate acid to Compound A may be from about 0.6 to about 1.4, from about 0.8 to about 1.2, from about 0.9 to about 1.1 or about 1.

A variety of phosphate salt forms of Compound A can be obtained. In some embodiments, a phosphate salt form described herein can further include a freebase of Compound A, such as those described herein. For example, phosphate salt Form A may further include a small amount of freebase Form A. In some embodiments, a phosphate salt form described herein can further include a small amount of one or more other phosphate salt forms, such as those described herein.

In a salt form of Compound A, various amounts of a phosphate salt form of Compound A can be present. For example, the amount of phosphate salt of Compound A that can be present in phosphate salt Form A can be in the range of about 90% to 100%. In some embodiments, the amount of phosphate salt of Compound A that can be present in phosphate salt Form A can be in the range of about 95% to 100%. In other embodiments, the amount of phosphate salt of Compound A that can be present in phosphate salt Form A can be in the range of about 98% to 100%. In still other embodiments, the amount of phosphate salt of Compound A that can be present in phosphate salt Form A can be in the range of about 95% to 98%. In some embodiments, the amount of phosphate salt of Compound A that can be present in phosphate salt Form A can be ≥90%. In other embodiments, the amount of phosphate salt of Compound A that can be present in phosphate salt Form A can be ≥95%. In still other embodiments, the amount of phosphate salt of Compound A that can be present in phosphate salt Form A can be ≥98%. When less than 100% of a salt form described herein is a phosphate salt of Compound A, one or more of the components selected from the following can be present in the phosphate salt form of Compound A (such as phosphate salt Form A of Compound A): (1) a freebase of Compound A, such as those described herein, (2) a compound that is the result of the degradation of a phosphate salt form of Compound A and/or the degradation of a freebase of Compound A, and (3) an impurity from the synthesis of a phosphate salt form of Compound A and/or the synthesis of a freebase of Compound A.

In some embodiments, phosphate salt Form A can be characterized by one or more peaks in an XRPD pattern, wherein the one or more peaks can be selected from a peak in the range of about 9.3 degrees to about 9.7 degrees, a peak in the range of about 10.9 degrees to about 11.3 degrees, a peak in the range of about 17.4 degrees to about 17.8 degrees, a peak in the range of about 18.8 degrees to about 19.2 degrees, a peak in the range of about 21.7 degrees to about 22.1 degrees and a peak in the range of about 23.4 degrees to about 23.8 degrees. In some embodiments, phosphate salt Form A can be characterized by one or more peaks in an XRPD pattern, wherein the one or more peaks is selected from a peak in the range of about 4.6 degrees to about 5 degrees, a peak in the range of about 9.3 degrees to about 9.7 degrees, a peak in the range of about 9.7 degrees to about 10.1 degrees, a peak in the range of about 10.9 degrees to about 11.3 degrees, a peak in the range of about 13.2 degrees to about 13.6 degrees, a peak in the range of about 14.1 degrees to about 14.5 degrees, a peak in the range of about 15.6 degrees to about 16 degrees, a peak in the range of about 17.4 degrees to about 17.8 degrees, a peak in the range of about 18.8 degrees to about 19.2 degrees, a peak in the range of about 19.9 degrees to about 20.3 degrees, a peak in the range of about 21.7 degrees to about 22.1 degrees, a peak in the range of about 23.4 degrees to about 23.8 degrees, a peak in the range of about 25.5 degrees to about 25.9 degrees and a peak in the range of about 27.4 degrees to about 27.8 degrees.

In some embodiments, phosphate salt Form A can be characterized by one or more peaks in an XPRD pattern, wherein the one or more peaks can be selected from about 9.49 degrees, about 11.1 degrees, about 17.57 degrees, about 19.03 degrees, about 21.89 degrees and about 23.62 degrees. In some embodiments, phosphate salt Form A can be characterized by one or more peaks in an XRPD pattern, wherein the one or more peaks is selected from about 4.77 degrees, about 9.49 degrees, about 9.94 degrees, about 11.1 degrees, about 13.43 degrees, about 14.3 degrees, about 15.77 degrees, about 17.57 degrees, about 19.03 degrees, about 20.12 degrees, about 21.89 degrees, about 23.62 degrees, about 25.72 degrees and about 27.59 degrees.

Figure 14:
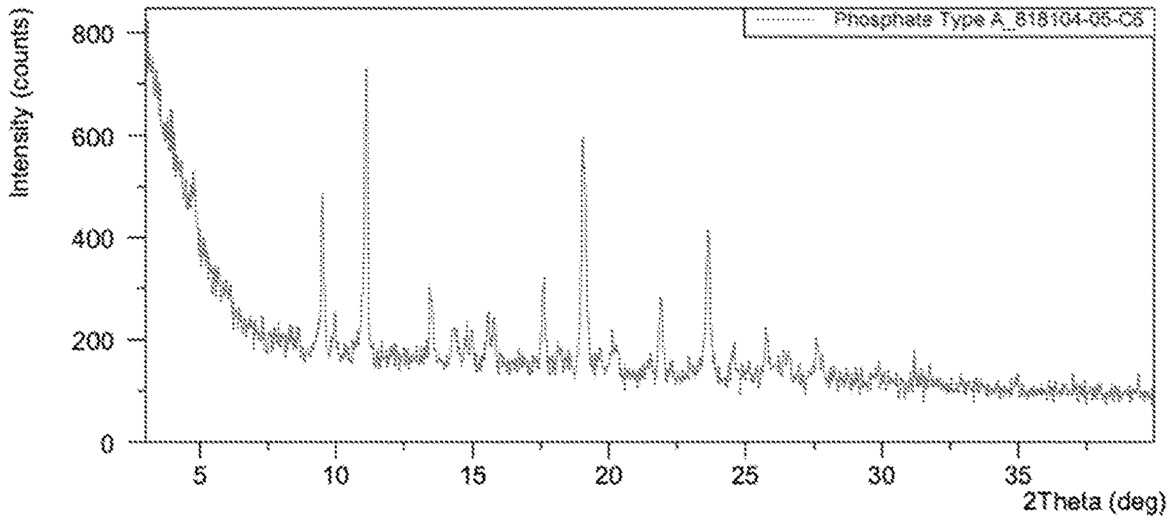
FIG. 14 provides a representative XRPD pattern of phosphate salt Form A.

In some embodiments, phosphate salt Form A can exhibit an XRPD pattern as shown in FIG. 14.

In some embodiments, phosphate salt Form A can be characterized by one or more peaks in an XRPD pattern selected from:

| Peak | 2θ | Relative Intensity [%] |
|---|---|---|
| 1 | 4.77 | 10.38 |
| 2 | 9.49 | 55.00 |
| 3 | 9.94 | 10.52 |
| 4 | 11.10 | 100.00 |
| 5 | 13.43 | 22.96 |
| 6 | 14.30 | 11.84 |
| 7 | 14.87 | 8.65 |
| 8 | 15.77 | 16.68 |
| 9 | 17.57 | 29.17 |
| 10 | 19.03 | 79.91 |
| 11 | 20.12 | 12.47 |
| 12 | 21.89 | 27.03 |
| 13 | 23.62 | 52.07 |
| 14 | 24.57 | 9.36 |
| 15 | 25.72 | 17.88 |
| 16 | 26.57 | 8.64 |
| 17 | 27.59 | 12.70 |

Figure 15:
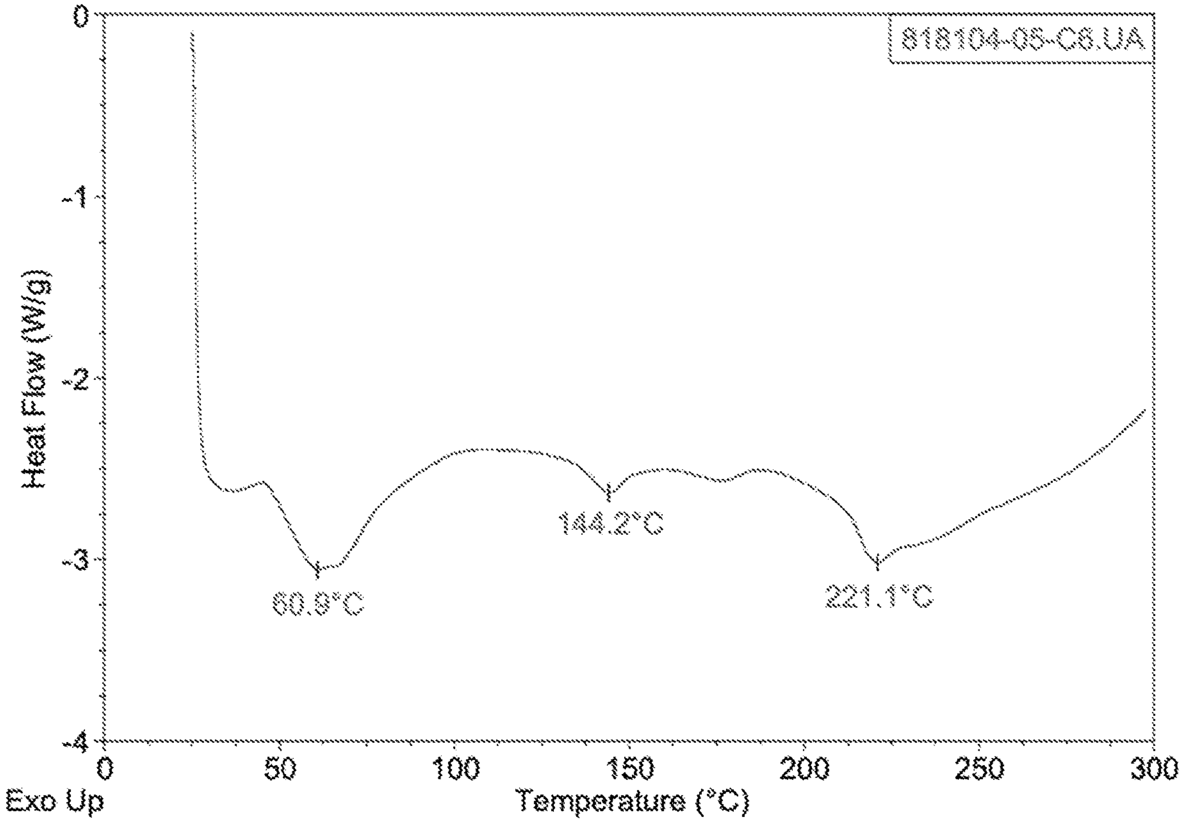
FIG. 15 provides a representative DSC thermogram of phosphate salt Form A.

Phosphate salt Form A can also be characterized by DSC. In some embodiments, phosphate salt Form A can be characterized by a DSC thermogram of FIG. 15. In some embodiments, phosphate salt Form A can be characterized by a first endotherm in the range of about 57° C. to about 65° C., a second endotherm in the range of about 140° C. to about 148° C. and a third endotherm in the range of about 217° C. to about 225° C. In some embodiments, phosphate salt Form A can be characterized by a first endotherm in the range of about 59° C. to about 63° C., a second endotherm in the range of about 142° C. to about 146° C. and a third endotherm in the range of about 219° C. to about 223° C. In some embodiments, phosphate salt Form A can be characterized by a first endotherm at about 60.9° C., a second endotherm at about 144.2° C. and a third endotherm at 221.1° C.

Some embodiments disclosed herein relate to a pharmaceutically acceptable salt of Compound A, wherein the pharmaceutically acceptable salt can be a tartrate salt. In some embodiments, a tartrate salt form can be tartrate salt Form A. In some embodiments, the molar ratio of tartrate acid to Compound A may be from about 0.6 to about 1.4, from about 0.8 to about 1.2, from about 0.9 to about 1.1 or about 1.

A variety of tartrate salt forms of Compound A can be obtained. In some embodiments, a tartrate salt form described herein can further include a freebase of Compound A (including those described herein). For example, tartrate salt Form A may further include a small amount of freebase Form A. In some embodiments, a tartrate salt form described herein can further include a small amount of one or more other tartrate salt forms, such as those described herein.

In a salt form of Compound A, various amounts of a tartrate salt form of Compound A can be present. For example, the amount of tartrate salt of Compound A that can be present in tartrate salt Form A can be in the range of about 90% to 100%. In some embodiments, the amount of tartrate salt of Compound A that can be present in tartrate salt Form A can be in the range of about 95% to 100%. In other embodiments, the amount of tartrate salt of Compound A that can be present in tartrate salt Form A can be in the range of about 98% to 100%. In still other embodiments, the amount of tartrate salt of Compound A that can be present in tartrate salt Form A can be in the range of about 95% to 98%. In some embodiments, the amount of tartrate salt of Compound A that can be present in tartrate salt Form A can be ≥90%. In other embodiments, the amount of tartrate salt of Compound A that can be present in tartrate salt Form A can be ≥95%. In still other embodiments, the amount of tartrate salt of Compound A that can be present in tartrate salt Form A can be ≥98%. When less than 100% of a salt form described herein is a tartrate salt of Compound A, one or more of the components selected from the following can be present in the tartrate salt form of Compound A (such as tartrate salt Form A of Compound A): (1) a freebase of Compound A (such as those described herein), (2) a compound that is the result of the degradation of a tartrate salt form of Compound A and/or the degradation of a freebase of Compound A, and (3) an impurity from the synthesis of a tartrate salt form of Compound A and/or the synthesis of a freebase of Compound A.

In some embodiments, tartrate salt Form A can be characterized by one or more peaks in an XRPD pattern, wherein the one or more peaks can be selected from a peak in the range of about 4.1 degrees to about 4.5 degrees, a peak in the range of about 8.3 degrees to about 8.7 degrees, a peak in the range of about 9 degrees to about 9.4 degrees, a peak in the range of about 11.9 degrees to about 12.3 degrees, a peak in the range of about 12.5 degrees to about 12.9 degrees, a peak in the range of about 15.3 degrees to about 15.7 degrees, a peak in the range of about 15.5 degrees to about 15.9 degrees, a peak in the range of about 17.8 degrees to about 18.2 degrees, a peak in the range of about 18.3 degrees to about 18.7 degrees, a peak in the range of about 19.5 degrees to about 19.9 degrees, a peak in the range of about 21.1 degrees to about 21.5 degrees, a peak in the range of about 21.9 degrees to about 22.3 degrees, a peak in the range of about 23.2 degrees to about 23.6 degrees, a peak in the range of about 24.2 degrees to about 24.6 degrees, a peak in the range of about 25.3 degrees to about 25.7 degrees and a peak in the range of about 26.9 degrees to about 27.3 degrees. In some embodiments, tartrate salt Form A can be characterized by one or more peaks in an XRPD pattern, wherein the one or more peaks is selected from a peak in the range of about 4.1 degrees to about 4.5 degrees, a peak in the range of about 8.3 degrees to about 8.7 degrees, a peak in the range of about 9 degrees to about 9.4 degrees, a peak in the range of about 11.9 degrees to about 12.3 degrees, a peak in the range of about 12.5 degrees to about 12.9 degrees, a peak in the range of about 14.1 degrees to about 14.5 degrees, a peak in the range of about 14.5 degrees to about 14.9 degrees, a peak in the range of about 15.3 degrees to about 15.7 degrees, a peak in the range of about 15.5 degrees to about 15.9 degrees, a peak in the range of about 17.8 degrees to about 18.2 degrees, a peak in the range of about 18.3 degrees to about 18.7 degrees, a peak in the range of about 19.5 degrees to about 19.9 degrees, a peak in the range of about 21.1 degrees to about 21.5 degrees, a peak in the range of about 21.9 degrees to about 22.3 degrees, a peak in the range of about 22.7 degrees to about 23.1 degrees, a peak in the range of about 23.2 degrees to about 23.6 degrees, a peak in the range of about 24.2 degrees to about 24.6 degrees, a peak in the range of about 24.9 degrees to about 25.3 degrees, a peak in the range of about 25.3 degrees to about 25.7 degrees, a peak in the range of about 26.2 degrees to about 26.6 degrees, a peak in the range of about 26.9 degrees to about 27.3 degrees and a peak in the range of about 29.9 degrees to about 30.3 degrees.

In some embodiments, tartrate salt Form A can be characterized by one or more peaks in an XPRD pattern, wherein the one or more peaks can be selected from about 4.27 degrees, about 8.48 degrees, about 9.21 degrees, about 12.05 degrees, about 12.71 degrees, about 15.54 degrees, about 15.74 degrees, about 17.98 degrees, about 18.46 degrees, about 19.72 degrees, about 21.25 degrees, about 22.11 degrees, about 23.37 degrees, about 24.37 degrees, about 25.54 degrees and about 27.12 degrees. In some embodiments, tartrate salt Form A can be characterized by one or more peaks in an XRPD pattern, wherein the one or more peaks is selected from about 4.27 degrees, about 8.48 degrees, about 9.21 degrees, about 12.05 degrees, about 12.71 degrees, about 14.25 degrees, about 14.74 degrees, about 15.54 degrees, about 15.74 degrees, about 17.98 degrees, about 18.46 degrees, about 19.72 degrees, about 21.25 degrees, about 22.11 degrees, about 22.86 degrees, about 23.37 degrees, about 24.37 degrees, about 25.09 degrees, about 25.54 degrees, about 26.4 degrees, about 27.12 degrees and about 30.12 degrees.

Figure 16:
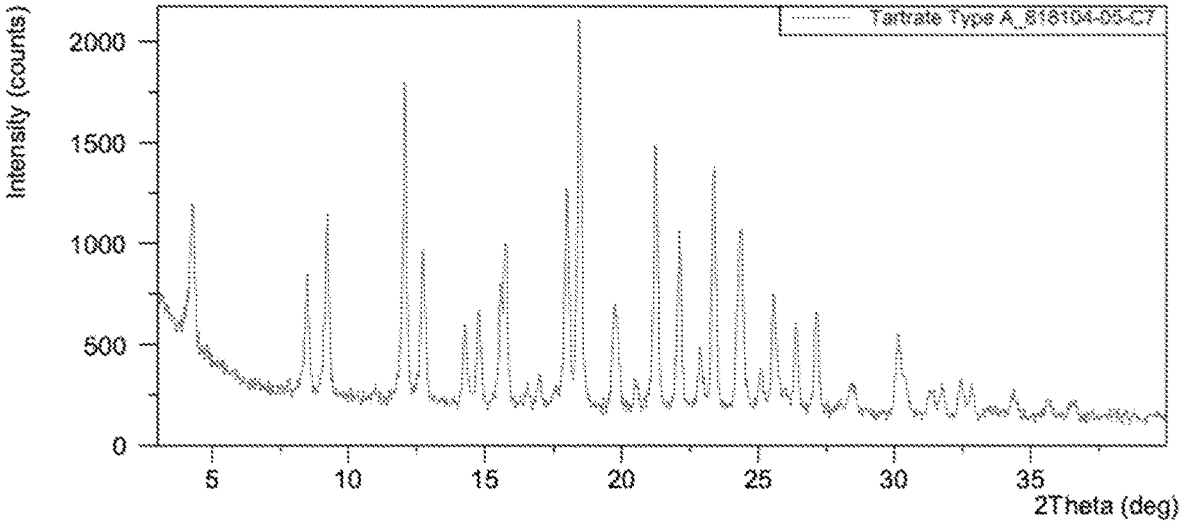
FIG. 16 provides a representative XRPD pattern of tartrate salt Form A.

In some embodiments, tartrate salt Form A can exhibit an XRPD pattern as shown in FIG. 16.

In some embodiments, tartrate salt Form A can be characterized by one or more peaks in an XRPD pattern selected from:

| Peak | 2θ | Relative Intensity [%] |
|---|---|---|
| 1 | 4.27 | 34.27 |
| 2 | 8.48 | 31.48 |
| 3 | 9.21 | 46.88 |
| 4 | 12.05 | 80.43 |
| 5 | 12.71 | 38.60 |
| 6 | 14.25 | 20.24 |
| 7 | 14.74 | 23.73 |
| 8 | 15.54 | 28.23 |

-continued

| Peak | 2θ | Relative Intensity [%] |
|---|---|---|
| 9 | 15.74 | 41.62 |
| 10 | 16.54 | 5.31 |
| 11 | 17.00 | 7.05 |
| 12 | 17.98 | 55.56 |
| 13 | 18.46 | 100.00 |
| 14 | 19.72 | 25.43 |
| 15 | 20.49 | 6.10 |
| 16 | 21.25 | 69.20 |
| 17 | 22.11 | 45.07 |
| 18 | 22.86 | 14.50 |
| 19 | 23.37 | 63.08 |
| 20 | 24.37 | 46.47 |
| 21 | 25.09 | 10.10 |
| 22 | 25.54 | 29.31 |
| 23 | 26.40 | 21.42 |
| 24 | 27.12 | 25.85 |
| 25 | 28.47 | 6.83 |
| 26 | 30.12 | 17.41 |
| 27 | 31.35 | 5.58 |
| 28 | 31.75 | 6.07 |
| 29 | 32.43 | 8.97 |
| 30 | 32.83 | 7.40 |
| 31 | 34.35 | 5.03 |
| 32 | 35.62 | 4.09 |
| 33 | 36.60 | 3.48 |

Figure 17:
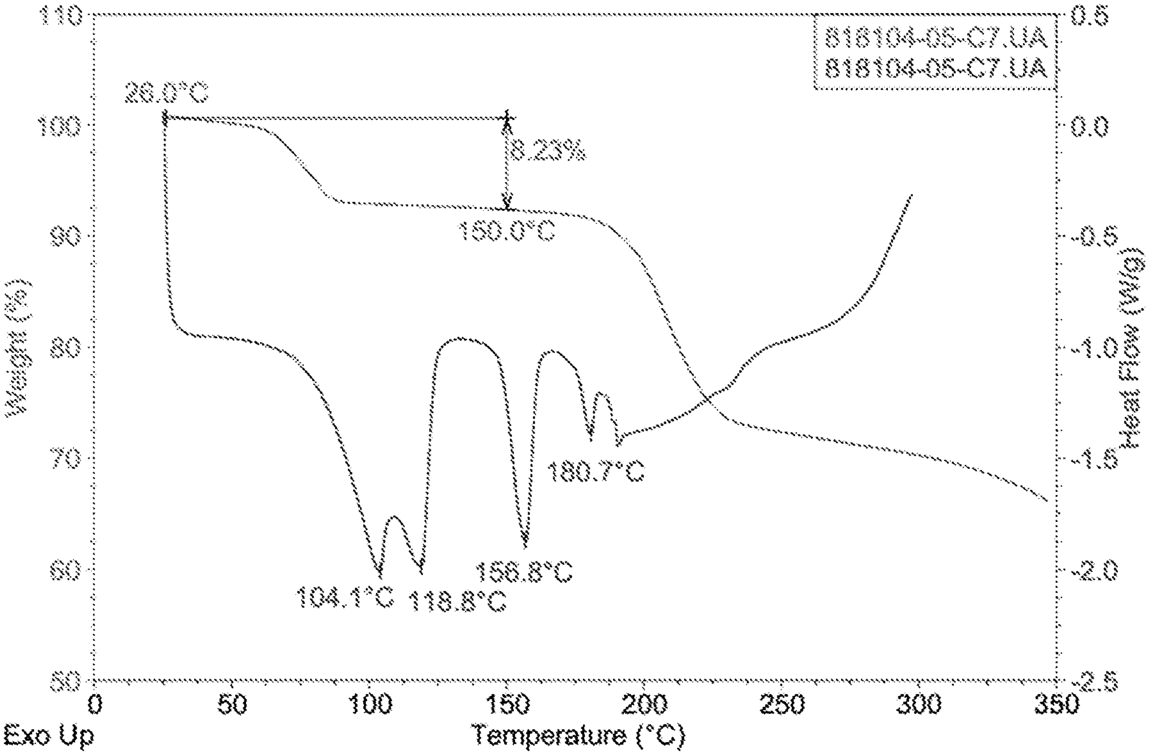
FIG. 17 provides a representative DSC and TGA thermogram of tartrate salt Form A.

Tartrate salt Form A can also be characterized by DSC and/or TGA. In some embodiments, tartrate salt Form A can be characterized by a DSC and/or TGA thermogram of FIG. 17. In some embodiments, tartrate salt Form A can be characterized by a weight loss of about 8.2% when heated from about 26° C. to about 150 TC. In some embodiments, tartrate salt Form A can be characterized by a first endotherm in the range of about 100° C. to about 108° C., a second endotherm in the range of about 115° C. to about 123° C., a third endotherm in the range of about 153° C. to about 161° C. and a fourth endotherm in the range of about 177° C. to about 185° C. In some embodiments, tartrate salt Form A can be characterized by a first endotherm in the range of about 102° C. to about 106° C., a second endotherm in the range of about 117° C. to about 121° C., a third endotherm in the range of about 155° C. to about 159° C. and a fourth endotherm in the range of about 179° C. to about 183° C. In some embodiments, tartrate salt Form A can be characterized by a first endotherm at about 104.1° C., a second endotherm at about 118.8° C., a third endotherm at about 156.8° C. and a fourth endotherm at about 180.7° C.

Some embodiments disclosed herein relate to a pharmaceutically acceptable salt of Compound A, wherein the pharmaceutically acceptable salt can be a tosylate salt. In some embodiments, a tosylate salt form can be tosylate salt Form A. In some embodiments, the molar ratio of tosylate acid to Compound A may be from about 0.6 to about 1.4, from about 0.8 to about 1.2, from about 0.9 to about 1.1, or about 1.

A variety of tosylate salt forms of Compound A can be obtained. In some embodiments, a tosylate salt form described herein can further include a freebase of Compound A. For example, tosylate salt Form A may further include a small amount of freebase Form A. In some embodiments, a tosylate salt form described herein can further include a small amount of one or more other tosylate salt forms, such as those described herein.

In a salt form of Compound A, various amounts of a tosylate salt form of Compound A can be present. For example, the amount of tosylate salt of Compound A that can be present in tosylate salt Form A can be in the range of about 90% to 100%. In some embodiments, the amount of tosylate salt of Compound A that can be present in tosylate salt Form A can be in the range of about 95% to 100%. In other embodiments, the amount of tosylate salt of Compound A that can be present in tosylate salt Form A can be in the range of about 98% to 100%. In still other embodiments, the amount of tosylate salt of Compound A that can be present in tosylate salt Form A can be in the range of about 95% to 98%. In some embodiments, the amount of tosylate salt of Compound A that can be present in tosylate salt Form A can be ≥90%. In other embodiments, the amount of tosylate salt of Compound A that can be present in tosylate salt Form A can be ≥95%. In still other embodiments, the amount of tosylate salt of Compound A that can be present in tosylate salt Form A can be ≥98%. When less than 100% of a salt form described herein is a tosylate salt form of Compound A, one or more of the components selected from the following can be present in the tosylate salt form of Compound A (such as tosylate salt Form A of Compound A): (1) a freebase of Compound A (including those described herein), (2) a compound that is the result of the degradation of a tosylate salt form of Compound A and/or the degradation of a freebase of Compound A, and (3) an impurity from the synthesis of a tosylate salt form of Compound A and/or the synthesis of a freebase of Compound A.

In some embodiments, tosylate salt Form A can be characterized by one or more peaks in an XRPD pattern, wherein the one or more peaks can be selected from a peak in the range of about 7.9 degrees to about 8.3 degrees, a peak in the range of about 10.7 degrees to about 11.1 degrees, a peak in the range of about 14.5 degrees to about 14.9 degrees, a peak in the range of about 15.9 degrees to about 16.3 degrees, a peak in the range of about 16.9 degrees to about 17.3 degrees, a peak in the range of about 18 degrees to about 18.4 degrees, a peak in the range of about 19.5 degrees to about 19.9 degrees, a peak in the range of about 20 degrees to about 20.4 degrees, a peak in the range of about 21.1 degrees to about 21.5 degrees, a peak in the range of about 22.5 degrees to about 22.9 degrees, a peak in the range of about 24.8 degrees to about 25.2 degrees and a peak in the range of about 27.7 degrees to about 28.1 degrees. In some embodiments, tosylate salt Form A can be characterized by one or more peaks in an XRPD pattern, wherein the one or more peaks is selected from a peak in the range of about 7.9 degrees to about 8.3 degrees, a peak in the range of about 10.7 degrees to about 11.1 degrees, a peak in the range of about 12.6 degrees to about 13 degrees, a peak in the range of about 14.5 degrees to about 14.9 degrees, a peak in the range of about 15.9 degrees to about 16.3 degrees, a peak in the range of about 16.9 degrees to about 17.3 degrees, a peak in the range of about 18 degrees to about 18.4 degrees, a peak in the range of about 19 degrees to about 19.4 degrees, a peak in the range of about 19.5 degrees to about 19.9 degrees, a peak in the range of about 20 degrees to about 20.4 degrees, a peak in the range of about 21.1 degrees to about 21.5 degrees, a peak in the range of about 22.5 degrees to about 22.9 degrees, a peak in the range of about 23.3 degrees to about 23.7 degrees, a peak in the range of about 24.3 degrees to about 24.7 degrees, a peak in the range of about 24.8 degrees to about 25.2 degrees, a peak in the range of about 25.6 degrees to about 26 degrees, a peak in the range of about 27 degrees to about 27.4 degrees, a peak in the range of about 27.7 degrees to about 28.1 degrees, a peak in the range of about 28.3 degrees to about 28.7 degrees and a peak in the range of about 30.5 degrees to about 30.9 degrees.

In some embodiments, tosylate salt Form A can be characterized by one or more peaks in an XPRD pattern, wherein the one or more peaks can be selected from about 8.06 degrees, about 10.87 degrees, about 14.67 degrees, about 16.13 degrees, about 17.11 degrees, about 18.22 degrees, about 19.66 degrees, about 20.17 degrees, about 21.29 degrees, about 22.71 degrees, about 25.04 degrees and about 27.94 degrees. In some embodiments, tosylate salt Form A can be characterized by one or more peaks in an XRPD pattern, wherein the one or more peaks is selected from about 8.06 degrees, about 10.87 degrees, about 12.79 degrees, about 14.67 degrees, about 16.13 degrees, about 17.11 degrees, about 18.22 degrees, about 19.2 degrees, about 19.66 degrees, about 20.17 degrees, about 21.29 degrees, about 22.71 degrees, about 23.46 degrees, about 24.5 degrees, about 25.04 degrees, about 25.82 degrees, about 27.19 degrees, about 27.94 degrees, about 28.5 degrees and about 30.73 degrees.

Figure 18:
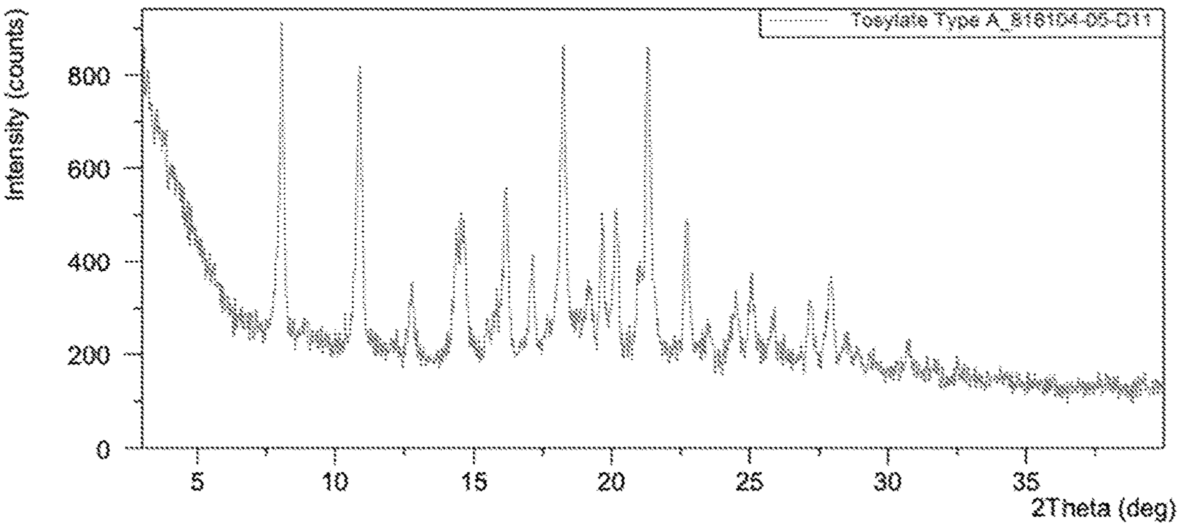
FIG. 18 provides a representative XRPD pattern of tosylate salt Form A.

In some embodiments, tosylate salt Form A can exhibit an XRPD pattern as shown in FIG. 18.

In some embodiments, tosylate salt Form A can be characterized by one or more peaks in an XRPD pattern selected from:

| Peak | 2θ | Relative Intensity [%] |
|---|---|---|
| 1 | 8.06 | 89.54 |
| 2 | 10.87 | 88.24 |
| 3 | 12.79 | 16.96 |
| 4 | 14.67 | 38.99 |
| 5 | 16.13 | 52.68 |
| 6 | 17.11 | 32.73 |
| 7 | 18.22 | 98.97 |
| 8 | 19.20 | 24.66 |
| 9 | 19.66 | 44.57 |
| 10 | 20.17 | 47.55 |
| 11 | 21.29 | 100.00 |
| 12 | 22.71 | 47.44 |
| 13 | 23.46 | 14.80 |
| 14 | 24.50 | 22.13 |
| 15 | 25.04 | 27.90 |
| 16 | 25.82 | 17.41 |
| 17 | 27.19 | 22.07 |
| 18 | 27.94 | 29.50 |
| 19 | 28.50 | 10.46 |
| 20 | 30.73 | 10.49 |

Figure 19:
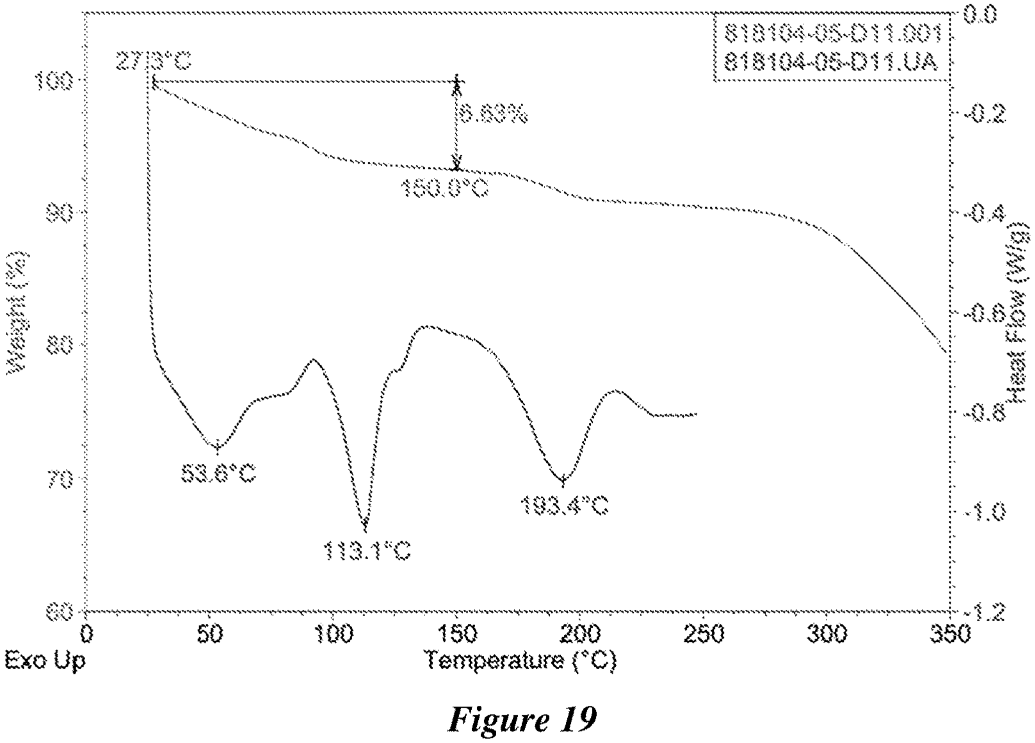
FIG. 19 provides a representative DSC and TGA thermogram of tosylate salt Form A.

Tosylate salt Form A can also be characterized by DSC and/or TGA. In some embodiments, tosylate salt Form A can be characterized by a DSC and/or TGA thermogram of FIG. 19. In some embodiments, tosylate salt Form A can be characterized by a weight loss of about 6.6% when heated from about 27° C. to about 150° C. In some embodiments, tosylate salt Form A can be characterized by a first endotherm in the range of about 50° C. to about 58° C., a second endotherm in the range of about 109° C. to about 117° C. and a third endotherm in the range of about 189° C. to about 197° C. In some embodiments, tosylate salt Form A can be characterized by a first endotherm in the range of about 52° C. to about 56° C., a second endotherm in the range of about 111° C. to about 115° C. and a third endotherm in the range of about 191° C. to about 195° C. In some embodiments, tosylate salt Form A can be characterized by a first endotherm at about 53.6° C., a second endotherm at about 113.1° C. and a third endotherm at about 193.4° C.

Some embodiments disclosed herein relate to a pharmaceutically acceptable salt of Compound A, wherein the pharmaceutically acceptable salt can be a mucate salt. In some embodiments, a mucate salt form can be mucate salt Form A. In some embodiments, the molar ratio of mucate acid to Compound A may be from about 0.6 to about 1.4, from about 0.8 to about 1.2, from about 0.9 to about 1.1 or about 1.

A variety of mucate salt forms of Compound A can be obtained. In some embodiments, a mucate salt form described herein can further include a freebase of Compound A. For example, mucate salt Form A may further include a small amount of freebase Form A. In some embodiments, a mucate salt form described herein can further include a small amount of one or more other mucate salt forms, such as those described herein.

In a salt form of Compound A, various amounts of a mucate salt form of Compound A can be present. For example, the amount of mucate salt of Compound A that can be present in mucate salt Form A can be in the range of about 90% to 100%. In some embodiments, the amount of mucate salt of Compound A that can be present in mucate salt Form A can be in the range of about 95% to 100%. In other embodiments, the amount of mucate salt of Compound A that can be present in mucate salt Form A can be in the range of about 98% to 100%. In still other embodiments, the amount of mucate salt of Compound A that can be present in mucate salt Form A can be in the range of about 95% to 98%. In some embodiments, the amount of mucate salt of Compound A that can be present in mucate salt Form A can be ≥90%. In other embodiments, the amount of mucate salt of Compound A that can be present in mucate salt Form A can be ≥95%. In still other embodiments, the amount of mucate salt of Compound A that can be present in mucate salt Form A can be ≥98%. When less than 100% of a salt form described herein is a mucate salt form of Compound A, one or more of the components selected from the following can be present in the mucate salt form of Compound A (such as mucate salt Form A of Compound A): (1) a freebase of Compound A, such as those described herein, (2) a compound that is the result of the degradation of a mucate salt form of Compound A and/or the degradation of a freebase of Compound A, and (3) an impurity from the synthesis of a mucate salt form of Compound A and/or the synthesis of a freebase of Compound A.

In some embodiments, mucate salt Form A can be characterized by one or more peaks in an XRPD pattern, wherein the one or more peaks can be selected from a peak in the range of about 8.3 degrees to about 8.7 degrees, a peak in the range of about 9.4 degrees to about 9.8 degrees, a peak in the range of about 12.6 degrees to about 13 degrees, a peak in the range of about 13.9 degrees to about 14.3 degrees, a peak in the range of about 16.9 degrees to about 17.3 degrees, a peak in the range of about 19.1 degrees to about 19.5 degrees, a peak in the range of about 19.5 degrees to about 19.9 degrees, a peak in the range of about 21.2 degrees to about 21.6 degrees and a peak in the range of about 25.5 degrees to about 25.9 degrees. In some embodiments, mucate salt Form A can be characterized by one or more peaks in an XRPD pattern, wherein the one or more peaks is selected from a peak in the range of about 4.1 degrees to about 4.5 degrees, a peak in the range of about 6.8 degrees to about 7.2 degrees, a peak in the range of about 8.3 degrees to about 8.7 degrees, a peak in the range of about 9.4 degrees to about 9.8 degrees, a peak in the range of about 9.9 degrees to about 10.3 degrees, a peak in the range of about 10.3 degrees to about 10.7 degrees, a peak in the range of about 11.1 degrees to about 11.5 degrees, a peak in the range of about 12.6 degrees to about 13 degrees, a peak in the range of about 13.9 degrees to about 14.3 degrees, a peak in the range of about 16.9 degrees to about 17.3 degrees, a peak in the range of about 17.4 degrees to about 17.8 degrees, a peak in the range of about 18.6 degrees to about 19 degrees, a peak in the range of about 19.1 degrees to about 19.5 degrees, a peak in the range of about 19.5 degrees to about 19.9 degrees, a peak in the range of about 20.6 degrees to about 21 degrees, a peak in the range of about 21.2 degrees to about 21.6 degrees, a peak in the range of about 22.5 degrees to about 22.9 degrees, a peak in the range of about 25.5 degrees to about 25.9 degrees, a peak in the range of about 26.7 degrees to about 27.1 degrees and a peak in the range of about 30.6 degrees to about 31 degrees.

In some embodiments, mucate salt Form A can be characterized by one or more peaks in an XPRD pattern, wherein the one or more peaks can be selected from about 8.52 degrees, about 9.62 degrees, about 12.78 degrees, about 14.06 degrees, about 17.06 degrees, about 19.3 degrees, about 19.67 degrees, about 21.36 degrees and about 25.69 degrees. In some embodiments, mucate salt Form A can be characterized by one or more peaks in an XRPD pattern, wherein the one or more peaks is selected from about 4.28 degrees, about 7.04 degrees, about 8.52 degrees, about 9.62 degrees, about 10.1 degrees, about 10.53 degrees, about 11.28 degrees, about 12.78 degrees, about 14.06 degrees, about 17.06 degrees, about 17.57 degrees, about 18.78 degrees, about 19.3 degrees, about 19.67 degrees, about 20.75 degrees, about 21.36 degrees, about 22.73 degrees, about 25.69 degrees, about 26.87 degrees and about 30.79 degrees.

Figure 20:
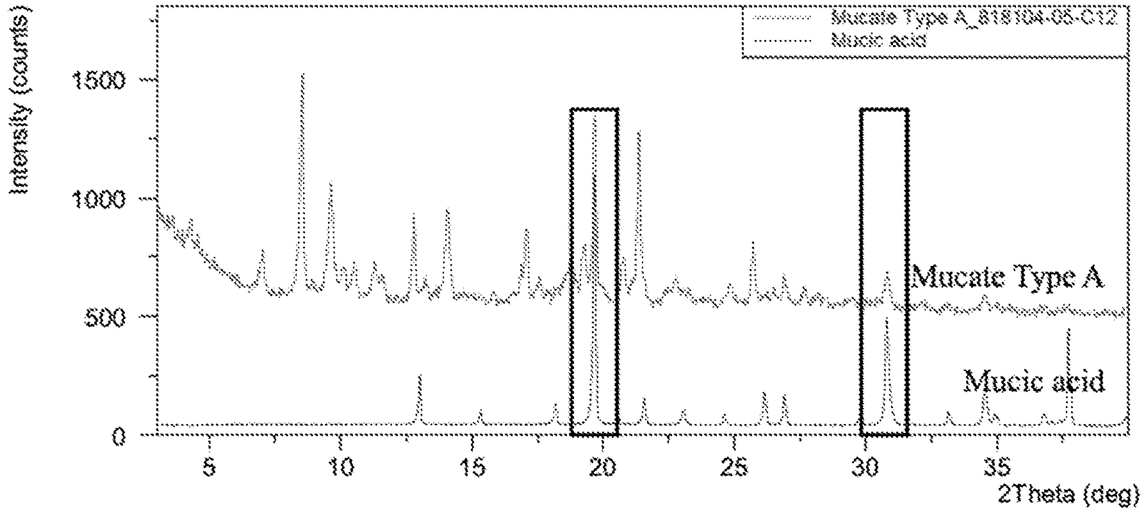
FIG. 20 provides a representative XRPD pattern of mucate salt Form A.

In some embodiments, mucate salt Form A can exhibit an XRPD pattern as shown in FIG. 20.

In some embodiments, mucate salt Form A can be characterized by one or more peaks in an XRPD pattern selected from:

| Peak | 2θ | Relative Intensity [%] |
|---|---|---|
| 1 | 4.28 | 12.62 |
| 2 | 7.04 | 17.62 |
| 3 | 8.52 | 100.00 |
| 4 | 9.62 | 50.90 |
| 5 | 10.10 | 12.51 |
| 6 | 10.53 | 13.58 |
| 7 | 11.28 | 15.10 |
| 8 | 11.60 | 8.08 |
| 9 | 12.78 | 37.27 |
| 10 | 13.24 | 8.98 |
| 11 | 14.06 | 40.78 |
| 12 | 15.80 | 3.76 |
| 13 | 17.06 | 32.64 |
| 14 | 17.57 | 9.99 |
| 15 | 18.78 | 23.61 |
| 16 | 19.30 | 26.99 |
| 17 | 19.67 | 84.83 |
| 18 | 20.75 | 19.84 |
| 19 | 21.36 | 80.37 |
| 20 | 22.73 | 12.18 |
| 21 | 24.78 | 8.35 |
| 22 | 25.69 | 29.49 |
| 23 | 26.87 | 14.27 |
| 24 | 27.65 | 8.54 |
| 25 | 28.26 | 4.00 |
| 26 | 29.45 | 3.85 |
| 27 | 30.79 | 15.99 |
| 28 | 32.20 | 2.62 |
| 29 | 33.13 | 2.35 |
| 30 | 34.52 | 7.48 |
| 31 | 36.74 | 2.19 |
| 32 | 37.64 | 2.76 |

Figure 21:
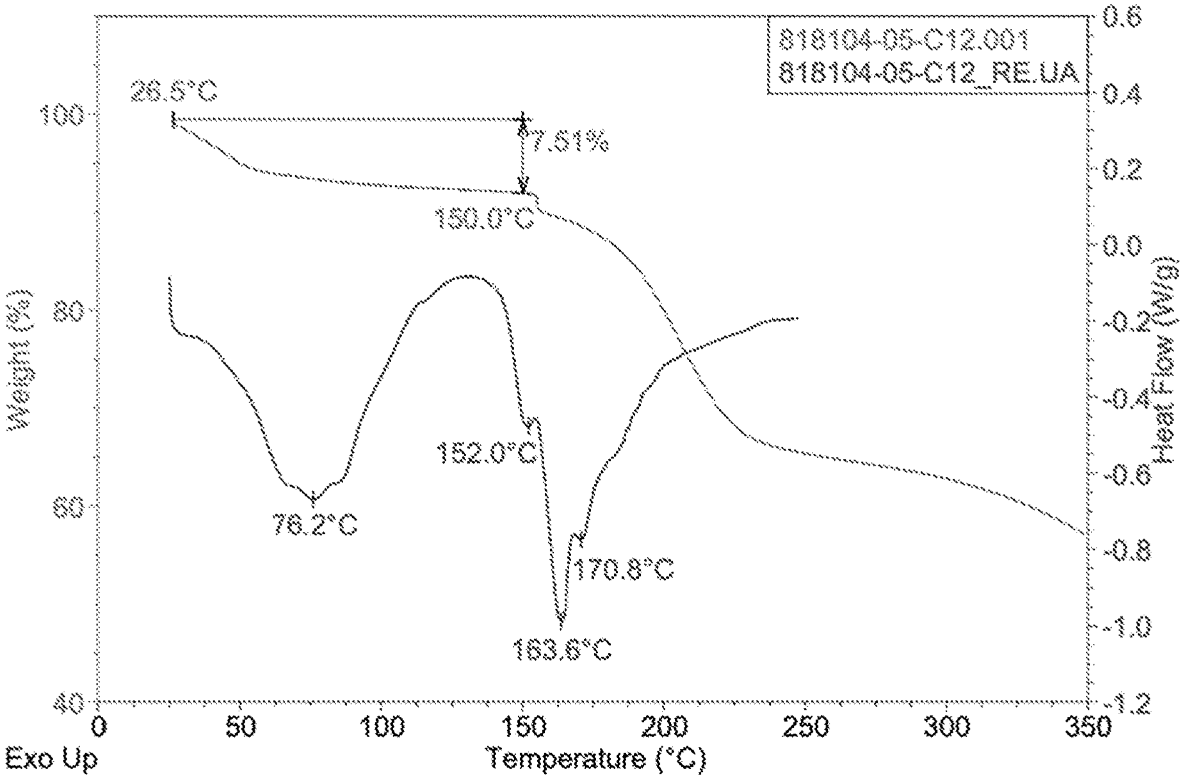
FIG. 21 provides a representative DSC and TGA thermogram of mucate salt Form A.

Mucate salt Form A can also be characterized by DSC and/or TGA. In some embodiments, mucate salt Form A can be characterized by a DSC and/or TGA thermogram of FIG. 21. In some embodiments, mucate salt Form A can be characterized by a weight loss of about 7.5% when heated from about 26° C. to about 150° C. In some embodiments, mucate salt Form A can be characterized by a first endotherm in the range of about 72° C. to about 80° C., a second endotherm in the range of about 148° C. to about 156° C., a third endotherm in the range of about 160° C. to about 168° C. and a fourth endotherm in the range of about 167° C. to about 175° C. In some embodiments, mucate salt Form A can be characterized by a first endotherm in the range of about 74° C. to about 78° C., a second endotherm in the range of about 150° C. to about 154° C., a third endotherm in the range of about 162° C. to about 166° C. and a fourth endotherm in the range of about 169° C. to about 173° C. In some embodiments, mucate salt Form A can be characterized by a first endotherm at about 76.2° C., a second endotherm at about 152.0° C., a third endotherm at about 163.6° C. and a fourth endotherm at about 170.8° C.

Some embodiments disclosed herein relate to a pharmaceutically acceptable salt of Compound A, wherein the pharmaceutically acceptable salt can be a hippurate salt. In some embodiments, a hippurate salt form can be hippurate Form A. In some embodiments, the molar ratio of hippurate acid to Compound A may be from about 0.6 to about 1.4, from about 0.8 to about 1.2, from about 0.9 to about 1.1 or about 1.

A variety of hippurate salt forms of Compound A can be obtained. In some embodiments, a hippurate salt form described herein can further include a freebase of Compound A. For example, hippurate salt Form A may further include a small amount of freebase Form A. In some embodiments, a hippurate salt form described herein can further include a small amount of one or more other hippurate salt forms, such as those described herein.

In a salt form of Compound A, various amounts of a hippurate salt form of Compound A can be present. For example, the amount of hippurate salt of Compound A that can be present in hippurate salt Form A can be in the range of about 90% to 100%. In some embodiments, the amount of hippurate salt of Compound A that can be present in hippurate salt Form A can be in the range of about 95% to 100%. In other embodiments, the amount of hippurate salt of Compound A that can be present in hippurate salt Form A can be in the range of about 98% to 100%. In still other embodiments, the amount of hippurate salt of Compound A that can be present in hippurate salt Form A can be in the range of about 95% to 98%. In some embodiments, the amount of hippurate salt of Compound A that can be present in hippurate salt Form A can be ≥90%. In other embodiments, the amount of hippurate salt of Compound A that can be present in hippurate salt Form A can be ≥95%. In still other embodiments, the amount of hippurate salt of Compound A that can be present in hippurate salt Form A can be ≥98%. When less than 100% of a salt form described herein is a hippurate salt of Compound A, one or more of the components selected from the following can be present in the hippurate salt form of Compound A (such as hippurate salt Form A of Compound A): (1) a freebase of Compound A (including those described herein), (2) a compound that is the result of the degradation of a hippurate salt form of Compound A and/or the degradation of a freebase of Compound A, and (3) an impurity from the synthesis of a hippurate salt form of Compound A and/or the synthesis of a freebase of Compound A.

In some embodiments, hippurate salt Form A can be characterized by one or more peaks in an XRPD pattern, wherein the one or more peaks can be selected from a peak in the range of about 5.5 degrees to about 5.9 degrees, a peak in the range of about 6.7 degrees to about 7.1 degrees, a peak in the range of about 7.9 degrees to about 8.3 degrees, a peak in the range of about 9.5 degrees to about 9.9 degrees, a peak in the range of about 15.9 degrees to about 16.3 degrees, a peak in the range of about 16.9 degrees to about 17.3 degrees, a peak in the range of about 18.3 degrees to about 18.7 degrees and a peak in the range of about 22.4 degrees to about 22.8 degrees. In some embodiments, hippurate salt Form A can be characterized by one or more peaks in an XRPD pattern, wherein the one or more peaks is selected from a peak in the range of about 5.5 degrees to about 5.9 degrees, a peak in the range of about 6.7 degrees to about 7.1 degrees, a peak in the range of about 7.9 degrees to about 8.3 degrees, a peak in the range of about 9.5 degrees to about 9.9 degrees, a peak in the range of about 11.2 degrees to about 11.6 degrees, a peak in the range of about 14.6 degrees to about 15 degrees, a peak in the range of about 15.9 degrees to about 16.3 degrees, a peak in the range of about 16.9 degrees to about 17.3 degrees, a peak in the range of about 18.3 degrees to about 18.7 degrees, a peak in the range of about 20.4 degrees to about 20.8 degrees, a peak in the range of about 21.2 degrees to about 21.6 degrees, a peak in the range of about 21.7 degrees to about 22.1 degrees, a peak in the range of about 22.4 degrees to about 22.8 degrees, a peak in the range of about 22.7 degrees to about 23.1 degrees, a peak in the range of about 23 degrees to about 23.4 degrees, a peak in the range of about 23.2 degrees to about 23.6 degrees, a peak in the range of about 23.6 degrees to about 24 degrees and a peak in the range of about 24.1 degrees to about 24.5 degrees.

In some embodiments, hippurate salt Form A can be characterized by one or more peaks in an XPRD pattern, wherein the one or more peaks can be selected from about 5.69 degrees, about 6.85 degrees, about 8.05 degrees, about 9.69 degrees, about 16.12 degrees, about 17.1 degrees, about 18.53 degrees and about 22.6 degrees. In some embodiments, hippurate salt Form A can be characterized by one or more peaks in an XRPD pattern, wherein the one or more peaks is selected from about 5.69 degrees, about 6.85 degrees, about 8.05 degrees, about 9.69 degrees, about 11.38 degrees, about 14.83 degrees, about 16.12 degrees, about 17.1 degrees, about 18.53 degrees, about 20.64 degrees, about 21.35 degrees, about 21.87 degrees, about 22.6 degrees, about 22.85 degrees, about 23.22 degrees, about 23.39 degrees, about 23.81 degrees and about 24.27 degrees.

Figure 22:
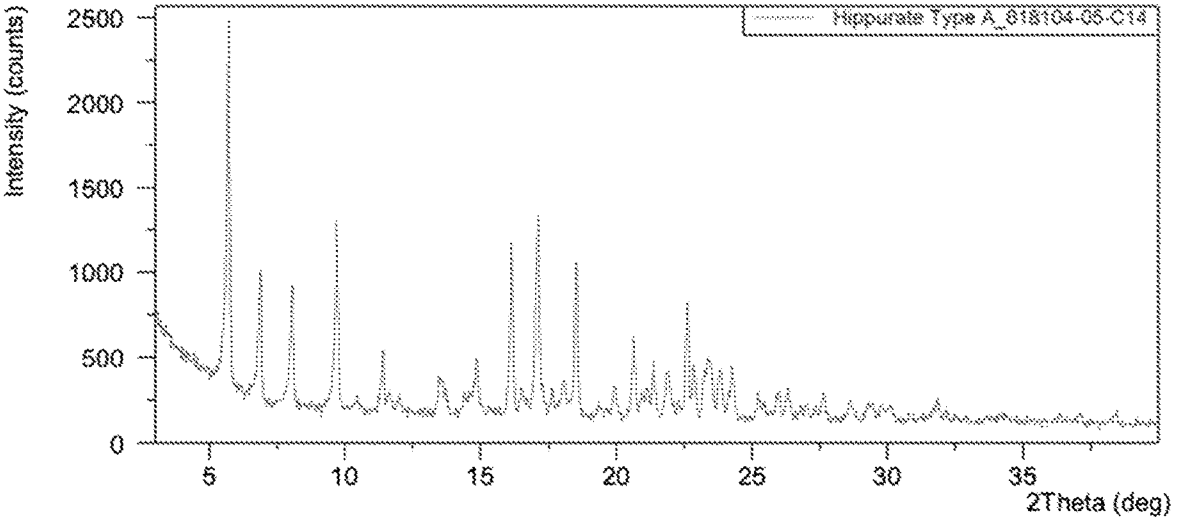
FIG. 22 provides a representative XRPD pattern of hippurate salt Form A.

In some embodiments, hippurate salt Form A can exhibit an XRPD pattern as shown in FIG. 22.

In some embodiments, hippurate salt Form A can be characterized by one or more peaks in an XRPD pattern selected from:

| Peak | 2θ | Relative Intensity [%] |
|---|---|---|
| 1 | 5.69 | 100.00 |
| 2 | 6.85 | 33.45 |
| 3 | 8.05 | 33.87 |
| 4 | 9.69 | 49.56 |
| 5 | 10.41 | 3.29 |
| 6 | 11.38 | 16.60 |
| 7 | 11.62 | 5.45 |
| 8 | 12.01 | 4.53 |
| 9 | 13.48 | 8.58 |
| 10 | 14.36 | 4.30 |
| 11 | 14.83 | 14.83 |
| 12 | 16.12 | 47.93 |
| 13 | 16.49 | 6.66 |
| 14 | 17.10 | 52.50 |
| 15 | 17.62 | 6.82 |

-continued

| Peak | 2θ | Relative Intensity [%] |
|---|---|---|
| 16 | 18.03 | 9.28 |
| 17 | 18.53 | 43.24 |
| 18 | 19.36 | 2.75 |
| 19 | 19.92 | 7.92 |
| 20 | 20.64 | 20.47 |
| 21 | 21.15 | 7.12 |
| 22 | 21.35 | 13.57 |
| 23 | 21.87 | 12.50 |
| 24 | 22.60 | 30.33 |
| 25 | 22.85 | 13.69 |
| 26 | 23.22 | 12.43 |
| 27 | 23.39 | 15.83 |
| 28 | 23.81 | 13.45 |
| 29 | 24.27 | 13.32 |
| 30 | 25.21 | 6.64 |
| 31 | 25.99 | 6.95 |
| 32 | 26.30 | 8.66 |
| 33 | 26.74 | 3.68 |
| 34 | 27.00 | 3.90 |
| 35 | 27.62 | 6.52 |
| 36 | 28.56 | 4.73 |
| 37 | 29.40 | 3.89 |
| 38 | 30.10 | 4.03 |
| 39 | 31.78 | 4.45 |
| 40 | 34.28 | 1.60 |
| 41 | 37.10 | 2.31 |
| 42 | 38.39 | 3.01 |

Figure 23:
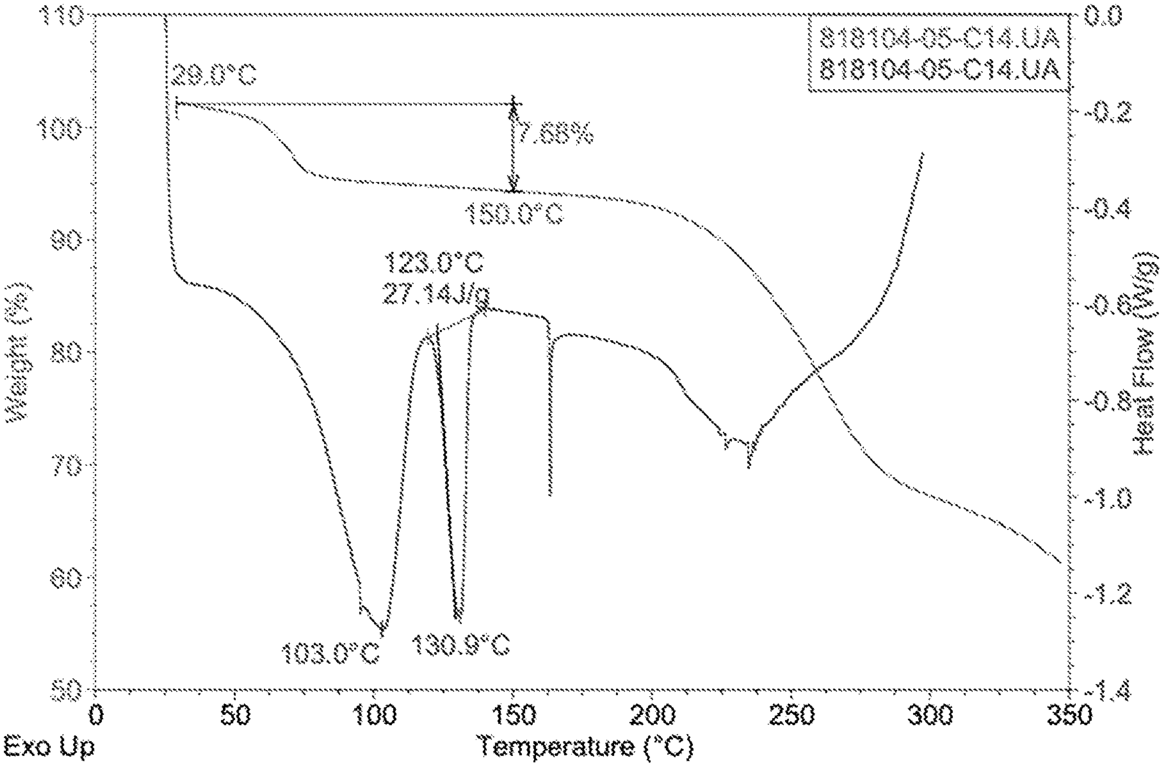
FIG. 23 provides a representative DSC and TGA thermogram of hippurate salt Form A.

Hippurate salt Form A can also be characterized by DSC and/or TGA. In some embodiments, hippurate salt Form A can be characterized by a DSC and/or TGA thermogram of FIG. 23. In some embodiments, hippurate salt Form A can be characterized by a weight loss of about 7.7% when heated from about 29° C. to about 150° C. In some embodiments, hippurate salt Form A can be characterized by a first endotherm in the range of about 99° C. to about 107° C. and a second endotherm in the range of about 127° C. to about 135° C. In some embodiments, hippurate salt Form A can be characterized by a first endotherm in the range of about 101° C. to about 105° C. and a second endotherm in the range of about 129° C. to about 161° C. In some embodiments, hippurate salt Form A can be characterized by a first endotherm at about 103.0° C. and a second endotherm at about 130.9° C.

Freebase Form A of Compound A can also be characterized by various methods such as those described herein. In some embodiments, freebase Form A of Compound A can be characterized by one or more peaks in an XRPD pattern, wherein the one or more peaks can be selected from a peak in the range of about 4.7 degrees to about 5.1 degrees, a peak in the range of about 5 degrees to about 5.4 degrees and a peak in the range of about 5.3 degrees to about 5.7 degrees. In some embodiments, freebase Form A of Compound A can be characterized by one or more peaks in an XRPD pattern, wherein the one or more peaks can be selected from a peak in the range of about 4.7 degrees to about 5.1 degrees, a peak in the range of about 5 degrees to about 5.4 degrees, a peak in the range of about 5.3 degrees to about 5.7 degrees and a peak in the range of about 10.3 degrees to about 10.7 degrees.

In some embodiments, freebase Form A of Compound A can be characterized by one or more peaks in an XPRD pattern, wherein the one or more peaks can be selected from about 4.92 degrees, about 5.24 degrees and about 5.51 degrees. In some embodiments, freebase Form A of Compound A can be characterized by one or more peaks in an XPRD pattern, wherein the one or more peaks can be selected from about 4.92 degrees, about 5.24 degrees, about 5.51 degrees and about 10.45 degrees.

Figure 24:
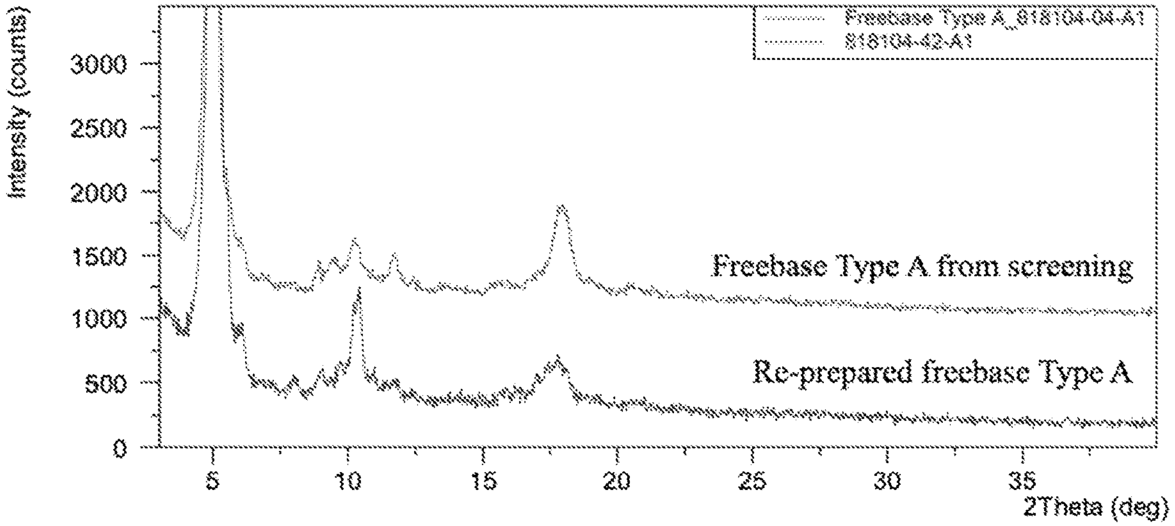
FIG. 24 provides a representative XRPD pattern of freebase Form A of Compound A.

In some embodiments, freebase Form A of Compound A can exhibit an XRPD pattern as shown in FIG. 24. In some embodiments, freebase Form A of Compound A can be characterized by one or more peaks in an XRPD pattern selected from:

| Peak | 2θ | Relative Intensity [%] |
|---|---|---|
| 1 | 4.92 | 99.97 |
| 2 | 5.24 | 100.00 |
| 3 | 5.51 | 30.94 |
| 4 | 6.10 | 6.96 |
| 5 | 8.05 | 2.23 |
| 6 | 9.00 | 4.31 |
| 7 | 9.72 | 6.21 |
| 8 | 10.45 | 17.62 |
| 9 | 11.77 | 3.05 |
| 10 | 15.90 | 1.75 |
| 11 | 16.97 | 5.41 |
| 12 | 17.95 | 6.92 |
| 13 | 20.71 | 1.21 |

Figure 25:
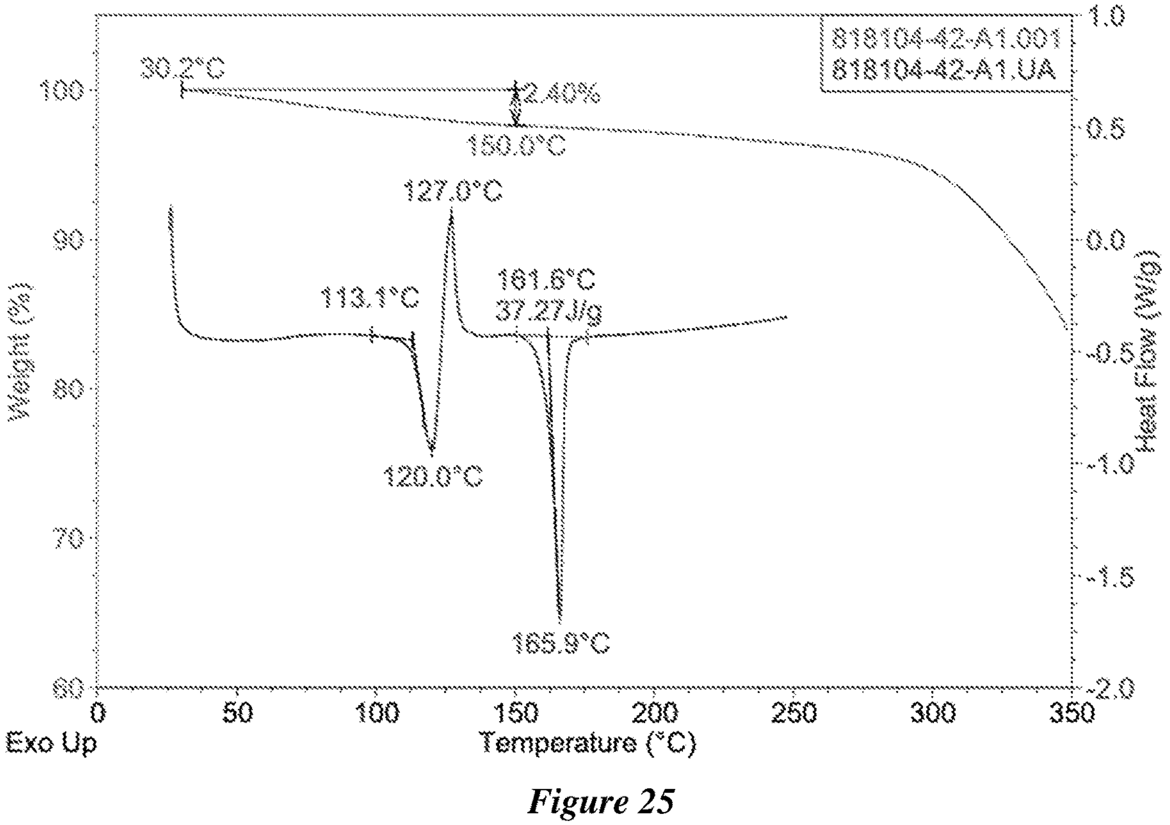
FIG. 25 provides a representative DSC and TGA thermogram of freebase Form A of Compound A.

In some embodiments, freebase Form A of Compound A can be characterized by a DSC and/or TGA thermogram. In some embodiments, freebase Form A of Compound A can be characterized by a weight loss of about 2.4% when heated from about 30° C. to about 150° C. In some embodiments, freebase Form A of Compound A can be characterized by a first endotherm in the range of about 116° C. and about 124° C. and a second endotherm in the range of about 162° C. and about 170° C. In some embodiments, freebase Form A of Compound A can be characterized by a first endotherm in the range of about 118° C. and about 122° C. and a second endotherm in the range of about 164° C. and about 168° C. In some embodiments, freebase Form A of Compound A can be characterized by a first endotherm at about 120.0° C. and a second endotherm at about 165.9° C. In some embodiments, freebase Form A of Compound A can have a DSC and/or TGA thermogram of FIG. 25.

Freebase Form B of Compound A can also be characterized by various methods such as those described herein. In some embodiments, freebase Form B of Compound A can be characterized by one or more peaks in an XRPD pattern, wherein the one or more peaks can be selected from a peak in the range of about 5.2 degrees to about 5.6 degrees, a peak in the range of about 9.3 degrees to about 9.7 degrees, a peak in the range of about 11.5 degrees to about 11.9 degrees, a peak in the range of about 12 degrees to about 12.4 degrees, a peak in the range of about 14 degrees to about 14.4 degrees, a peak in the range of about 16.2 degrees to about 16.6 degrees, a peak in the range of about 16.9 degrees to about 17.3 degrees, a peak in the range of about 17.9 degrees to about 18.3 degrees, a peak in the range of about 19.8 degrees to about 20.2 degrees, a peak in the range of about 20.9 degrees to about 21.3 degrees, a peak in the range of about 24.2 degrees to about 24.6 degrees and a peak in the range of about 24.7 degrees to about 25.1 degrees. In some embodiments, freebase Form B of Compound A can be characterized by one or more peaks in an XRPD pattern, wherein the one or more peaks can be selected from a peak in the range of about 5.2 degrees to about 5.6 degrees, a peak in the range of about 9.3 degrees to about 9.7 degrees, a peak in the range of about 10.5 degrees to about 10.9 degrees, a peak in the range of about 11.1 degrees to about 11.5 degrees, a peak in the range of about 11.5 degrees to about 11.9 degrees, a peak in the range of about 12 degrees to about 12.4 degrees, a peak in the range of about 13.5 degrees to about 13.9 degrees, a peak in the range of about 14 degrees to about 14.4 degrees, a peak in the range of about 14.8 degrees to about 15.2 degrees, a peak in the range of about 16.2 degrees to about 16.6 degrees, a peak in the range of about 16.9 degrees to about 17.3 degrees, a peak in the range of about 17.9 degrees to about 18.3 degrees, a peak in the range of about 18.5 degrees to about 18.9 degrees, a peak in the range of about 18.9 degrees to about 19.3 degrees, a peak in the range of about 19.3 degrees to about 19.7 degrees, a peak in the range of about 19.8 degrees to about 20.2 degrees, a peak in the range of about 20.9 degrees to about 21.3 degrees, a peak in the range of about 21.8 degrees to about 22.2 degrees, a peak in the range of about 23.6 degrees to about 24 degrees, a peak in the range of about 24.2 degrees to about 24.6 degrees, a peak in the range of about 24.7 degrees to about 25.1 degrees and a peak in the range of about 26.5 degrees to about 26.9 degrees.

In some embodiments, freebase Form B of Compound A can be characterized by one or more peaks in an XPRD pattern, wherein the one or more peaks can be selected from about 5.44 degrees, about 9.52 degrees, about 11.72 degrees, about 12.23 degrees, about 14.17 degrees, about 16.42 degrees, about 17.1 degrees, about 18.14 degrees, about 20.02 degrees, about 21.09 degrees, about 24.39 degrees and about 24.86 degrees. In some embodiments, freebase Form B of Compound A can be characterized by one or more peaks in an XPRD pattern, wherein the one or more peaks can be selected from about 5.44 degrees, about 9.52 degrees, about 10.73 degrees, about 11.28 degrees, about 11.72 degrees, about 12.23 degrees, about 13.65 degrees, about 14.17 degrees, about 15 degrees, about 16.42 degrees, about 17.1 degrees, about 18.14 degrees, about 18.66 degrees, about 19.14 degrees, about 19.52 degrees, about 20.02 degrees, about 21.09 degrees, about 21.97 degrees, about 23.84 degrees, about 24.39 degrees, about 24.86 degrees and about 26.65 degrees.

Figure 26:
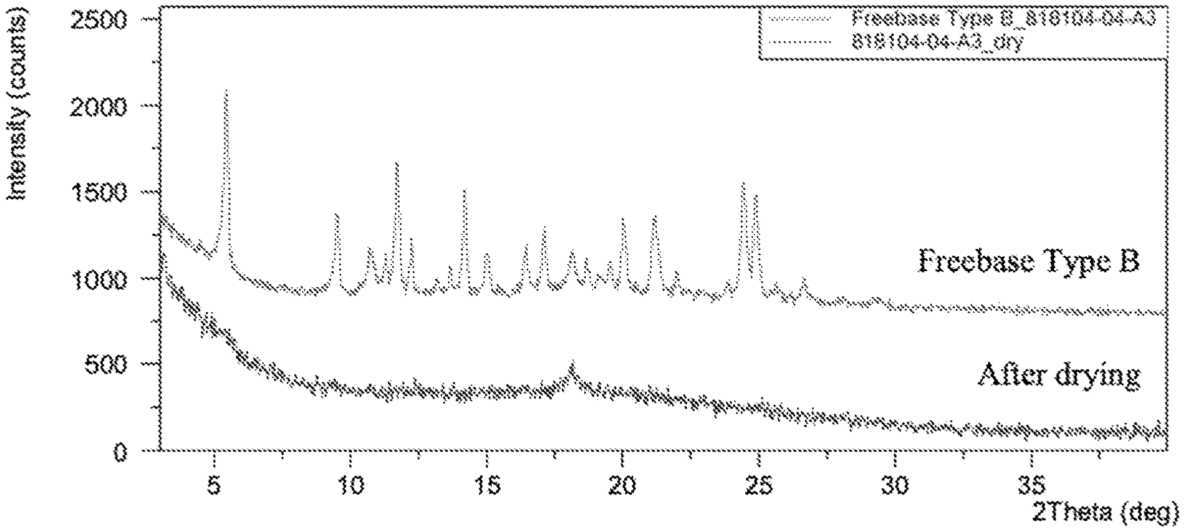
FIG. 26 provides a representative XRPD pattern of freebase Form B of Compound A.

In some embodiments, freebase Form B of Compound A can exhibit an XRPD pattern as shown in FIG. 26. In some embodiments, freebase Form B of Compound A can be characterized by one or more peaks in an XRPD pattern selected from:

| Peak | 2θ | Relative Intensity [%] |
|---|---|---|
| 1 | 5.44 | 100.00 |
| 2 | 9.52 | 42.66 |
| 3 | 10.73 | 23.87 |
| 4 | 11.28 | 17.84 |
| 5 | 11.72 | 72.20 |
| 6 | 12.23 | 30.57 |
| 7 | 13.18 | 8.38 |
| 8 | 13.65 | 16.13 |
| 9 | 14.17 | 60.39 |
| 10 | 15.00 | 24.47 |
| 11 | 16.42 | 28.75 |
| 12 | 17.10 | 39.25 |
| 13 | 18.14 | 27.09 |
| 14 | 18.66 | 22.80 |
| 15 | 19.14 | 13.22 |
| 16 | 19.52 | 21.47 |
| 17 | 20.02 | 45.07 |
| 18 | 21.09 | 43.60 |
| 19 | 21.97 | 14.90 |
| 20 | 23.84 | 10.59 |
| 21 | 24.39 | 68.32 |
| 22 | 24.86 | 62.25 |
| 23 | 25.64 | 9.67 |
| 24 | 26.65 | 14.93 |
| 25 | 29.38 | 4.46 |

Freebase Form C of Compound A can also be characterized by various methods such as those described herein. In some embodiments, freebase Form C of Compound A can be characterized by one or more peaks in an XRPD pattern, wherein the one or more peaks can be selected from a peak in the range of about 4.8 degrees to about 5.2 degrees, a peak in the range of about 10.1 degrees to about 10.5 degrees, a peak in the range of about 11.1 degrees to about 11.5 degrees, a peak in the range of about 11.6 degrees to about 12 degrees, a peak in the range of about 12.3 degrees to about 12.7 degrees, a peak in the range of about 13.5 degrees to about 13.9 degrees, a peak in the range of about 14.4 degrees to about 14.8 degrees, a peak in the range of about 14.7 degrees to about 15.1 degrees, a peak in the range of about 15.7 degrees to about 16.1 degrees, a peak in the range of about 16.2 degrees to about 16.6 degrees, a peak in the range of about 17.9 degrees to about 18.3 degrees, a peak in the range of about 18.7 degrees to about 19.1 degrees, a peak in the range of about 21.1 degrees to about 21.5 degrees and a peak in the range of about 21.5 degrees to about 21.9 degrees. In some embodiments, freebase Form C of Compound A can be characterized by one or more peaks in an XRPD pattern, wherein the one or more peaks can be selected from a peak in the range of about 4.8 degrees to about 5.2 degrees, a peak in the range of about 6.1 degrees to about 6.5 degrees, a peak in the range of about 7.7 degrees to about 8.1 degrees, a peak in the range of about 8.6 degrees to about 9 degrees, a peak in the range of about 10.1 degrees to about 10.5 degrees, a peak in the range of about 11.1 degrees to about 11.5 degrees, a peak in the range of about 11.6 degrees to about 12 degrees, a peak in the range of about 11.9 degrees to about 12.3 degrees, a peak in the range of about 12.3 degrees to about 12.7 degrees, a peak in the range of about 12.6 degrees to about 13 degrees, a peak in the range of about 13.5 degrees to about 13.9 degrees, a peak in the range of about 14.4 degrees to about 14.8 degrees, a peak in the range of about 14.7 degrees to about 15.1 degrees, a peak in the range of about 15.7 degrees to about 16.1 degrees, a peak in the range of about 16.2 degrees to about 16.6 degrees, a peak in the range of about 17.5 degrees to about 17.9 degrees, a peak in the range of about 17.9 degrees to about 18.3 degrees, a peak in the range of about 18.7 degrees to about 19.1 degrees, a peak in the range of about 19.5 degrees to about 19.9 degrees, a peak in the range of about 19.7 degrees to about 20.1 degrees, a peak in the range of about 20.6 degrees to about 21 degrees, a peak in the range of about 21.1 degrees to about 21.5 degrees, a peak in the range of about 21.5 degrees to about 21.9 degrees, a peak in the range of about 24.3 degrees to about 24.7 degrees, a peak in the range of about 25.4 degrees to about 25.8 degrees and a peak in the range of about 26.9 degrees to about 27.3 degrees.

In some embodiments, freebase Form C of Compound A can be characterized by one or more peaks in an XPRD pattern, wherein the one or more peaks can be selected from about 5.01 degrees, about 10.32 degrees, about 11.25 degrees, about 11.83 degrees, about 12.46 degrees, about 13.73 degrees, about 14.57 degrees, about 14.92 degrees, about 15.87 degrees, about 16.37 degrees, about 18.06 degrees, about 18.87 degrees, about 21.25 degrees and about 21.65 degrees. In some embodiments, freebase Form C of Compound A can be characterized by one or more peaks in an XPRD pattern, wherein the one or more peaks can be selected from about 5.01 degrees, about 6.28 degrees, about 7.92 degrees, about 8.81 degrees, about 10.32 degrees, about 11.25 degrees, about 11.83 degrees, about 12.09 degrees, about 12.46 degrees, about 12.75 degrees, about 13.73 degrees, about 14.57 degrees, about 14.92 degrees, about 15.87 degrees, about 16.37 degrees, about 17.67 degrees, about 18.06 degrees, about 18.87 degrees, about 19.68 degrees, about 19.91 degrees, about 20.82 degrees, about 21.25 degrees, about 21.65 degrees, about 24.5 degrees, about 25.62 degrees and about 27.11 degrees.

Figure 27:
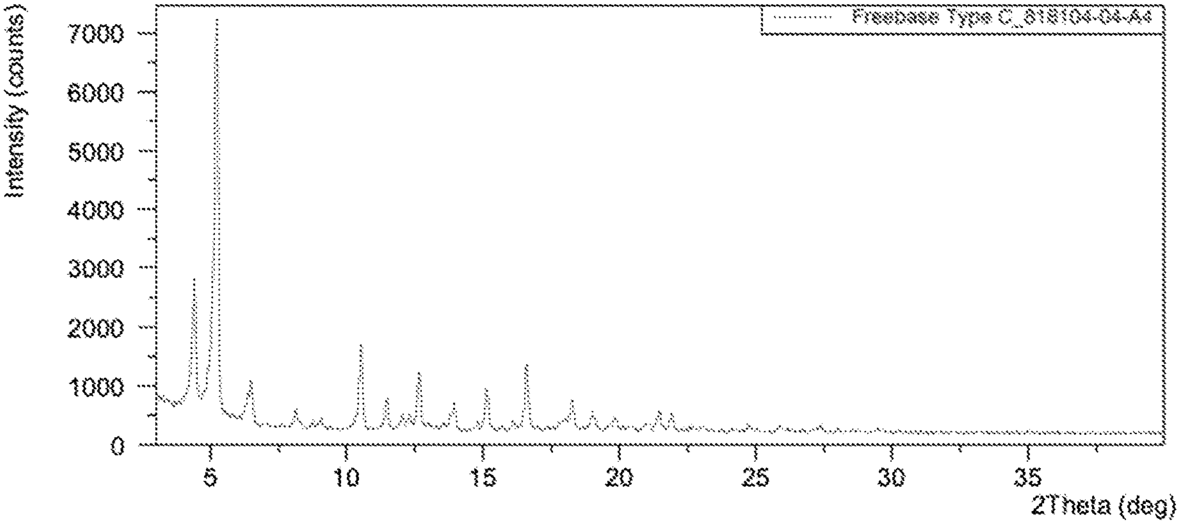
FIG. 27 provides a representative XRPD pattern of freebase Form C of Compound A.

In some embodiments, freebase Form C of Compound A can exhibit an XRPD pattern as shown in FIG. 27. In some embodiments, freebase Form C of Compound A can be characterized by one or more peaks in an XRPD pattern selected from:

| Peak | 2θ | Relative Intensity [%] |
|---|---|---|
| 1 | 5.01 | 68.96 |
| 2 | 6.28 | 24.19 |
| 3 | 7.92 | 10.49 |
| 4 | 8.81 | 19.28 |
| 5 | 10.32 | 100.00 |
| 6 | 11.25 | 37.58 |
| 7 | 11.83 | 27.48 |
| 8 | 12.09 | 22.25 |
| 9 | 12.46 | 63.64 |
| 10 | 12.75 | 22.31 |
| 11 | 13.73 | 34.70 |
| 12 | 14.57 | 26.28 |
| 13 | 14.92 | 64.15 |
| 14 | 15.87 | 29.03 |
| 15 | 16.37 | 63.69 |
| 16 | 17.67 | 24.06 |
| 17 | 18.06 | 49.32 |
| 18 | 18.87 | 37.80 |
| 19 | 19.68 | 24.72 |
| 20 | 19.91 | 16.08 |
| 21 | 20.82 | 19.76 |
| 22 | 21.25 | 38.90 |
| 23 | 21.65 | 45.26 |
| 24 | 24.50 | 22.75 |
| 25 | 25.62 | 23.36 |
| 26 | 27.11 | 12.11 |
| 27 | 29.30 | 4.76 |
| 28 | 34.92 | 2.44 |

In some embodiments, freebase Form C of Compound A can be characterized by a DSC and/or TGA thermogram. In some embodiments, freebase Form C of Compound A can be characterized by a weight loss of about 3.7% when heated from about 28° C. to about 150° C. In some embodiments, freebase Form C of Compound A can be characterized by a first endotherm in the range of about 149° C. and about 157° C. and a second endotherm in the range of about 162° C. and about 170° C. In some embodiments, freebase Form C of Compound A can be characterized by a first endotherm in the range of about 151° C. and about 155° C. and a second endotherm in the range of about 164° C. and about 168° C. In some embodiments, freebase Form C of Compound A can be characterized by a first endotherm at about 153.1° C. and a second endotherm at about 165.9° C.

Figure 28:
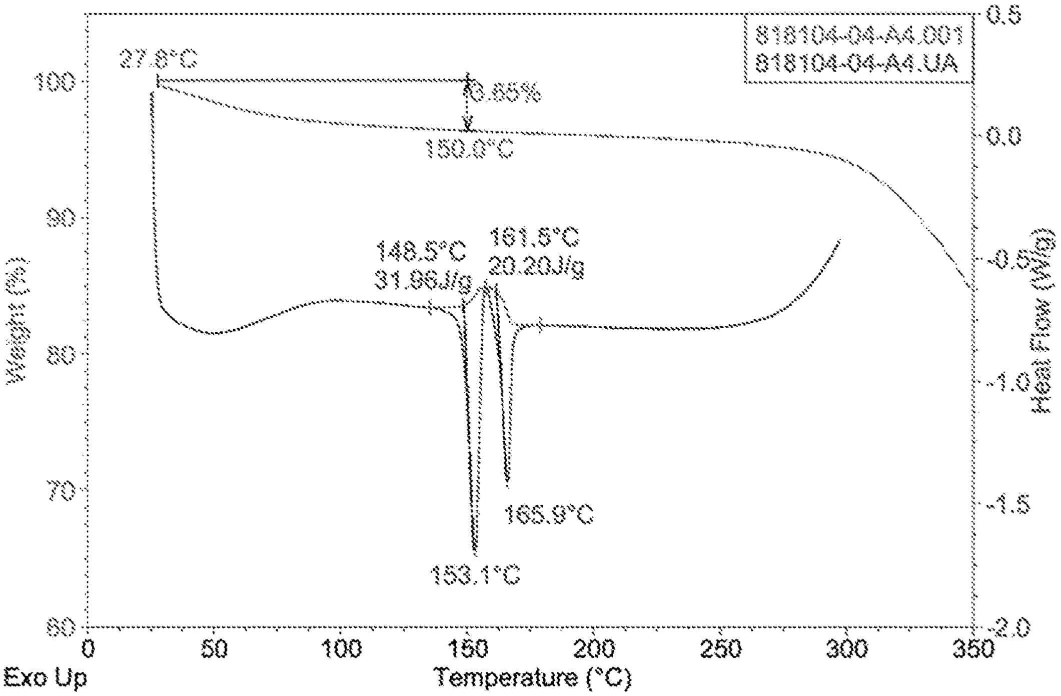
FIG. 28 provides a representative DSC and TGA thermogram of freebase Form C of Compound A.

In other embodiments, freebase Form C of Compound A can be characterized by a first endotherm in the range of about 147° C. and about 155° C. and a second endotherm in the range of about 161° C. and about 169° C. In some embodiments, freebase Form C of Compound A can be characterized by a first endotherm in the range of about 149° C. and about 153° C. and a second endotherm in the range of about 163° C. and about 166° C. In some embodiments, freebase Form C of Compound A can be characterized by a first endotherm at about 150.9° C. and a second endotherm at about 164.6° C. In some embodiments, freebase Form C of Compound A can have a DSC and/or TGA thermogram of FIG. 28.

Freebase Form D of Compound A can also be characterized by various methods such as those described herein. In some embodiments, freebase Form D of Compound A can be characterized by one or more peaks in an XRPD pattern, wherein the one or more peaks can be selected from a peak in the range of about 4.2 degrees to about 4.6 degrees, a peak in the range of about 4.4 degrees to about 4.8 degrees, a peak in the range of about 4.7 degrees to about 5.1 degrees, a peak in the range of about 8.5 degrees to about 8.9 degrees, a peak in the range of about 9 degrees to about 9.4 degrees, a peak in the range of about 9.7 degrees to about 10.1 degrees, a peak in the range of about 10.2 degrees to about 10.6 degrees, a peak in the range of about 11.5 degrees to about 11.9 degrees, a peak in the range of about 12 degrees to about 12.4 degrees, a peak in the range of about 14.8 degrees to about 15.2 degrees, a peak in the range of about 15.6 degrees to about 16 degrees, a peak in the range of about 16.3 degrees to about 16.7 degrees, a peak in the range of about 17.3 degrees to about 17.7 degrees, a peak in the range of about 17.6 degrees to about 18 degrees, a peak in the range of about 18.4 degrees to about 18.8 degrees and a peak in the range of about 20 degrees to about 20.4 degrees. In some embodiments, freebase Form D of Compound A can be characterized by one or more peaks in an XRPD pattern, wherein the one or more peaks can be selected from a peak in the range of about 3.8 degrees to about 4.2 degrees, a peak in the range of about 4.2 degrees to about 4.6 degrees, a peak in the range of about 4.4 degrees to about 4.8 degrees, a peak in the range of about 4.7 degrees to about 5.1 degrees, a peak in the range of about 5.5 degrees to about 5.9 degrees, a peak in the range of about 6.5 degrees to about 6.9 degrees, a peak in the range of about 8.5 degrees to about 8.9 degrees, a peak in the range of about 9 degrees to about 9.4 degrees, a peak in the range of about 9.7 degrees to about 10.1 degrees, a peak in the range of about 10.2 degrees to about 10.6 degrees, a peak in the range of about 11.5 degrees to about 11.9 degrees, a peak in the range of about 12 degrees to about 12.4 degrees, a peak in the range of about 13.2 degrees to about 13.6 degrees, a peak in the range of about 14.3 degrees to about 14.7 degrees, a peak in the range of about 14.8 degrees to about 15.2 degrees, a peak in the range of about 15.6 degrees to about 16 degrees, a peak in the range of about 16.3 degrees to about 16.7 degrees, a peak in the range of about 17.3 degrees to about 17.7 degrees, a peak in the range of about 17.6 degrees to about 18 degrees, a peak in the range of about 18.4 degrees to about 18.8 degrees and a peak in the range of about 20 degrees to about 20.4 degrees.

In some embodiments, freebase Form D of Compound A can be characterized by one or more peaks in an XPRD pattern, wherein the one or more peaks can be selected from about 4.37 degrees, about 4.57 degrees, about 4.93 degrees, about 8.65 degrees, about 9.21 degrees, about 9.94 degrees, about 10.35 degrees, about 11.71 degrees, about 12.2 degrees, about 14.96 degrees, about 15.75 degrees, about 16.45 degrees, about 17.46 degrees, about 17.8 degrees, about 18.62 degrees and about 20.21 degrees. In some embodiments, freebase Form D of Compound A can be characterized by one or more peaks in an XPRD pattern, wherein the one or more peaks can be selected from about 4.02 degrees, about 4.37 degrees, about 4.57 degrees, about 4.93 degrees, about 5.74 degrees, about 6.67 degrees, about 8.65 degrees, about 9.21 degrees, about 9.94 degrees, about 10.35 degrees, about 11.71 degrees, about 12.2 degrees, about 13.4 degrees, about 14.5 degrees, about 14.96 degrees, about 15.75 degrees, about 16.45 degrees, about 17.46 degrees, about 17.8 degrees, about 18.62 degrees and about 20.21 degrees.

Figure 29:
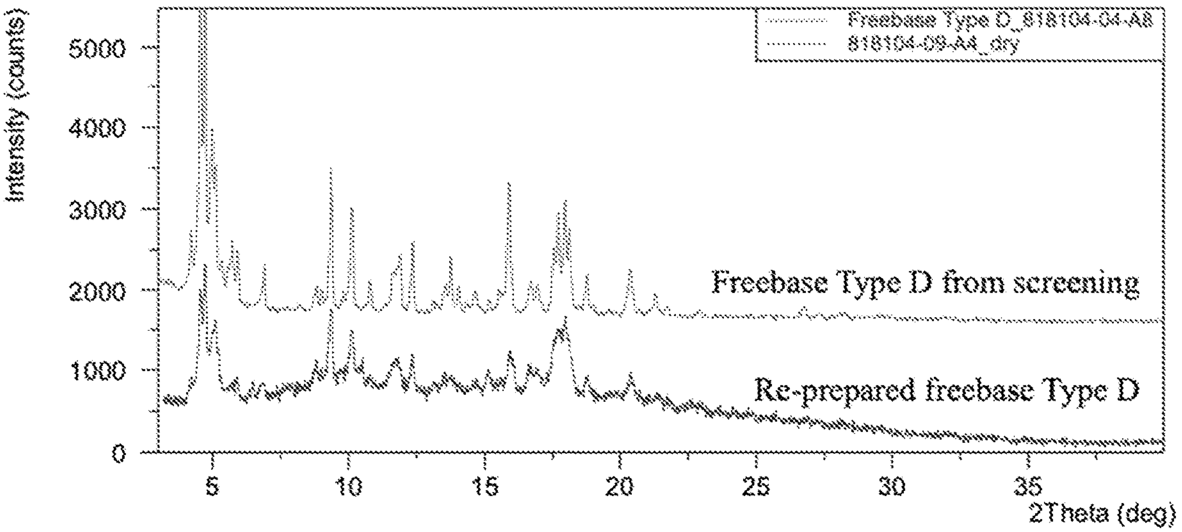
FIG. 29 provides a representative XRPD pattern of freebase Form D of Compound A.

In some embodiments, freebase Form D of Compound A can exhibit an XRPD pattern as shown in FIG. 29. In some embodiments, freebase Form D of Compound A can be characterized by one or more peaks in an XRPD pattern selected from:

| Peak | 2θ | Relative Intensity [%] |
|---|---|---|
| 1 | 4.02 | 24.19 |
| 2 | 4.37 | 80.83 |
| 3 | 4.57 | 100.00 |
| 4 | 4.93 | 64.43 |
| 5 | 5.74 | 23.65 |
| 6 | 6.67 | 20.57 |
| 7 | 8.65 | 33.85 |
| 8 | 9.21 | 73.23 |
| 9 | 9.94 | 56.63 |
| 10 | 10.35 | 34.00 |
| 11 | 11.71 | 33.87 |
| 12 | 12.20 | 35.80 |
| 13 | 13.40 | 24.71 |
| 14 | 14.50 | 21.75 |
| 15 | 14.96 | 27.87 |
| 16 | 15.75 | 40.68 |
| 17 | 16.45 | 30.38 |
| 18 | 17.46 | 53.95 |
| 19 | 17.80 | 64.25 |
| 20 | 18.62 | 24.94 |
| 21 | 20.21 | 26.36 |
| 22 | 21.71 | 8.27 |
| 23 | 22.59 | 5.08 |
| 24 | 27.96 | 1.75 |
| 25 | 33.36 | 1.52 |

Figure 30:
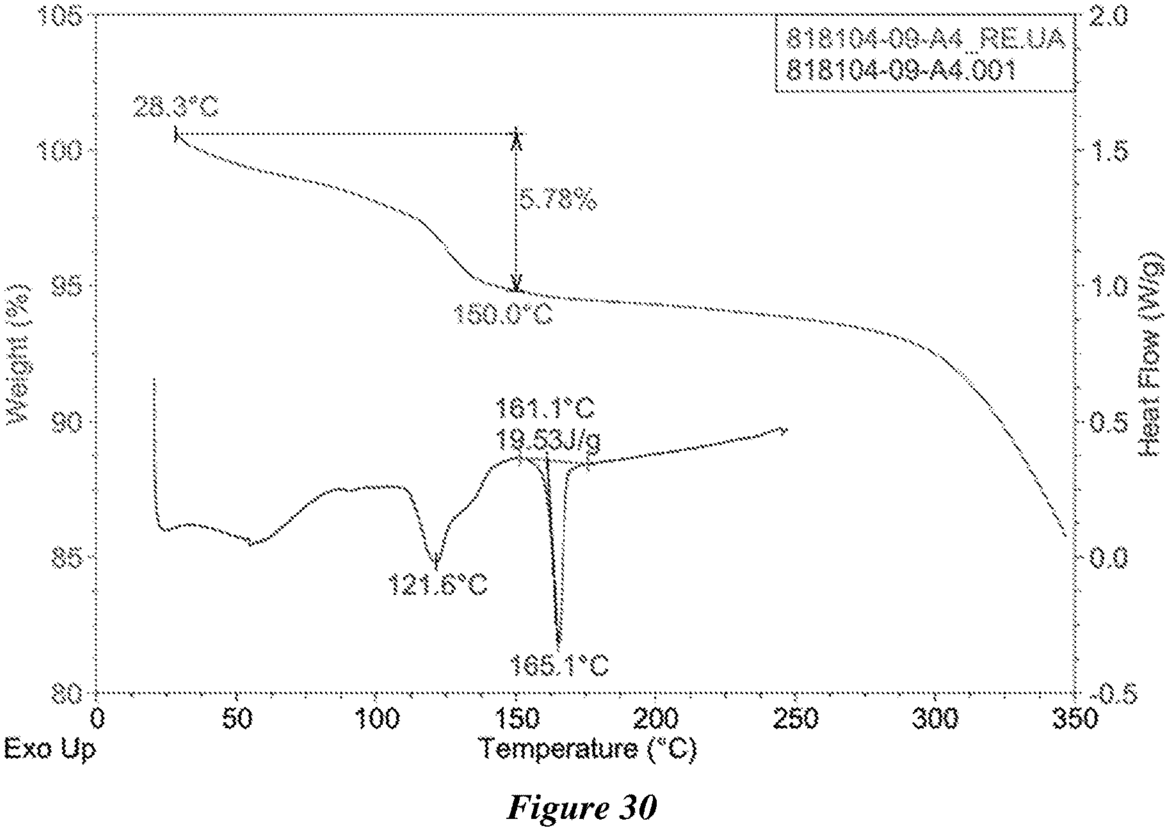
FIG. 30 provides a representative DSC and TGA thermogram of freebase Form D of Compound A.

In some embodiments, freebase Form D of Compound A can be characterized by a DSC and/or TGA thermogram. In some embodiments, freebase Form D of Compound A can be characterized by a weight loss of about 5.8% when heated from about 28° C. to about 150° C. In some embodiments, freebase Form D of Compound A can be characterized by a first endotherm in the range of about 118° C. and about 126° C. and a second endotherm in the range of about 161° C. and about 169° C. In some embodiments, freebase Form D of Compound A can be characterized by a first endotherm in the range of about 120° C. and about 124° C. and a second endotherm in the range of about 163° C. and about 167° C. In some embodiments, freebase Form D of Compound A can be characterized by a first endotherm at about 121.6° C. and a second endotherm at about 165.1° C. In some embodiments, freebase Form D of Compound A can have a DSC and/or TGA thermogram of FIG. 30.

Freebase Form E of Compound A can also be characterized by various methods such as those described herein. In some embodiments, freebase Form E of Compound A can be characterized by one or more peaks in an XRPD pattern, wherein the one or more peaks can be selected from a peak in the range of about 6.0 degrees to about 6.3 degrees, a peak in the range of about 10.5 degrees to about 10.8 degrees, a peak in the range of about 12.0 degrees to about 12.3 degrees, a peak in the range of about 12.2 degrees to about 12.5 degrees, a peak in the range of about 15.1 degrees to about 15.4 degrees, a peak in the range of about 18.8 degrees to about 19.1 degrees, a peak in the range of about 21.5 degrees to about 21.8 degrees, a peak in the range of about 22.5 degrees to about 22.8 degrees and a peak in the range of about 27.3 degrees to about 27.6 degrees. In some embodiments, freebase Form E of Compound A can be characterized by one or more peaks in an XRPD pattern, wherein the one or more peaks can be selected from a peak in the range of about 6.0 degrees to about 6.3 degrees, a peak in the range of about 9.8 degrees to about 10.1 degrees, a peak in the range of about 10.5 degrees to about 10.8 degrees, a peak in the range of about 11.1 degrees to 11.4 degrees, a peak in the range of about 12.0 degrees to about 12.3 degrees, a peak in the range of about 12.2 degrees to about 12.5 degrees, a peak in the range of about 13.8 degrees to 14.1 degrees, a peak in the range of about 15.1 degrees to about 15.4 degrees, a peak in the range of about 16.3 degrees to about 16.6 degrees, a peak in the range of about 17.0 degrees to about 17.3 degrees, a peak in the range of about 18.0 degrees to about 18.3 degrees, a peak in the range of about 18.3 degrees to about 18.6 degrees, a peak in the range of about 18.8 degrees to about 19.1 degrees, a peak in the range of about 19.2 degrees to about 19.5 degrees, a peak in the range of about 19.6 degrees to about 19.9 degrees, a peak in the range of about 20.2 degrees to about 20.5 degrees, a peak in the range of about 21.5 degrees to about 21.8 degrees, 21.9 degrees to about 22.2 degrees, a peak in the range of about 22.5 degrees to about 22.8 degrees, a peak in the range of about 23.6 degrees to about 23.9 degrees, a peak in the range of about 24.5 degrees to about 24.8 degrees, a peak in the range of about 25.1 degrees to about 25.4 degrees, a peak in the range of about 25.5 degrees to about 25.8 degrees, a peak in the range of about 27.3 degrees to about 27.6 degrees, a peak in the range of about 29.1 degrees to about 29.4 degrees, a peak in the range of about 29.7 degrees to about 30.0 degrees, a peak in the range of about 30.0 degrees to about 30.3 degrees, a peak in the range of about 30.5 degrees to about 30.8 degrees and a peak in the range of about 31.4 degrees to about 31.7 degrees.

In some embodiments, freebase Form E of Compound A can be characterized by one or more peaks in an XPRD pattern, wherein the one or more peaks can be selected from about 6.20 degrees, about 10.63 degrees, about 12.17 degrees, about 12.40 degrees, about 15.22 degrees, about 18.96 degrees, about 21.63 degrees, about 22.62 degrees and about 27.43 degrees. In some embodiments, freebase Form E of Compound A can be characterized by one or more peaks in an XPRD pattern, wherein the one or more peaks can be selected from about 6.20 degrees, about 9.94 degrees, about 10.63 degrees, about 11.26 degrees, about 12.17 degrees, about 12.40 degrees, about 13.92 degrees, about 15.22 degrees, about 16.41 degrees, about 17.19 degrees, about 18.19 degrees, about 18.39, about 18.96 degrees, about 19.32 degrees, about 19.76 degrees, about 20.38 degrees, about 21.63 degrees, about 22.09 degrees, about 22.62 degrees, about 23.75 degrees, about 24.66 degrees, about 25.30 degrees, about 25.59 degrees, about 27.43 degrees, about 29.22 degrees, about 29.89 degrees, about 30.17 degrees, about 30.69 degrees and about 31.53 degrees.

Figure 31:
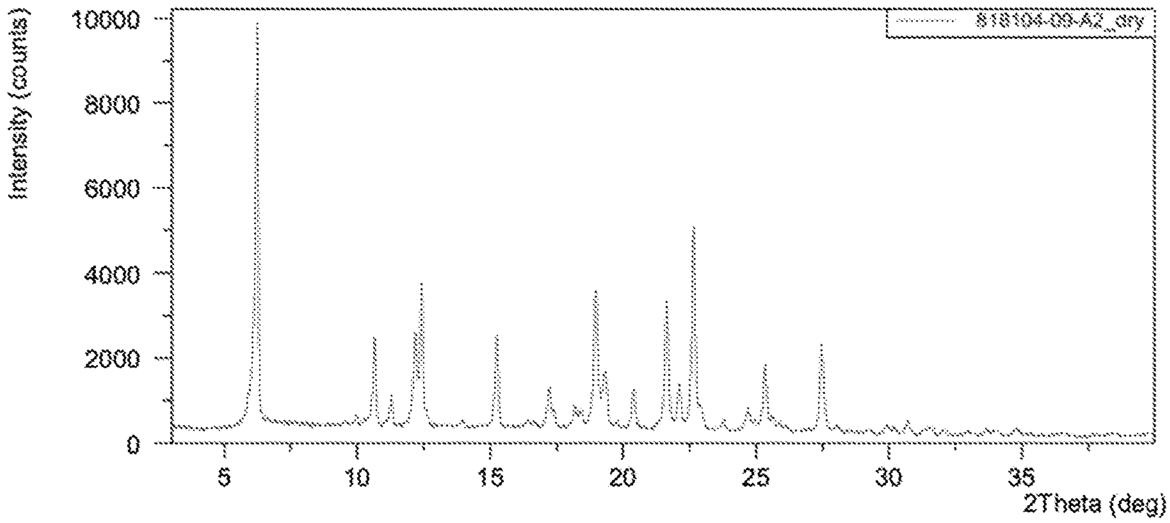
FIG. 31 provides a representative XRPD pattern freebase Form E of Compound A.

In some embodiments, freebase Form E of Compound A can exhibit an XRPD pattern as shown in FIG. 31. In some embodiments, freebase Form E of Compound A can be characterized by one or more peaks in an XRPD pattern selected from:

| Peak | 2θ | Relative Intensity [%] |
|---|---|---|
| 1 | 6.20 | 100.00 |
| 2 | 9.94 | 2.64 |
| 3 | 10.63 | 22.02 |
| 4 | 11.26 | 6.87 |
| 5 | 12.17 | 23.47 |
| 6 | 12.40 | 34.84 |
| 7 | 13.92 | 1.51 |
| 8 | 15.22 | 22.51 |
| 9 | 16.41 | 2.34 |
| 10 | 17.19 | 10.03 |

-continued

| Peak | 2θ | Relative Intensity [%] |
|---|---|---|
| 11 | 18.19 | 5.63 |
| 12 | 18.39 | 4.65 |
| 13 | 18.96 | 34.87 |
| 14 | 19.32 | 14.67 |
| 15 | 19.76 | 2.11 |
| 16 | 20.38 | 10.19 |
| 17 | 21.63 | 32.04 |
| 18 | 22.09 | 11.70 |
| 19 | 22.62 | 50.96 |
| 20 | 23.75 | 2.81 |
| 21 | 24.66 | 5.74 |
| 22 | 25.30 | 16.13 |
| 23 | 25.59 | 3.85 |
| 24 | 27.43 | 21.24 |
| 25 | 29.22 | 0.65 |
| 26 | 29.89 | 2.21 |
| 27 | 30.17 | 1.40 |
| 28 | 30.69 | 2.99 |
| 29 | 31.53 | 1.58 |

Figure 32:
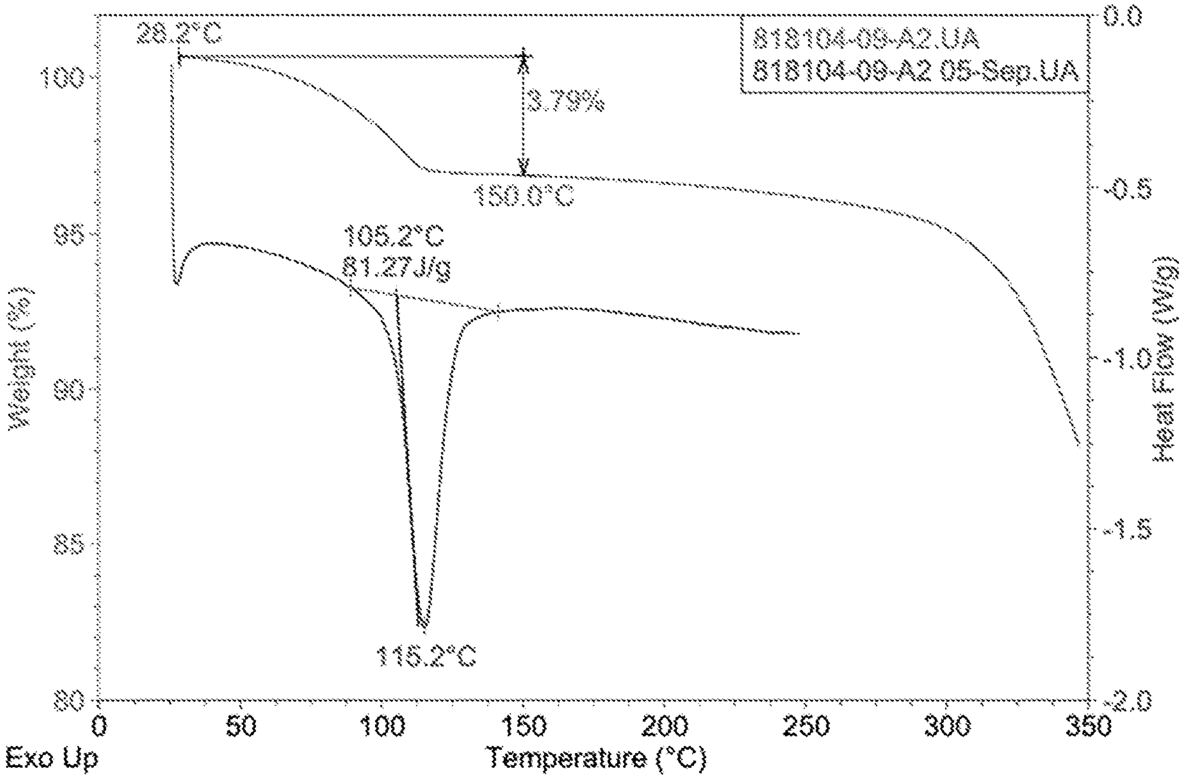
FIG. 32 provides a representative DSC and TGA thermogram of freebase Form E of Compound A.

In some embodiments, freebase Form E of Compound A can be characterized by a DSC and/or TGA thermogram. In some embodiments, freebase Form E of Compound A can be characterized by a weight loss of about 3.8% when heated from about 28 to ° C. about 150 TC. In some embodiments, freebase Form E of Compound A can be characterized by an endotherm in the range of about 105° C. and about 125 TC. In some embodiments, freebase Form E of Compound A can be characterized by an endotherm in the range of about 110° C. and about 118 TC. In some embodiments, a freebase Form E of Compound A can be characterized by an endotherm at about 115.2 TC. In some embodiments, freebase Form E of Compound A can have a DSC and/or TGA thermogram of FIG. 32.

In some embodiments, freebase Form E of Compound A can be obtained by solution crystallization, and can be characterized by an endotherm at about 114.3° C. The purity of such compound is about 99.6%. In some embodiments, Freebase Form E of Compound A can be a hydrate.

Freebase Form F of Compound A can also be characterized by various methods such as those described herein. In some embodiments, freebase Form F of Compound A can be characterized by one or more peaks in an XRPD pattern, wherein the one or more peaks can be selected from a peak in the range of about 4.9 degrees to about 5.3 degrees, a peak in the range of about 6 degrees to about 6.4 degrees, a peak in the range of about 10 degrees to about 10.4 degrees, a peak in the range of about 12.2 degrees to about 12.6 degrees and a peak in the range of about 19 degrees to about 19.4 degrees. In some embodiments, freebase Form F of Compound A can be characterized by one or more peaks in an XRPD pattern, wherein the one or more peaks can be selected from a peak in the range of about 4.9 degrees to about 5.3 degrees, a peak in the range of about 6 degrees to about 6.4 degrees, a peak in the range of about 10 degrees to about 10.4 degrees, a peak in the range of about 12.2 degrees to about 12.6 degrees, a peak in the range of about 12.9 degrees to about 13.3 degrees, a peak in the range of about 16.4 degrees to about 16.8 degrees and a peak in the range of about 19 degrees to about 19.4 degrees.

In some embodiments, freebase Form F of Compound A can be characterized by one or more peaks in an XPRD pattern, wherein the one or more peaks can be selected from about 5.14 degrees, about 6.24 degrees, about 10.19 degrees, about 12.4 degrees and about 19.15 degrees. In some embodiments, freebase Form F of Compound A can be characterized by one or more peaks in an XPRD pattern, wherein the one or more peaks can be selected from about 5.14 degrees, about 6.24 degrees, about 10.19 degrees, about 12.4 degrees, about 13.11 degrees, about 16.58 degrees and about 19.15 degrees.

Figure 33:
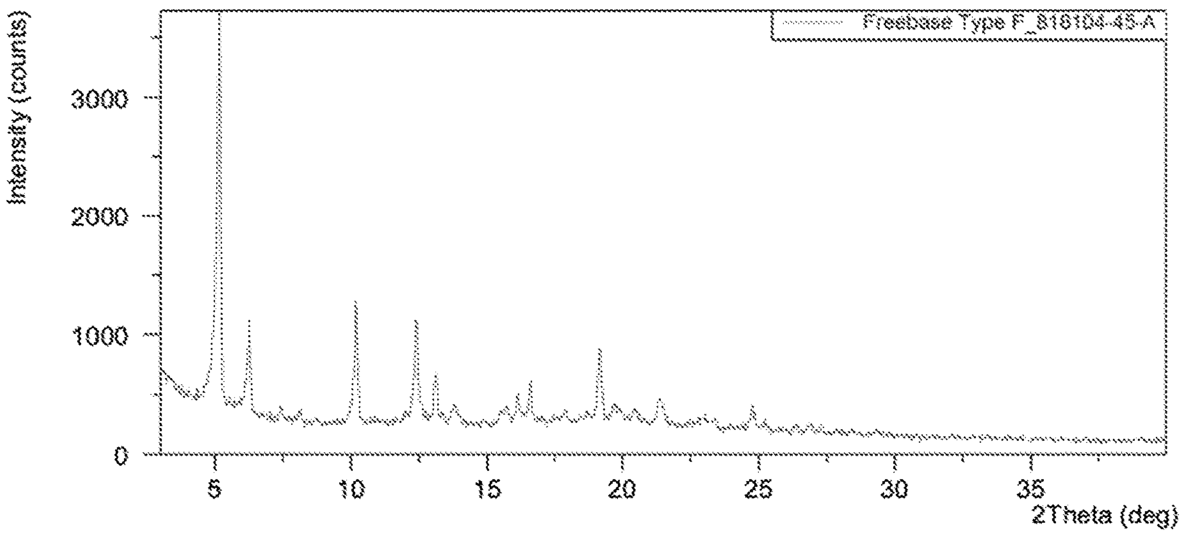
FIG. 33 provides a representative XRPD pattern of freebase Form F of Compound A.

In some embodiments, freebase Form F of Compound A can exhibit an XRPD pattern as shown in FIG. 33. In some embodiments, freebase Form F of Compound A can be characterized by one or more peaks in an XRPD pattern selected from:

| Peak | 2θ | Relative Intensity [%] |
|---|---|---|
| 1 | 5.14 | 100.00 |
| 2 | 6.24 | 20.38 |
| 3 | 7.43 | 2.05 |
| 4 | 8.13 | 1.96 |
| 5 | 10.19 | 28.03 |
| 6 | 12.40 | 24.74 |
| 7 | 13.11 | 11.69 |
| 8 | 13.78 | 4.52 |
| 9 | 15.73 | 4.32 |
| 10 | 16.11 | 7.85 |
| 11 | 16.58 | 10.62 |
| 12 | 17.85 | 4.03 |
| 13 | 19.15 | 18.79 |
| 14 | 19.68 | 5.58 |
| 15 | 20.42 | 4.86 |
| 16 | 21.34 | 7.70 |
| 17 | 23.36 | 3.08 |
| 18 | 24.74 | 6.17 |
| 19 | 26.33 | 1.58 |
| 20 | 26.84 | 2.36 |
| 21 | 29.36 | 1.04 |

Figure 34:
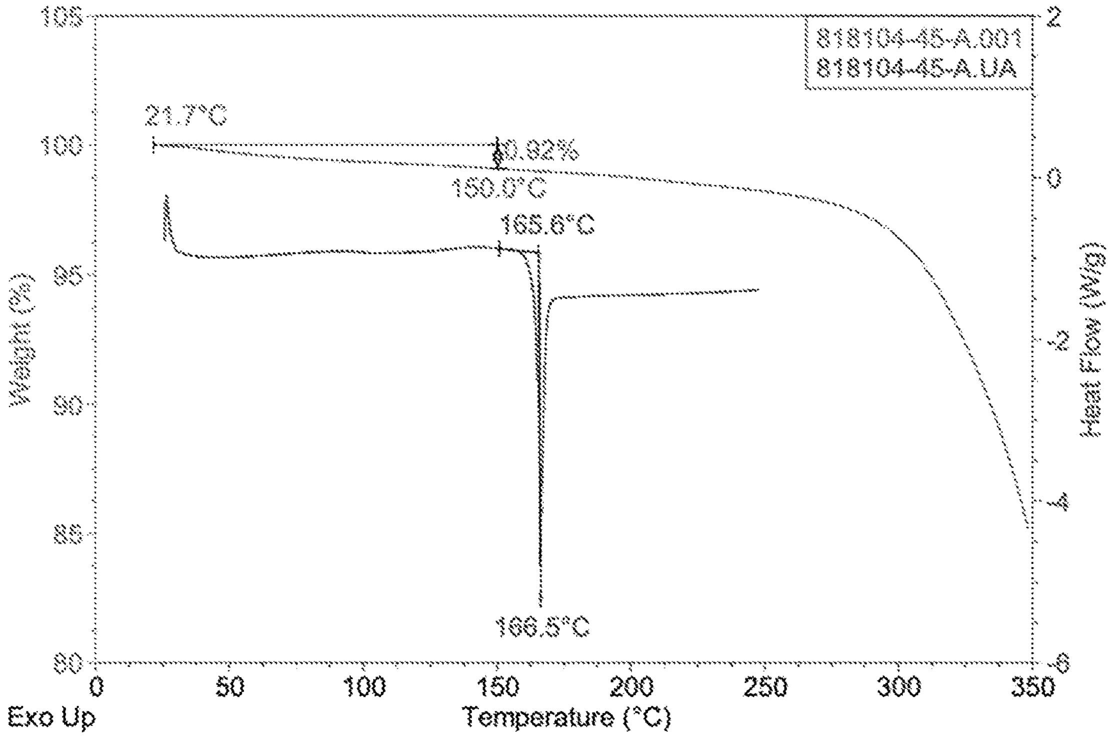
FIG. 34 provides a representative DSC and TGA thermogram of freebase Form F of Compound A.

In some embodiments, freebase Form F of Compound A can be characterized by a DSC and/or TGA thermogram. In some embodiments, freebase Form F of Compound A can be characterized by a weight loss of about 0.9% when heated from about 22° C. to about 150° C. In some embodiments, freebase Form F of Compound A can be characterized by an endotherm in the range of about 163° C. and about 171° C. In some embodiments, freebase Form F of Compound A can be characterized by an endotherm in the range of about 165° C. and about 169° C. In some embodiments, freebase Form F of Compound A can be characterized by an endotherm at about 166.5° C. In some embodiments, freebase Form F of Compound A can have a DSC and/or TGA thermogram of FIG. 34.

Freebase Form G of Compound A can also be characterized by various methods such as those described herein. In some embodiments, freebase Form G of Compound A can be characterized by one or more peaks in an XRPD pattern, wherein the one or more peaks can be selected from a peak in the range of about 3.1 degrees to about 3.5 degrees, a peak in the range of about 5 degrees to about 5.4 degrees, a peak in the range of about 11.2 degrees to about 11.6 degrees and a peak in the range of about 16.3 degrees to about 16.7 degrees. In some embodiments, freebase Form G of Compound A can be characterized by one or more peaks in an XRPD pattern, wherein the one or more peaks can be selected from a peak in the range of about 3.1 degrees to about 3.5 degrees, a peak in the range of about 5 degrees to about 5.4 degrees, a peak in the range of about 9.3 degrees to about 9.7 degrees, a peak in the range of about 11.2 degrees to about 11.6 degrees, a peak in the range of about 12 degrees to about 12.4 degrees, a peak in the range of about 14.6 degrees to about 15 degrees, a peak in the range of about 14.9 degrees to about 15.3 degrees, a peak in the range of about 15.2 degrees to about 15.6 degrees, a peak in the range of about 16.3 degrees to about 16.7 degrees, a peak in the range of about 18.7 degrees to about 19.1 degrees and a peak in the range of about 22.2 degrees to about 22.6 degrees.

In some embodiments, freebase Form G of Compound A can be characterized by one or more peaks in an XPRD pattern, wherein the one or more peaks can be selected from about 3.32 degrees, about 5.17 degrees, about 11.35 degrees and about 16.46 degrees. In some embodiments, freebase Form G of Compound A can be characterized by one or more peaks in an XPRD pattern, wherein the one or more peaks can be selected from about 3.32 degrees, about 5.17 degrees, about 9.46 degrees, about 11.35 degrees, about 12.22 degrees, about 14.83 degrees, about 15.09 degrees, about 15.36 degrees, about 16.46 degrees, about 18.88 degrees and about 22.43 degrees.

Figure 35:
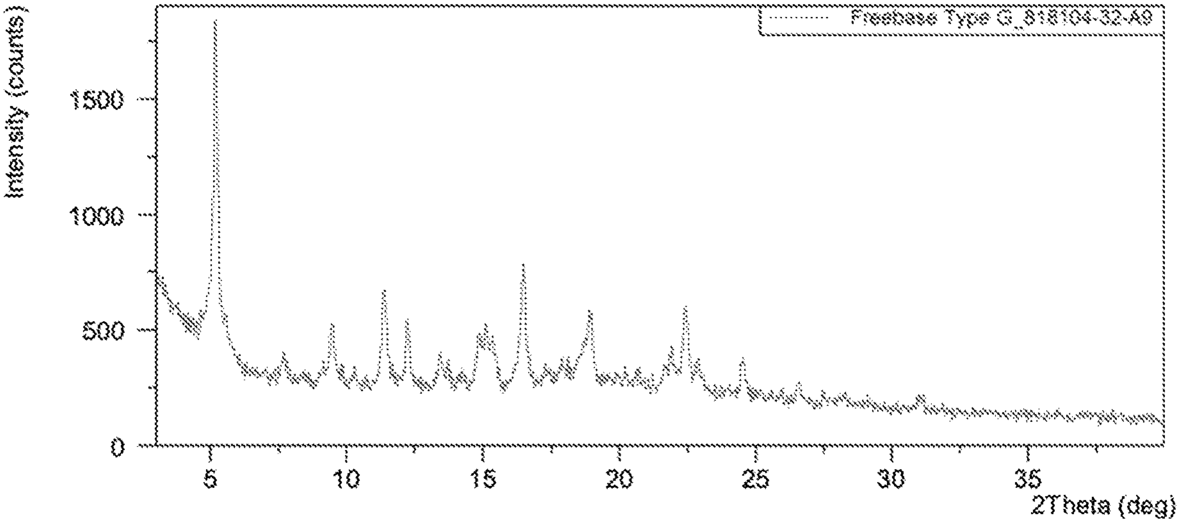
FIG. 35 provides a representative XRPD pattern of freebase Form G of Compound A.

In some embodiments, freebase Form G of Compound A can exhibit an XRPD pattern as shown in FIG. 35. In some embodiments, freebase Form G of Compound A can be characterized by one or more peaks in an XRPD pattern selected from:

| Peak | 2θ | Relative Intensity [%] |
|---|---|---|
| 1 | 3.32 | 26.88 |
| 2 | 5.17 | 100.00 |
| 3 | 7.69 | 8.00 |
| 4 | 9.46 | 17.31 |
| 5 | 10.26 | 3.39 |
| 6 | 11.35 | 26.95 |
| 7 | 12.22 | 17.89 |
| 8 | 13.41 | 9.15 |
| 9 | 14.83 | 14.43 |
| 10 | 15.09 | 15.69 |
| 11 | 15.36 | 10.91 |
| 12 | 16.46 | 32.74 |
| 13 | 18.88 | 18.21 |
| 14 | 21.92 | 9.11 |
| 15 | 22.43 | 22.59 |
| 16 | 24.54 | 9.38 |
| 17 | 26.55 | 5.05 |
| 18 | 31.07 | 3.43 |

Figure 36:
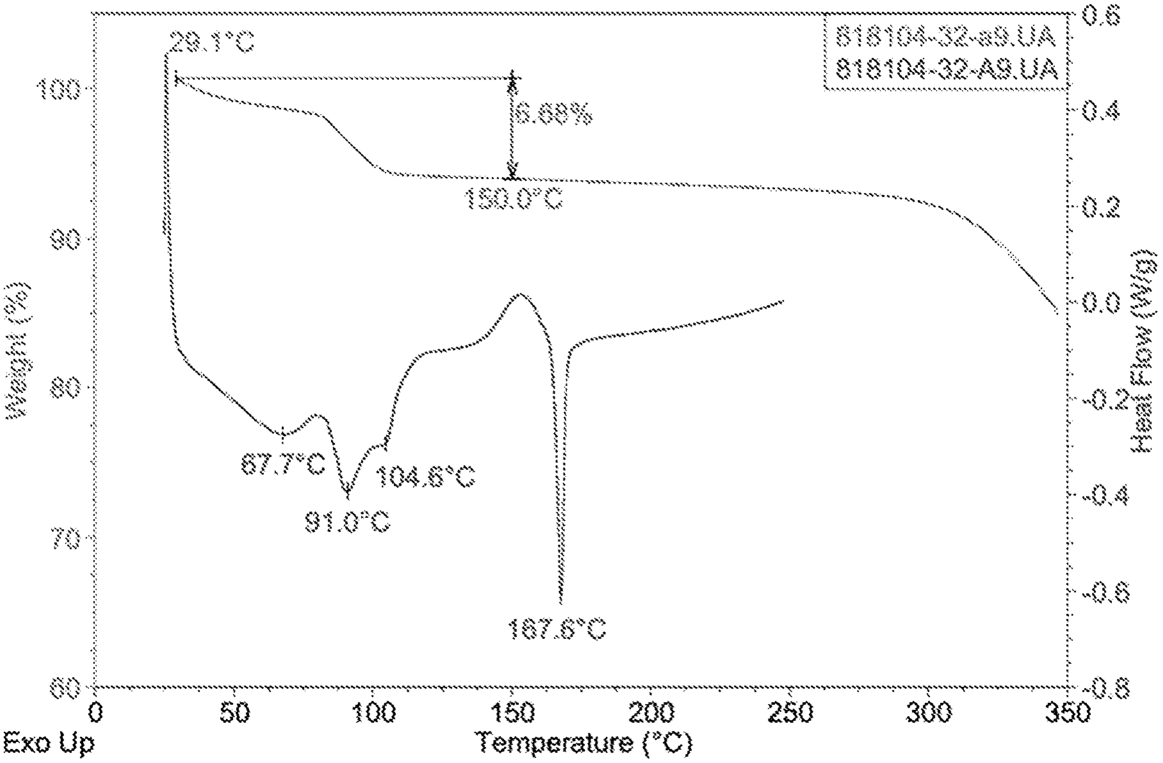
FIG. 36 provides a representative DSC and TGA thermogram freebase Form G of Compound A.

In some embodiments, freebase Form G of Compound A can be characterized by a DSC and/or TGA thermogram. In some embodiments, freebase Form G of Compound A can be characterized by a weight loss of about 6.7% when heated from about 29° C. to about 150° C. In some embodiments, freebase Form G of Compound A can be characterized by a first endotherm in the range of about 64° C. and about 72° C., a second endotherm in the range of about 87° C. and about 95° C., a third endotherm in the range of about 101° C. and about 109° C. and a fourth endotherm in the range of about 164° C. and about 171° C. In some embodiments, freebase Form G of Compound A can be characterized by a first endotherm in the range of about 66° C. and about 70° C., a second endotherm in the range of about 89° C. and about 93° C., a third endotherm in the range of about 103° C. and about 107° C. and a fourth endotherm in the range of about 166° C. and about 169° C. In some embodiments, freebase Form G of Compound A can be characterized by a first endotherm at about 67.7° C., a second endotherm at about 91.0° C., a third endotherm at about 104.6° C. and a fourth endotherm at about 167.6° C. In some embodiments, freebase Form G of Compound A can have a DSC and/or TGA thermogram of FIG. 36.

In other embodiments, freebase Form G of Compound A can be characterized by a first endotherm in the range of about 59° C. and about 67° C., a second endotherm in the range of about 104° C. and about 112° C., a third endotherm in the range of about 117° C. and about 125° C. and a fourth endotherm in the range of about 164° C. and about 171° C. In some embodiments, freebase Form G of Compound A can be characterized by a first endotherm in the range of about 61° C. and about 65° C., a second endotherm in the range of about 106° C. and about 110° C., a third endotherm in the range of about 119° C. and about 123° C. and a fourth endotherm in the range of about 166° C. and about 169° C. In some embodiments, freebase Form G of Compound A can be characterized by a first endotherm at about 63.2° C., a second endotherm at about 108.0° C., a third endotherm at about 120.7° C. and a fourth endotherm at about 167.6° C.

Freebase Form H of Compound A can also be characterized by various methods such as those described herein. In some embodiments, freebase Form H of Compound A can be characterized by one or more peaks in an XRPD pattern, wherein the one or more peaks can be selected from a peak in the range of about 4.6 degrees to about 5 degrees, a peak in the range of about 5 degrees to about 5.4 degrees, a peak in the range of about 10.2 degrees to about 10.6 degrees, a peak in the range of about 10.7 degrees to about 11.1 degrees and a peak in the range of about 17.5 degrees to about 17.9 degrees.

In some embodiments, freebase Form H of Compound A can be characterized by one or more peaks in an XPRD pattern, wherein the one or more peaks can be selected from about 4.84 degrees, about 5.24 degrees, about 10.4 degrees, about 10.87 degrees and about 17.73 degrees.

Figure 37:
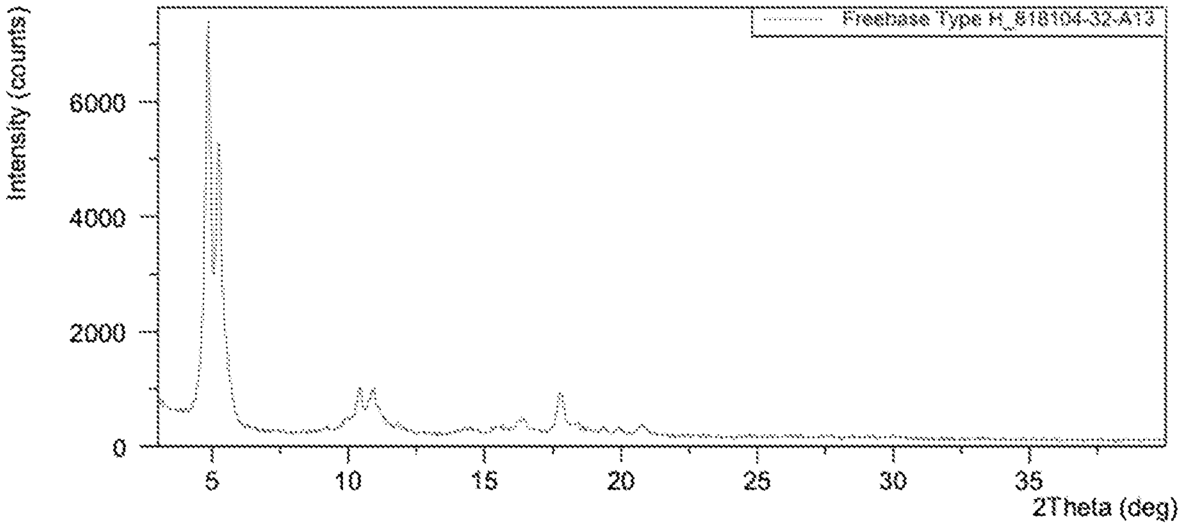
FIG. 37 provides a representative XRPD pattern of freebase Form H of Compound A.

In some embodiments, freebase Form H of Compound A can exhibit an XRPD pattern as shown in FIG. 37. In some embodiments, freebase Form H of Compound A can be characterized by one or more peaks in an XRPD pattern selected from:

| Peak | 2θ | Relative Intensity [%] |
|---|---|---|
| 1 | 4.84 | 100.00 |
| 2 | 5.24 | 67.88 |
| 3 | 9.17 | 1.34 |
| 4 | 9.90 | 3.54 |
| 5 | 10.40 | 10.87 |
| 6 | 10.87 | 10.82 |
| 7 | 14.46 | 1.29 |
| 8 | 15.37 | 1.94 |
| 9 | 16.42 | 3.92 |
| 10 | 17.73 | 10.71 |
| 11 | 19.37 | 1.98 |
| 12 | 19.90 | 1.53 |
| 13 | 20.77 | 2.44 |
| 14 | 27.59 | 0.34 |

Figure 38:
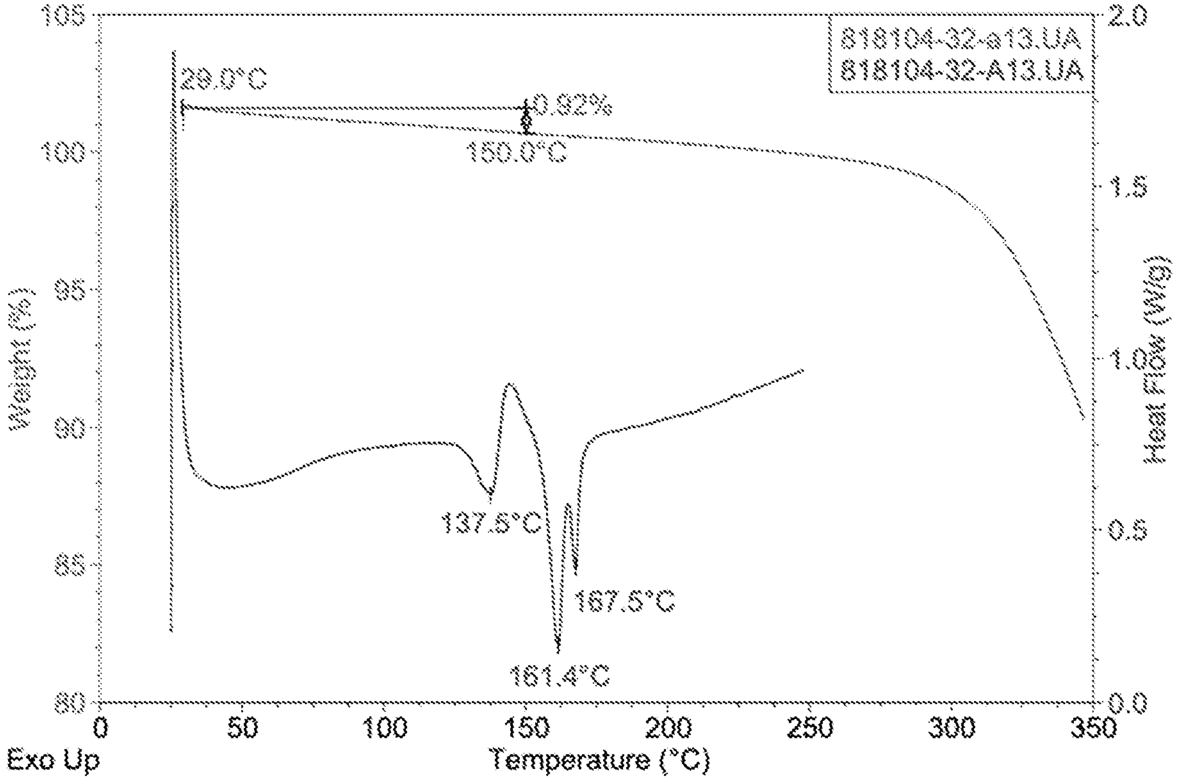
FIG. 38 provides a representative DSC and TGA thermogram of freebase Form H of Compound A.

In some embodiments, freebase Form H of Compound A can be characterized by a DSC and/or TGA thermogram. In some embodiments, freebase Form H of Compound A can be characterized by a weight loss of about 0.9% when heated from about 29° C. to about 150° C. In some embodiments, freebase Form H of Compound A can be characterized by a first endotherm in the range of about 134° C. and about 142° C., a second endotherm in the range of about 157° C. and about 165° C. and a third endotherm in the range of about 164° C. and about 172° C. In some embodiments, freebase Form H of Compound A can be characterized by a first endotherm in the range of about 136° C. and about 140° C., a second endotherm in the range of about 159° C. and about 163° C. and a third endotherm in the range of about 166° C. and about 170° C. In some embodiments, freebase Form H of Compound A can be characterized by a first endotherm at about 137.5° C., a second endotherm at about 161.4° C. and a third endotherm at about 167.5° C. In some embodiments, freebase Form H of Compound A can have a DSC and/or TGA thermogram of FIG. 38.

In other embodiments, freebase Form H of Compound A can be characterized by a first endotherm in the range of about 133° C. and about 141° C., a second endotherm in the range of about 155° C. and about 163° C. and a third endotherm in the range of about 162° C. and about 170° C. In some embodiments, freebase Form H of Compound A can be characterized by a first endotherm in the range of about 135° C. and about 139° C., a second endotherm in the range of about 157° C. and about 161° C. and a third endotherm in the range of about 164° C. and about 168° C. In some embodiments, freebase Form H of Compound A can be characterized by a first endotherm at about 137.2° C., a second endotherm at about 158.9° C. and a third endotherm at about 166.2° C.

Freebase Form I of Compound A can also be characterized by various methods such as those described herein. In some embodiments, freebase Form I of Compound A can be characterized by one or more peaks in an XRPD pattern, wherein the one or more peaks can be selected from a peak in the range of about 6.5 degrees to about 6.9 degrees, a peak in the range of about 10.4 degrees to about 10.8 degrees, a peak in the range of about 10.7 degrees to about 11.1 degrees, a peak in the range of about 13.3 degrees to about 13.7 degrees, a peak in the range of about 13.8 degrees to about 14.2 degrees, a peak in the range of about 14.6 degrees to about 15 degrees, a peak in the range of about 15.2 degrees to about 15.6 degrees, a peak in the range of about 15.4 degrees to about 15.8 degrees, a peak in the range of about 16.8 degrees to about 17.2 degrees, a peak in the range of about 19.1 degrees to about 19.5 degrees, a peak in the range of about 20 degrees to about 20.4 degrees, a peak in the range of about 21.3 degrees to about 21.7 degrees, a peak in the range of about 21.6 degrees to about 22 degrees, a peak in the range of about 24.9 degrees to about 25.3 degrees and a peak in the range of about 28 degrees to about 28.4 degrees. In some embodiments, freebase Form I of Compound A can be characterized by one or more peaks in an XRPD pattern, wherein the one or more peaks can be selected from a peak in the range of about 4.8 degrees to about 5.2 degrees, a peak in the range of about 6.5 degrees to about 6.9 degrees, a peak in the range of about 9.6 degrees to about 10 degrees, a peak in the range of about 10.4 degrees to about 10.8 degrees, a peak in the range of about 10.7 degrees to about 11.1 degrees, a peak in the range of about 13.3 degrees to about 13.7 degrees, a peak in the range of about 13.8 degrees to about 14.2 degrees, a peak in the range of about 14.6 degrees to about 15 degrees, a peak in the range of about 15.2 degrees to about 15.6 degrees, a peak in the range of about 15.4 degrees to about 15.8 degrees, a peak in the range of about 16.8 degrees to about 17.2 degrees, a peak in the range of about 19.1 degrees to about 19.5 degrees, a peak in the range of about 19.6 degrees to about 20 degrees, a peak in the range of about 20 degrees to about 20.4 degrees, a peak in the range of about 20.7 degrees to about 21.1 degrees, a peak in the range of about 21.3 degrees to about 21.7 degrees, a peak in the range of about 21.6 degrees to about 22 degrees, a peak in the range of about 23.5 degrees to about 23.9 degrees, a peak in the range of about 24.5 degrees to about 24.9 degrees, a peak in the range of about 24.9 degrees to about 25.3 degrees, a peak in the range of about 25.4 degrees to about 25.8 degrees, a peak in the range of about 25.8 degrees to about 26.2 degrees, a peak in the range of about 27.4 degrees to about 27.8 degrees, a peak in the range of about 28 degrees to about 28.4 degrees, a peak in the range of about 28.5 degrees to about 28.9 degrees, a peak in the range of about 29.6 degrees to about 30 degrees, a peak in the range of about 30.8 degrees to about 31.2 degrees and a peak in the range of about 33.2 degrees to about 33.6 degrees.

In some embodiments, freebase Form I of Compound A can be characterized by one or more peaks in an XPRD pattern, wherein the one or more peaks can be selected from about 6.73 degrees, about 10.59 degrees, about 10.85 degrees, about 13.46 degrees, about 13.98 degrees, about 14.77 degrees, about 15.44 degrees, about 15.56 degrees, about 17.01 degrees, about 19.26 degrees, about 20.22 degrees, about 21.47 degrees, about 21.76 degrees, about 25.11 degrees and about 28.16 degrees. In some embodiments, freebase Form I of Compound A can be characterized by one or more peaks in an XPRD pattern, wherein the one or more peaks can be selected from about 4.95 degrees, about 6.73 degrees, about 9.84 degrees, about 10.59 degrees, about 10.85 degrees, about 13.46 degrees, about 13.98 degrees, about 14.77 degrees, about 15.44 degrees, about 15.56 degrees, about 17.01 degrees, about 19.26 degrees, about 19.8 degrees, about 20.22 degrees, about 20.92 degrees, about 21.47 degrees, about 21.76 degrees, about 23.7 degrees, about 24.73 degrees, about 25.11 degrees, about 25.62 degrees, about 25.95 degrees, about 27.6 degrees, about 28.16 degrees, about 28.71 degrees, about 29.77 degrees, about 30.99 degrees and about 33.37 degrees.

Figure 39:
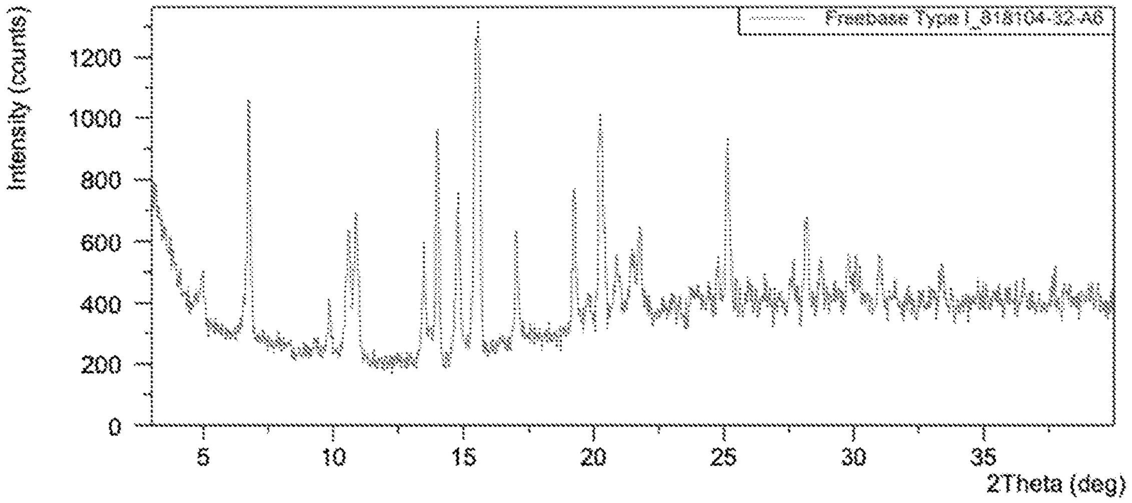
FIG. 39 provides a representative XRPD pattern of freebase Form I of Compound A.

In some embodiments, freebase Form I of Compound A can exhibit an XRPD pattern as shown in FIG. 39. In some embodiments, freebase Form I of Compound A can be characterized by one or more peaks in an XRPD pattern selected from:

| Peak | 2θ | Relative Intensity [%] |
|---|---|---|
| 1 | 4.95 | 12.35 |
| 2 | 6.73 | 71.23 |
| 3 | 9.84 | 17.04 |
| 4 | 10.59 | 40.22 |
| 5 | 10.85 | 45.23 |
| 6 | 13.46 | 37.46 |
| 7 | 13.98 | 70.71 |
| 8 | 14.77 | 52.28 |
| 9 | 15.44 | 95.56 |
| 10 | 15.56 | 100.00 |
| 11 | 17.01 | 37.33 |
| 12 | 19.26 | 47.96 |
| 13 | 19.80 | 14.19 |
| 14 | 20.22 | 67.14 |
| 15 | 20.92 | 24.19 |
| 16 | 21.47 | 26.38 |
| 17 | 21.76 | 35.11 |
| 18 | 23.70 | 13.70 |
| 19 | 24.73 | 18.50 |
| 20 | 25.11 | 58.91 |
| 21 | 25.62 | 12.26 |
| 22 | 25.95 | 13.98 |
| 23 | 27.60 | 12.97 |
| 24 | 28.16 | 30.94 |
| 25 | 28.71 | 18.96 |
| 26 | 29.77 | 19.85 |
| 27 | 30.39 | 6.50 |
| 28 | 30.99 | 18.22 |
| 29 | 31.58 | 7.48 |
| 30 | 33.37 | 11.98 |
| 31 | 37.65 | 5.62 |

Freebase Form J of Compound A can also be characterized by various methods such as those described herein. In some embodiments, freebase Form J of Compound A can be characterized by one or more peaks in an XRPD pattern, wherein the one or more peaks can be selected from a peak in the range of about 5.9 degrees to about 6.2 degrees, a peak in the range of about 10.4 degrees to about 10.7 degrees, a peak in the range of about 11.5 degrees to about 11.8 degrees, a peak in the range of about 15.1 degrees to about 15.4 degrees, a peak in the range of about 19.3 degrees to about 19.6 degrees, a peak in the range of about 21.8 degrees to about 22.1 degrees, a peak in the range of about 23.1 degrees to about 23.4 degrees and a peak in the range of about 25.3 degrees to about 25.6 degrees. In some embodiments, freebase Form J of Compound A can be characterized by one or more peaks in an XRPD pattern, wherein the one or more peaks can be selected from a peak in the range of about 5.9 degrees to about 6.2 degrees, a peak in the range of about 9.5 degrees to about 9.8 degrees, a peak in the range of about 10.4 degrees to about 10.7 degrees, a peak in the range of about 11.0 degrees to about 11.3 degrees, a peak in the range of about 11.5 degrees to about 11.8 degrees, a peak in the range of about 12.1 degrees to about 12.4 degrees, a peak in the range of about 12.5 degrees to about 12.8 degrees, a peak in the range of about 15.1 degrees to about 15.4 degrees, a peak in the range of about 17.0 degrees to about 17.3 degrees, a peak in the range of about 17.8 degrees to about 18.1 degrees, a peak in the range of about 18.1 degrees to about 18.4 degrees, a peak in the range of about 18.7 degrees to about 19.0 degrees, a peak in the range of about 19.3 degrees to about 19.6 degrees, a peak in the range of about 20.3 degrees to about 20.6 degrees, a peak in the range of about 21.8 degrees to about 22.1 degrees, a peak in the range of about 22.2 degrees to about 22.5 degrees, a peak in the range of about 23.1 degrees to about 23.4 degrees, a peak in the range of about 24.5 degrees to about 24.8 degrees, a peak in the range of about 25.3 degrees to about 25.6 degrees, a peak in the range of about 25.9 degrees to about 26.2 degrees, a peak in the range of about 27.8 degrees to about 28.1 degrees, a peak in the range of about 29.8 degrees to about 30.1 degrees and a peak in the range of about 30.8 degrees to about 31.1 degrees.

In some embodiments, freebase Form J of Compound A can be characterized by one or more peaks in an XPRD pattern, wherein the one or more peaks can be selected from about 6.08 degrees, about 10.58 degrees, about 11.64 degrees, about 15.27 degrees, about 19.42 degrees, about 21.93 degrees, about 23.23 degrees and about 25.49 degrees. In some embodiments, freebase Form J of Compound A can be characterized by one or more peaks in an XPRD pattern, wherein the one or more peaks can be selected from about 6.08 degrees, about 9.63 degrees, about 10.58 degrees, about 11.19 degrees, about 11.64 degrees, about 12.23 degrees, about 12.62 degrees, about 15.27 degrees, about 17.13 degrees, about 17.96 degrees, about 18.28 degrees, about 18.82 degrees, about 19.42 degrees, about 20.48 degrees, about 21.93 degrees, about 22.33 degrees, about 23.23 degrees, about 24.63 degrees, about 25.49 degrees, about 26.08 degrees, about 27.95 degrees, about 29.97 degrees and about 30.98 degrees.

Figure 40:
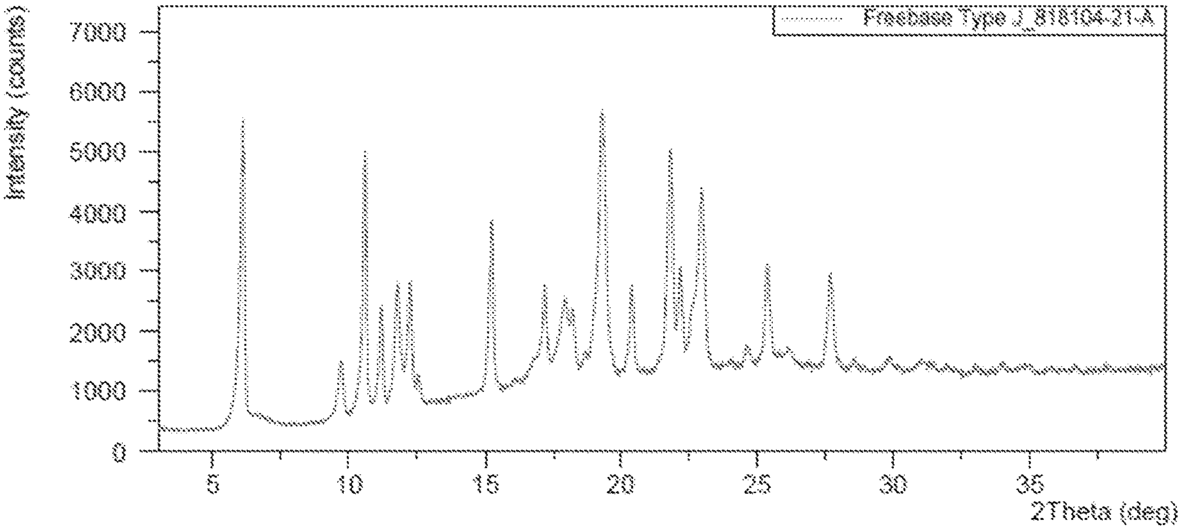
FIG. 40 provides a representative XRPD pattern of freebase Form J of Compound A.

In some embodiments, freebase Form J of Compound A can exhibit an XRPD pattern as shown in FIG. 40. In some embodiments, freebase Form J of Compound A can be characterized by one or more peaks in an XRPD pattern selected from:

| Peak | 2θ | Relative Intensity [%] |
|---|---|---|
| 1 | 6.08 | 91.78 |
| 2 | 9.63 | 17.05 |
| 3 | 10.58 | 85.78 |
| 4 | 11.19 | 36.67 |
| 5 | 11.64 | 40.23 |
| 6 | 12.23 | 37.60 |
| 7 | 12.62 | 12.96 |
| 8 | 15.27 | 51.96 |
| 9 | 17.13 | 34.80 |
| 10 | 17.96 | 33.75 |
| 11 | 18.28 | 28.12 |
| 12 | 18.82 | 22.08 |
| 13 | 19.42 | 100.00 |
| 14 | 20.48 | 30.36 |
| 15 | 21.93 | 75.65 |
| 16 | 22.33 | 28.59 |
| 17 | 23.23 | 69.28 |
| 18 | 24.63 | 14.37 |
| 19 | 25.49 | 39.34 |
| 20 | 26.08 | 12.21 |
| 21 | 27.95 | 23.04 |
| 22 | 29.97 | 5.64 |
| 23 | 30.98 | 4.82 |

Pharmaceutical Compositions

Some embodiments described herein relate to a pharmaceutical composition, that can include an effective amount of a salt of Compound A and/or a salt form described herein (e.g., adipate salt Form A of Compound A,) and a pharmaceutically acceptable carrier, diluent, excipient or combination thereof.

Some embodiments described herein relate to a pharmaceutical composition, that can include an effective amount of a freebase form of Compound A (e.g., freebase Form E or freebase Form J) and a pharmaceutically acceptable carrier, diluent, excipient or combination thereof.

The term "pharmaceutical composition" refers to a mixture of one or more compounds, such as compounds, salts and/or salt forms described herein, disclosed herein with other chemical components, such as diluents or carriers. The pharmaceutical composition facilitates administration of the compound, such as a compound, a salt and/or a salt form described herein, to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound, such as a compound, a salt and/or a salt form described herein, nor cause appreciable damage or injury to an animal to which delivery of the composition is intended.

As used herein, a "carrier" refers to a compound that facilitates the incorporation of a compound, such as a compound, a salt and/or a salt form described herein, into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as anti-oxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds, salts, salt forms and/or compositions described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose.

Multiple techniques of administering a compound (including a freebase form), a salt, a salt form and/or a composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer a compound, a salt, a salt form and/or a composition in a local rather than systemic manner, for example, via injection or implantation of a compound, a salt, a salt form and/or a composition directly into the affected area, often in a depot or sustained release formulation. Furthermore, one may administer a compound, a salt, a salt form and/or a composition in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound, salt and/or salt form described herein formulated in a compatible pharmaceutical carrier may also be prepared, placed in an appropriate container, and labeled for treatment of an indicated condition.

Uses and Methods of Treatment

Some embodiments described herein relate to a method for ameliorating and/or treating a cancer described herein that can include administering an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) to a subject having a cancer described herein. Other embodiments described herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for ameliorating and/or treating a cancer described herein. Still other embodiments described herein relate to an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof), wherein the malignant growth or tumor is due to a cancer described herein. Other embodiments described herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) to a subject having a cancer described herein. Other embodiments described herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for ameliorating or treating a cancer that can include contacting a malignant growth or a tumor, wherein the malignant growth or tumor is due to a cancer described herein. Still other embodiments described herein relate to an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for ameliorating or treating a cancer that can include contacting a malignant growth or a tumor, wherein the malignant growth or tumor is due to a cancer described herein.

Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) to a cancer cell from a cancer described herein. Other embodiments described herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) to a cancer cell from a cancer described herein. Other embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include contacting a cancer cell from a cancer described herein with an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof), and thereby inhibiting the activity of WEE1.

Some embodiments described herein relate to a method for ameliorating or treating a cancer described herein that can include inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) using an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof). Other embodiments described herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for ameliorating or treating a cancer described herein that can include contacting a cancer cell with an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof), wherein the compound inhibits the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

Some embodiments disclosed herein relate to a method for inhibiting the activity of WEE1 that can include providing an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) to a subject having a cancer described herein or a cancer cell from a cancer described herein. Other embodiments disclosed herein relate to the use of an effective amount of a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) in the manufacture of a medicament for inhibiting the activity of WEE1. Still other embodiments disclosed herein relate to a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) for inhibiting the activity of WEE1.

Examples of suitable cancers include, but are not limited to: brain cancers, cervicocerebral cancers, esophageal cancers, thyroid cancers, small cell cancers, non-small cell cancers, breast cancers, lung cancers (for example non-small cell lung cancer and small cell lung cancer), stomach cancers, gallbladder/bile duct cancers, liver cancers, pancreatic cancers, colon cancers, rectal cancers, ovarian cancers, choriocarcinomas, uterus body cancers, uterocervical cancers, renal pelvis/ureter cancers, bladder cancers, prostate cancers, penis cancers, testicular cancers, fetal cancers, Wilms' cancer, skin cancers, malignant melanoma, neuroblastomas, osteosarcomas, Ewing's tumors, soft part sarcomas, acute leukemia, chronic lymphatic leukemias, chronic myelocytic leukemias, polycythemia vera, malignant lymphomas, multiple myeloma, Hodgkin's lymphomas, and non-Hodgkin's lymphomas.

As described herein, a cancer can become resistant to one or more anti-cancer agents. In some embodiments, a compound described herein (for example, a freebase form or a salt form of Compound A, or a pharmaceutically acceptable salt thereof) or a pharmaceutical composition that includes an effective amount of a compound described herein (for example, a freebase form or a salt form of Compound A, or a pharmaceutically acceptable salt thereof) can be used to treat and/or ameliorate a cancer that has become resistant to one or more anti-cancer agents (such as one or more WEE1 inhibitors). Examples of anti-cancer agents that a subject may have developed resistance to include, but are not limited to, WEE1 inhibitors (such as AZD1775 or adavosertib). In some embodiments, the cancer that has become resistant to one or more anti-cancer agents can be a cancer described herein.

Several known WEE1 inhibitors can cause one or more undesirable side effects in the subject being treated. Examples of undesirable side effects include, but are not limited to, thrombocytopenia, neutropenia, anemia, diarrhea, vomiting, nausea, abdominal pain, and constipation. In some embodiments, a compound described herein (for example, a freebase form or a salt form of Compound A, or a pharmaceutically acceptable salt thereof) can decrease the number and/or severity of one or more side effects associated with a known WEE1 inhibitor. In some embodiments, a freebase form or a salt form of Compound A, or a pharmaceutically acceptable salt thereof, can result in a severity of a side effect (such as one of those described herein) that is 25% less than compared to the severity of the same side effect experienced by a subject receiving a known WEE1 inhibitor (such as AZD1775, formally known as MK1775 (CAS No.: 955365-80-7, 2-allyl-1-(6-(2-hydroxypropan-2-yl)pyridin-2-yl)-6-(4-(4-methylpiperazin-1-yl)phenylamino)-1,2-dihydropyrazolo[3,4-d]pyrimidin-3-one)). In some embodiments, a freebase form or a salt form of Compound A, or a pharmaceutically acceptable salt thereof, results in a number of side effects that is 25% less than compared to the number of side effects experienced by a subject receiving a known WEE1 inhibitor (for example, AZD1775). In some embodiments, a freebase form or a salt form of Compound A, or a pharmaceutically acceptable salt thereof, results in a severity of a side effect (such as one of those described herein) that is less in the range of about 10% to about 30% compared to the severity of the same side effect experienced by a subject receiving a known WEE1 inhibitor (such as AZD1775) In some embodiments, a freebase form or a salt form of Compound A, or a pharmaceutically acceptable salt thereof, results in a number of side effects that is in the range of about 10% to about 30% less than compared to the number of side effects experienced by a subject receiving a known WEE1 inhibitor (for example, AZD1775).

The one or more forms of freebase or one or more salt forms of Compound A, or a pharmaceutically acceptable salt thereof, that can be used to treat, ameliorate and/or inhibit the growth of a cancer wherein inhibiting the activity of WEE1 is beneficial is provided in any of the embodiments described in the paragraph starting with "As used herein, (R)-2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo[3,4-d]pyrimidin-3-one is Compound A, which has the structure:" to, and including, the paragraph starting with "In a salt form of Compound A, various amounts of the adipate salt form of Compound A can be present", under the heading titled "Compounds."

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an WEE1 inhibitor is the amount which results in the reduction in WEE1 activity and/or phosphorylation (such as phosphorylation of CDC2). The reduction in WEE1 activity is known to those skilled in the art and can be determined by the analysis of WEE1 intrinsic kinase activity and downstream substrate phosphorylation.

The amount of the freebase form or the salt form of Compound A, or a pharmaceutically acceptable salt thereof, required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day, or any amount in between. The compound may be administered in unit dosage form; for example, containing 1 to 500 mg, 10 to 100 mg, 5 to 50 mg or any amount in between, of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a freebase form or a salt form of Compound A, or pharmaceutically acceptable salts thereof, can be determined by comparing their in vitro activity, and in vivo activity in animal models. Such comparison can be done by comparison against an established drug, such as cisplatin and/or gemcitabine)

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

The freebase of Compound A can be prepared as described in WO 2019/173082, which is hereby incorporated by reference in its entirety. As described in WO 2019/173082, the freebase of Compound A is WEE1 inhibitor.

Preparation of Adipate Salt Form A

Adipate salt Form A was obtained via slurrying equimolar amounts of freebase Form A and adipic acid in methyl tert-butyl ether (MTBE) at 1000 rpm in room temperature (rt) for 4 days. The resulting suspension was centrifuged at 10,000 rpm for 2 minutes to retrieve the solid.

Solution crystallization: Into a 20-mL via was added freebase of Compound A (~1 g) followed by the addition of ethyl acetate (EtOAc, 10 mL) to dissolve the solid. Into a 100-mL reactor was added 1.05 equimolar of adipic acid (~291 mg) followed by the addition of EtOAc (40 mL) to dissolve the solid. Adipate Form A seed (~20 mg) was added to the acid solution (the seed was not dissolved). The freebase solution was added into the acid solution over 4 hrs with stirring at 300 rpm at 25° C. followed by stirring at 300 rpm at 25° C. for 16 hrs. The solution was vacuum filtered, and the solid was washed with EtOAc (2×10 mL) and vacuum dried at rt for 17 hrs.

Preparation of HCl Salt Form A

HCl salt Form A was obtained via slurrying equimolar amounts of freebase Form A and HCl acid in EtOAc:n-heptane (1:1, v:v) at 1000 rpm at rt for 4 days. The resulting suspension was centrifuged at 10,000 rpm for 2 minutes to retrieve the solid.

Preparation of HCl Salt Form B

HCl salt Form B was obtained via slurrying one equivalent of freebase Form B with two equivalents of HCl acid in EtOAc:n-heptane (1:1, v:v) at 1000 rpm at rt for 4 days. The resulting suspension was centrifuged at 10,000 rpm for 2 minutes to retrieve the solid.

Preparation of Sulfate Salt Form A

Sulfate salt Form A was obtained via slurrying equimolar amounts of freebase Form A and sulfuric acid in acetone:$H_2O$ (1:3, v:v) at 1000 rpm at rt for 4 days. The resulting suspension was centrifuged at 10,000 rpm for 2 minutes to retrieve the solid.

Preparation of Mesylate Salt Form A

Mesylate salt Form A was obtained via slurrying equimolar amounts of freebase Form A and methanesulfonic acid in EtOAc:n-heptane (1:1, v:v) at 1000 rpm at rt for 4 days. The resulting suspension was centrifuged at 10,000 rpm for 2 minutes to retrieve the solid.

Preparation of Maleate Salt Form A

Maleate salt Form A was obtained via slurrying equimolar amounts of freebase Form A and maleic acid in EtOAc:n-heptane (1:1, v:v) at 1000 rpm at rt for 4 days. The resulting suspension was centrifuged at 10,000 rpm for 2 minutes to retrieve the solid.

Preparation of Phosphate Salt Form A

Phosphate salt Form A was obtained via slurrying equimolar amounts of freebase Form A and phosphoric acid in acetone:$H_2O$ (1:3, v:v) at 1000 rpm at rt for 4 days. The resulting suspension was centrifuged at 10,000 rpm for 2 minutes to retrieve the solid.

Preparation of Tartrate Salt Form A

Tartrate salt Form A was obtained via slurrying equimolar amounts of freebase Form A and L-tartaric acid in acetone:$H_2O$ (1:3, v:v) at 1000 rpm at rt for 4 days. The resulting suspension was centrifuged at 10,000 rpm for 2 minutes to retrieve the solid.

Preparation of Tosylate Salt Form A.

The tosylate salt Form A. was obtained via slurrying equimolar amounts of freebase Form A and p-toluenesulfonic acid in EtOAc:n-heptane (1:1, v:v) at 1000 rpm at rt for 4 days. The resulting suspension was centrifuged at 10,000 rpm for 2 minutes to retrieve the solid.

Preparation of Mucate Salt Form A

Mucate salt Form A was obtained via slurrying equimolar amounts of freebase Form A and mucic acid in acetone:$H_2O$ (1:3, v:v) at 1000 rpm at rt for 4 days. The resulting suspension was centrifuged at 10,000 rpm for 2 minutes to retrieve the solid.

Preparation of Hippurate Salt Form A

Hippurate salt Form A was obtained via slurrying equimolar amounts of freebase Form A and hippuric acid in acetone:$H_2O$ (1:3, v:v) at 1000 rpm at rt for 4 days. The resulting suspension was centrifuged at 10,000 rpm for 2 minutes to retrieve the solid.

Preparation of Freebase Form A of Compound A

Freebase Form A of Compound A was obtained via slurrying amorphous freebase of Compound A in MTBE at rt for 4 days.

Preparation of Freebase Form B of Compound A

Freebase Form B of Compound A was obtained via slurrying amorphous freebase of Compound A in acetone:$H_2O$ (1:3, v:v) at rt for 4 days.

Preparation of Freebase Form C of Compound A

Freebase Form C of Compound A was obtained via slurrying amorphous freebase of Compound A in EtOAc:n-heptane (1:1, v:v) at rt for 4 days.

Preparation of Freebase Form D of Compound A

Freebase Form D of Compound A was obtained via slurrying amorphous freebase of Compound A in IPAc at rt for 4 days.

Preparation of Freebase Form E of Compound A

Freebase Form E of Compound A was obtained via slurrying amorphous freebase of Compound A in acetone:$H_2O$ (1:3, v:v) at 50 mg scale at rt for 4 days.

Solution crystallization: Into a 20-mL via was added freebase of Compound A (~1 g) followed by the addition of acetone (5 mL) to dissolve the solid. Anti-solvent $H_2O$ (5 mL) was added into the solution with stirring at 1000 rpm at rt (no precipitation was observed). Freebase Form E seed (~20 mg) was added to the solution (the seed was not dissolved). $H_2O$ (10 mL) was added into the sample (gel was observed after addition of 5 mL $H_2$), which converted to a suspension after slurry for 15 min) and stirred at 1000 rpm at rt for 22.5 hrs. The solution was vacuum filtered, and the solid was washed with $H_2O$ (2×10 mL) and vacuum dried at rt for 17 hrs.

Preparation of Freebase Form F of Compound A

Freebase Form F of Compound A was obtained via heating either of freebase Form A, C, D or G of Compound A. Freebase Form F of Compound A was also obtained via heating freebase Form H of Compound A to 160° C. followed by cooling to rt.

Preparation of Freebase Form G of Compound A

Freebase Form G of Compound A was obtained via anti-solvent addition, wherein 15 mg of the amorphous freebase of Compound A was dissolved in about 0.4-1.0 mL of IPA, followed by the addition of n-heptane until precipitant appeared or the total amount of anti-solvent reached 15.0 mL.

Preparation of Freebase Form H of Compound A

Freebase Form H of Compound A was obtained via anti-solvent addition, wherein 15 mg of the amorphous freebase of Compound A was dissolved in about 0.4-1.0 mL of $CHCl_3$, followed by the addition of n-heptane until precipitant appeared or the total amount of anti-solvent reached 15.0 mL.

Preparation of Freebase Form I of Compound A

Freebase Form H of Compound A was obtained via anti-solvent addition, wherein 15 mg of the amorphous freebase of Compound A was dissolved in about 0.4-1.0 mL of DMSO, followed by the addition of 15.0 mL of $H_2O$. The sample was then transferred to slurry at 5° C. for 4 days.

Preparation of Freebase Form J of Compound A

Freebase Form J of Compound A was obtained during XRPD characterization of freebase Form E of Compound A. Since freebase Form J of Compound A was only obtained via heating freebase Form E of Compound A to 60° C. under N2 purge, it was postulated to be an anhydrate.

Freebase Polymorph Inter-Conversion

Polymorph conversion relationships among freebase Forms A, C, D, E, F, G and H of Compound A were obtained. About 20 mg of amorphous freebase starting material were added into a separate high-performance liquid chromatography (HPLC) vial followed by addition of 1.0 mL of corresponding solvent. The samples were slurried at rt at 1000 rpm for about 2~5 hrs. The samples were then filtered through 0.45 m polytetrafluoroethylene (PTFE) into separate HPLC vials, containing about 5 mg of each form. The samples were slurried at rt at 1000 rpm for XRPD characterization. The results are shown in Table 1. Except in MTBE, freebase Form E was obtained in all solvent systems. Freebase Form F was an anhydrate with DSC endotherm at higher temperature than Form E, and Form F was only obtained via heating. Form E can be obtained in all solvent systems of competitive slurry experiments.

TABLE 1

| Starting material | Solvent (v/v) | Time (d) | Form |
|---|---|---|---|
| Freebase Form A, C, D, E, F | MTBE | 4 | Freebase Form A |
| | Toluene | 7 | Freebase Form E |
| | $H_2O$ | 26 | Freebase Form E |
| | Acetone/$H_2O$ (1:3, $a_w$~0.93) | 4 | Freebase Form E |
| | ACN/$H_2O$ (1:3, $a_w$~0.94) | 4 | Freebase Form E |
| Freebase Form C, E, F | Acetone/n-heptane (1:3) | 13 | Freebase Form E |
| | EtOAc/n-heptane (1:3) | 13 | Freebase Form E |
| Freebase Form E, G, H | Toluene | 2 | Freebase Form E |
| | Acetone/$H_2O$ (1:3, $a_w$~0.93) | 2 | Freebase Form E |

Adipate salt Form A was stable in its solid state for 4 weeks at 25° C./60% relative humidity (RH) and at 40° C./75% RH, for 2 weeks at 60° C., and for 3 days at 80° C. It only slightly degraded at 60° C. after 2 weeks and at 80° C. after 3 days. As shown in Table 2, after 4 weeks at 60° C. and after 7 days at 80° C., adipate salt Form A degraded 0.9% and 0.6%, respectively. There was no form change under all tested conditions.

TABLE 2

| Condition | Time | Purity (area %) | Purity/Initial (%) |
|---|---|---|---|
| Initial | — | 98.72 | — |
| 25° C./60% RH | 2 week | 98.85 | 100.1 |
| | 4 week | 98.91 | 100.2 |
| 40° C./75% RH | 2 week | 98.82 | 100.1 |
| | 4 week | 98.85 | 100.1 |
| 60° C. | 2 week | 98.25 | 99.5 |
| | 4 week | 97.80 | 99.1 |
| Initial | — | 99.03 | — |
| 80° C. | 1 day | 99.02 | 100.0 |
| | 3 day | 98.77 | 99.7 |
| | 7 day | 98.44 | 99.4 |

Freebase Form E was stable in its solid state for 4 weeks at 25° C./60% RH, 40° C./75% RH, and 60° C., and for 7 days at 80° C., as shown in Table 3. There was no form change under all tested conditions.

TABLE 3

| Condition | Time | Purity (area %) | Purity/Initial (%) |
|---|---|---|---|
| Initial | — | 99.35 | — |
| 25° C./60% RH | 2 week | 99.37 | 100.0 |
| | 4 week | 99.39 | 100.0 |
| 40° C./75% RH | 2 week | 99.45 | 100.1 |
| | 4 week | 99.45 | 100.1 |
| 60° C. | 2 week | 99.35 | 100.0 |
| | 4 week | 99.16 | 99.8 |
| Initial | — | 99.44 | — |
| 80° C. | 1 day | 99.48 | 100.0 |
| | 3 day | 99.31 | 99.9 |
| | 7 day | 99.12 | 99.7 |

Adipate salt Form A and freebase Form E of Compound A samples obtained from solution crystallization were ground for about 5 mins followed by vacuum drying at 50° C. for 15 hrs or 58.5 hrs. The samples were characterized after drying and the results are summarized in Table 4.

TABLE 4

| Form | Drying time (h) | Weight loss (%, 150° C.) | Endo-therm (° C., peak) | HPLC purity (area %) | Solvent content (wt %) |
|---|---|---|---|---|---|
| Adipate | — | 2.4 | 179.9 | 98.9 | EtOAc (3.8) |
| Salt | 15 | 1.7 | 181.6 | 99.0 | EtOAc (2.5) |
| Form A | 58.5 | 0.9 | 179.9 | 98.9 | EtOAc (1.3) |
| Freebase | — | 4.2 | 114.3 | 99.6 | Acetone (0.2) |
| Form E | 15 | 4.6 | 112.5 | 99.4 | Acetone (0.1) |
| | 58.5 | 3.4 | 111.9 | 99.4 | Acetone (0.1) |

Hygroscopicity

Figure 41:
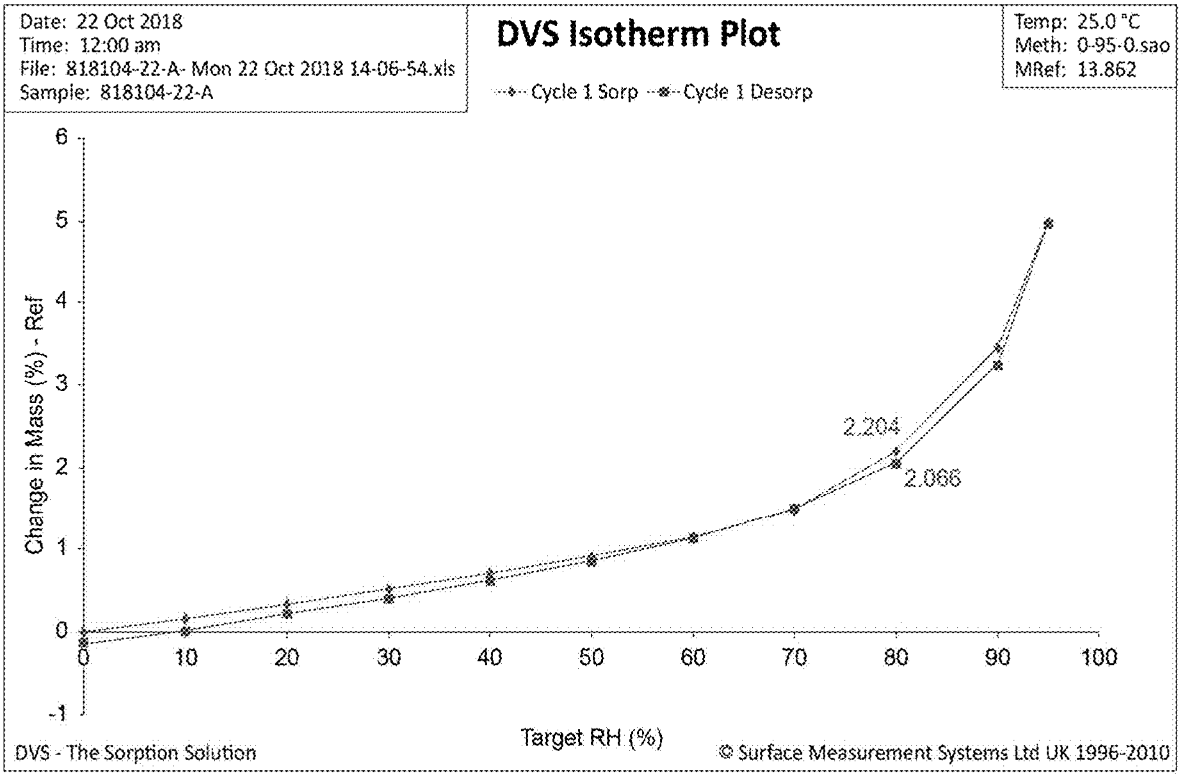
FIG. 41 provides a representative DVS plot of adipate salt Form A.
Figure 42:
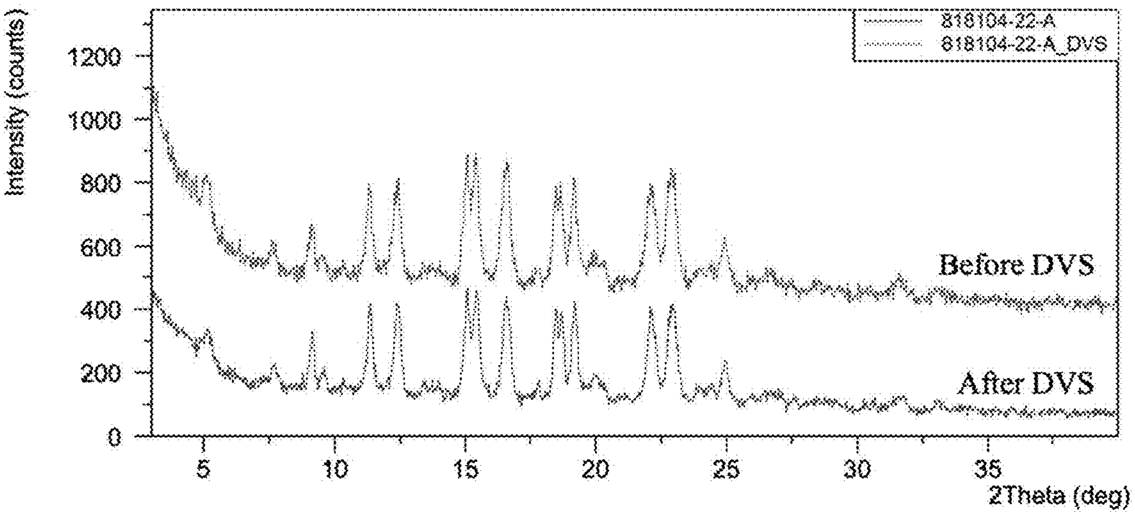
FIG. 42 provides a representative XRPD overlay of adipate salt Form A before and after DVS.
Figure 43:
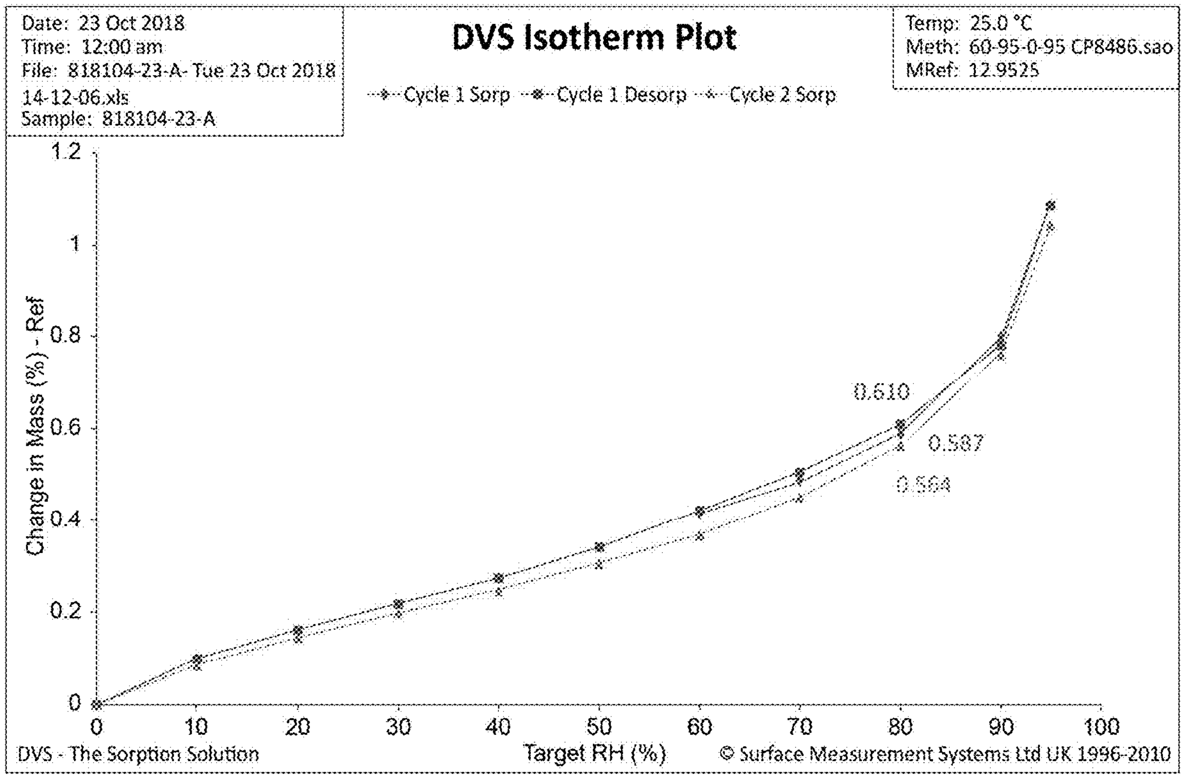
FIG. 43 provides a representative DVS plot of freebase Form E of Compound A.
Figure 44:
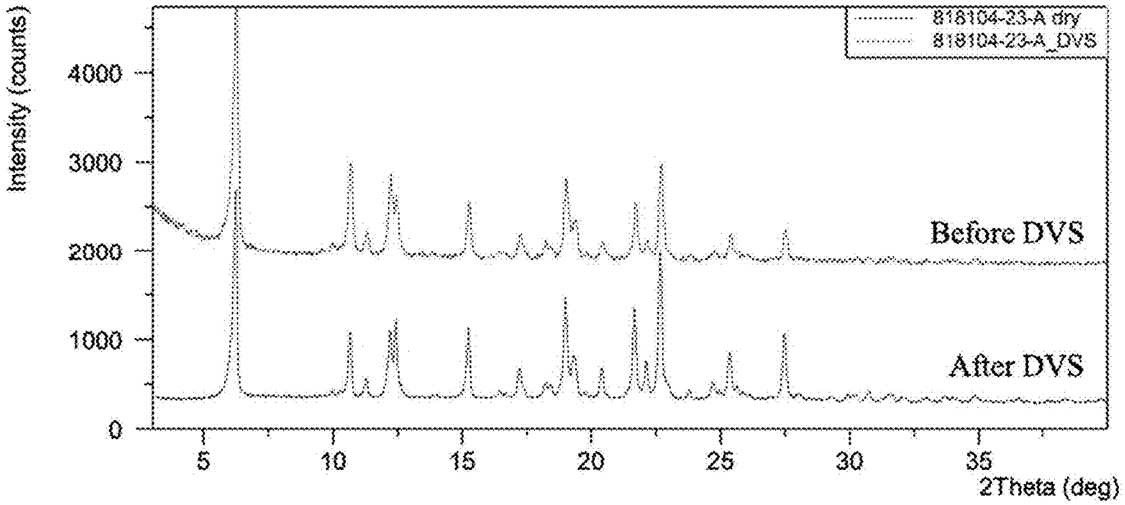
FIG. 44 provides a representative XRPD overlay of freebase Form E of Compound A before and after DVS.

Hygroscopicity of adipate salt Form A and freebase Form E of Compound A was evaluated by collecting DVS isotherm plots at 25° C. between 0% RH and 95% RH. XRPD characterization was performed for adipate salt Form A and freebase Form E of Compound A after DVS test. FIG. 41 depicts the DVS plot of adipate salt Form A, and FIG. 42 depicts XRPD overlay of adipate salt Form A before and after DVS. Based on the results, adipate salt Form A exhibited a water uptake of 2.2% at 25° C./80% RH. FIG. 43 depicts the DVS plot of freebase Form E of Compound A, and FIG. 44 depicts XRPD overlay of freebase Form E of Compound A before and after DVS. Based on the results, freebase Form E of Compound A exhibited a water uptake of 0.6% at 25° C./80% RH. No form change was observed after DVS test for both forms.

Equilibrium Solubility

Figure 45:
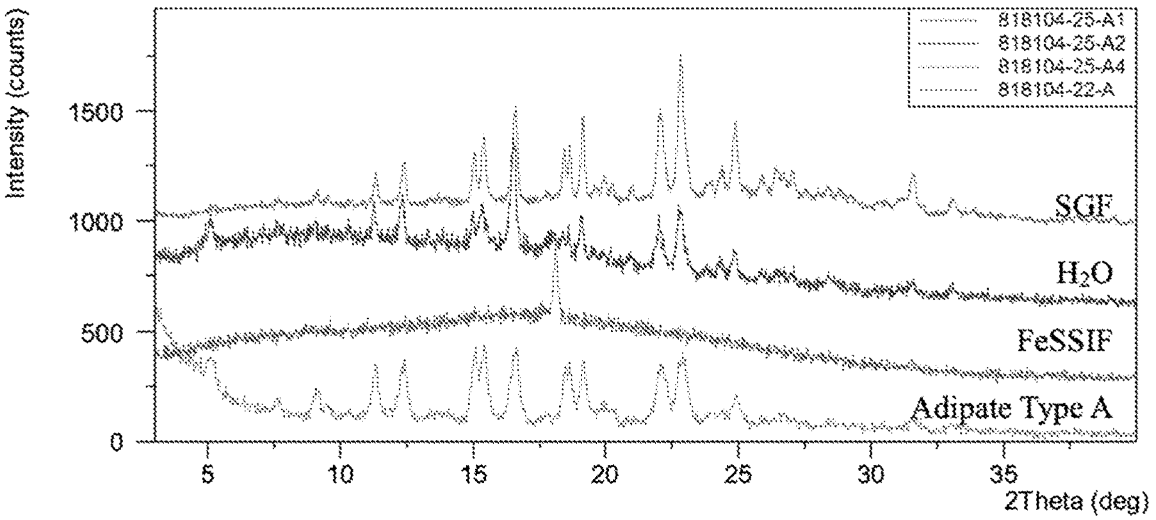
FIG. 45 provides a representative XRPD overlay of residual solids from the solubility test of adipate salt Form A.
Figure 46:
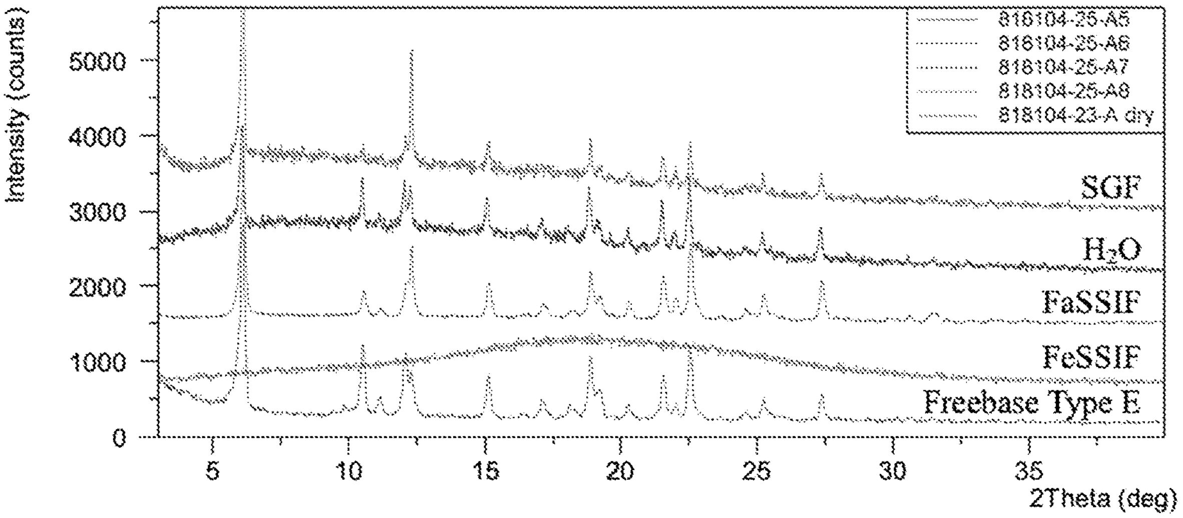
FIG. 46 provides a representative XRPD overlay of residual solids from the solubility test of freebase Form E of Compound A.

Equilibrium solubility of adipate salt Form A and freebase Form E of Compound A was evaluated in SGF, $H_2O$, FaSSIF and FeSSIF. About 10-50 mg of each sample was weighed into 1.0 mL of each medium followed by slurry at 37° C. for 24 hrs. The samples were centrifuged and filtered using 0.45 μm PTFE filter. The solids were tested by XRPD and the supernatants were tested by HPLC and pH. The results are summarized in Table 5. FIG. 45 depicts the XRPD overlay of the residual solids from the solubility test of adipate salt Form A. FIG. 46 depicts the XRPD overlay of the residual solids from the solubility test of freebase Form E of Compound A. Based on the results, adipate salt Form A exhibited higher solubility than freebase Form E of Compound A.

TABLE 5

| Form | Media | Solubility (mg/mL) | Form | pH |
|---|---|---|---|---|
| Adipate | SGF | 34.1 | Adipate Salt Form A | 4.4 |
| Salt | $H_2O$ | 25.5 | Adipate Salt Form A | 4.7 |
| Form A | FaSSIF | 30.8 | N/A | 4.8 |
| | FeSSIF | 5.6 | Adipate Salt Form A | 4.8 |
| Freebase | SGF | 9.0 | Freebase Form E | 6.6 |
| Form E | $H_2O$ | 0.099 | Freebase Form E | 8.4 |
| | FaSSIF | 1.4 | Freebase Form E | 6.8 |
| | FeSSIF | 2.6 | Amorphous | 5.4 |

The TGA curve of the amorphous freebase of Compound A indicated a substantial and gradual weight loss starting at 30° C. and continuing to 150° C. with a total of about 17% loss. In comparison, adipate salt Form A and freebase Form E of Compound A exhibited significantly less weight loss when heated to 150° C. Adipate salt Form A and freebase Form E and freebase Form J of Compound A are more thermodynamically stable than the amorphous freebase, and also have better processability.

CHARACTERIZATION METHODS

XRPD

For XRPD analysis, PANalytical Empyrean and X'Pert3 X-ray powder diffract meters were used.

Parameters for XRPD test

| Parameters | Empyrean | X' Pert3 |
|---|---|---|
| X-Ray wavelength | Cu, Kα; Kα1 (Å): 1.540598 Kα2 (Å): 1.544426 intensity ratio Kα2/Kα1: 0.50 | Cu, Kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA |
| Divergence slit | Automatic | 1/8 |
| Scan mode | Continuous | Continuous |
| Scan range (2θ/°) | 3~40 | 3~40 |
| Step size (2θ/°) | 0.0167 | 0.0263 |
| Scan step time (s) | 17.780 | 46.665 |
| Test time (s) | About 5 mins 30 s | About 5 mins |

TGA and DSC

TGA data were collected using a TA Q5000/Discovery 5500 TGA from TA Instruments. DSC was performed using a TA Q2000/Discovery 2500 DSC from TA Instruments.

Parameters for TGA and DSC test

| Parameters | TGA | DSC |
|---|---|---|
| Method | Ramp | Ramp/Custom |
| Sample pan | Aluminum, open | Aluminum, crimped/open |
| Temperature | RT- Target temperature | 25° C.- Target temperature |
| Heating rate | 10° C./min | 10° C./min |
| Purge gas | $N_2$ | $N_2$ |

DVS

DVS data was measured via a SMS (Surface Measurement Systems) DVS Intrinsic. The relative humidity at 25° C. was calibrated against the deliquescence point of LiCl, $Mg(NO_3)_2$ and KCl.

Parameters for DVS test

| Parameters | Values |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0% RH-95% RH |
| RH step size | 10% (90% RH-0% RH-90% RH) 5% (95% RH-90% RH and 90% RH-95% RH) |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. (R)-2-allyl-1-(7-ethyl-7-hydroxy-6,7-dihydro-5H-cyclopenta[b]pyridin-2-yl)-6-((4-(4-methylpiperazin-1-yl)phenyl)amino)-1,2-dihydro-3H-pyrazolo [3,4-d]pyrimidin-3-one (Compound A):

Compound A

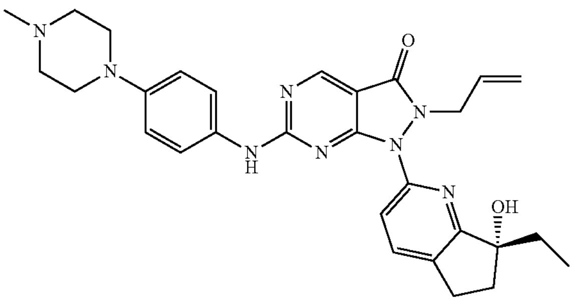

wherein Compound A is selected from the group consisting of adipate salt Form A of Compound A, freebase Form E of Compound A, freebase Form F of Compound A and freebase Form J of Compound A, wherein:

the adipate salt form A is characterized by one or more peaks in an X-ray powder diffraction pattern, wherein the one or more peaks are selected from 15.40 degrees 2θ ±0.2 degrees 2θ, 16.58 degrees 2θ ±0.2 degrees 2θ, 22.12 degrees 2θ ±0.2 degrees 2θ and 22.88 degrees 2θ ±0.2 degrees 2θ; and the freebase Form E of Compound A is a hydrate and is characterized by one or more peaks in an X-ray powder diffraction pattern, wherein the one or more peaks are selected from 6.20 degrees 2θ ±0.2 degrees 2θ, 12.40 degrees 2θ ±0.2 degrees 2θ, 18.96 degrees 2θ ±0.2 degrees 2θ and 22.62 degrees 2θ ±0.2 degrees 2θ;

the freebase Form F of Compound A is characterized by one or more peaks in an X-ray powder diffraction pattern, wherein the one or more peaks are selected from 5.14 degrees 2θ ±0.2 degrees 2θ, 6.24 degrees 2θ ±0.2 degrees 2θ, 10.19 degrees 2θ ±0.2 degrees 2θ and 12.40 degrees 2θ ±0.2 degrees 2θ; and the freebase Form J is an anhydrate and is characterized by one or more peaks in an X-ray powder diffraction pattern, wherein the one or more peaks are selected from 6.08 degrees 2θ ±0.2 degrees 2θ, 10.58 degrees 2θ ±0.2 degrees 2θ, 19.42 degrees 2θ ±0.2 degrees 2θ, 21.93 degrees 2θ ±0.2 degrees 2θ and 23.23 degrees 2θ ±0.2 degrees 2θ.

2. The compound of claim 1, wherein the Compound A is adipate salt Form A of Compound A.

3. The compound of claim 2, wherein the adipate salt Form A is characterized by peaks in an X-ray powder diffraction pattern, wherein the peaks are −15.40 degrees 2θ ±0.2 degrees 2θ, 16.58 degrees 2θ ±0.2 degrees 2θ, 22.12 degrees 2θ ±0.2 degrees 2θ and 22.88 degrees 2θ ±0.2 degrees 2θ.

4. The compound of claim 2, wherein the adipate salt Form A is characterized by a differential scanning calorimetry (DSC) thermogram comprising an endotherm in the range of about 75° C. to about 183° C.

5. The compound of claim 1, wherein the Compound A is freebase Form E of Compound A as a hydrate.

6. The compound of claim 5, wherein the freebase Form E is characterized by peaks in an X-ray powder diffraction pattern, wherein the peaks are 6.20 degrees 2θ ±0.2 degrees 2θ, 12.40 degrees 2θ ±0.2 degrees 2θ, 18.96 degrees 2θ ±0.2 degrees 2θ and 22.62 degrees 2θ ±0.2 degrees 2θ.

7. The compound of claim 5, wherein the freebase Form E is characterized by a DSC thermogram comprising an endotherm in the range of about 105° C. to about 125° C.

8. The compound of claim 5, wherein the freebase Form E is characterized by a DSC thermogram comprising an endotherm at approximately 115° C.

9. The compound of claim 5, wherein the freebase Form E is characterized by a weight loss of about 3.8% when heated from about 28 to ° C. about 150° C.

10. The compound of claim 1, wherein the Compound A is freebase Form F of Compound A.

11. The compound of claim 10, wherein the freebase Form F is characterized by peaks in an X-ray powder diffraction pattern, wherein the peaks are 5.14 degrees 2θ ±0.2 degrees 2θ, 6.24 degrees 2θ ±0.2 degrees 2θ, 10.19 degrees 2θ ±0.2 degrees 2θ and 12.40 degrees 2θ ±0.2 degrees 2θ.

12. The compound of claim 10, wherein the freebase Form F is characterized by a DSC thermogram comprising an endotherm in the range of about 163° C. to about 171° C.

13. The compound of claim 1, wherein the Compound A is Form J of Compound A as an anhydrate.

14. The compound of claim 13, wherein the freebase Form J is characterized by peaks in an X-ray powder diffraction pattern, wherein peaks are 6.08 degrees 2θ ±0.2 degrees 2θ, 10.58 degrees 2θ ±0.2 degrees 2θ, 19.42 degrees 2θ ±0.2 degrees 2θ, 21.93 degrees 2θ ±0.2 degrees 2θ and 23.23 degrees 2θ ±0.2 degrees 2θ.

15. A pharmaceutical composition comprising an effective amount of Compound A of claim 1, and a pharmaceutically acceptable carrier, diluent, excipient or combination thereof.

16. A method for ameliorating or treating a malignant growth or tumor comprising administering an effective amount of Compound A of claim 1, or a pharmaceutically acceptable salt thereof, to a subject in need thereof, wherein the malignant growth or tumor is due to a cancer selected from a breast cancer, a cervical cancer, an ovarian cancer, an uterine cancer, a vaginal cancer, a vulvar cancer, a brain cancer, a cervicocerebral cancer, an esophageal cancer, a thyroid cancer, a lung cancer, a stomach cancer, a gallbladder cancer, a bile duct cancer, a liver cancer, a pancreatic cancer, a colon cancer, a rectal cancer, a choriocarcinoma, an uterus body cancer, an uterocervical cancer, a renal pelvis cancer, a ureter cancer, a bladder cancer, a prostate cancer, a penis cancer, a testicular cancer, a fetal cancer, a Wilms' cancer, a skin cancer, a malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma and a non-Hodgkin's lymphoma.

17. The method of claim 16, wherein the cancer is a breast cancer, a cervical cancer, an ovarian cancer, an uterine cancer, a vaginal cancer or a vulvar cancer.

18. The method of claim 16, wherein the cancer is an ovarian cancer.

19. The method of claim 16, wherein the cancer is a lung cancer.

20. The method of claim 19, wherein the lung cancer is a small cell lung cancer.

21. The method of claim 16, wherein the cancer is an uterine cancer.

22. The method of claim 16, wherein the cancer is an osteosarcoma.

23. A method for ameliorating or treating a malignant growth or tumor comprising contacting the malignant growth or tumor with an effective amount of Compound A of claim 1, or a pharmaceutically acceptable salt thereof, to a subject in need thereof, wherein the malignant growth or tumor is due to a cancer selected from a breast cancer, a cervical cancer, an ovarian cancer, an uterine cancer, a vaginal cancer, a vulvar cancer, a brain cancer, a cervicocerebral cancer, an esophageal cancer, a thyroid cancer, a lung cancer, a stomach cancer, a gallbladder cancer, a bile duct cancer, a liver cancer, a pancreatic cancer, a colon cancer, a rectal cancer, a choriocarcinoma, an uterus body cancer, an uterocervical cancer, a renal pelvis cancer, a ureter cancer, a bladder cancer, a prostate cancer, a penis cancer, a testicular cancer, a fetal cancer, a Wilms' cancer, a skin cancer, a malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma and a non-Hodgkin's lymphoma.

* * * * *